(12) United States Patent
Santi et al.

(10) Patent No.: US 8,680,315 B2
(45) Date of Patent: Mar. 25, 2014

(54) PRODRUGS AND DRUG-MACROMOLECULE CONJUGATES HAVING CONTROLLED DRUG RELEASE RATES

(75) Inventors: Daniel V. Santi, San Francisco, CA (US); Gary W. Ashley, Alameda, CA (US)

(73) Assignee: Prolynx, LLC, Hayward, CA (US)

( * ) Notice: Subject to any disclaimer, the term of this patent is extended or adjusted under 35 U.S.C. 154(b) by 488 days.

(21) Appl. No.: 12/999,287

(22) PCT Filed: Jun. 26, 2009

(86) PCT No.: PCT/US2009/048943
§ 371 (c)(1),
(2), (4) Date: Feb. 24, 2011

(87) PCT Pub. No.: WO2009/158668
PCT Pub. Date: Dec. 30, 2009

(65) Prior Publication Data
US 2011/0263502 A1 Oct. 27, 2011

Related U.S. Application Data

(60) Provisional application No. 61/133,148, filed on Jun. 26, 2008, provisional application No. 61/192,050, filed on Sep. 15, 2008.

(51) Int. Cl.
| | | |
|---|---|---|
| *C07C 211/40* | (2006.01) | |
| *C07C 313/10* | (2006.01) | |
| *C07C 333/10* | (2006.01) | |
| *C07H 7/02* | (2006.01) | |
| *A61K 47/30* | (2006.01) | |
| *A61K 47/42* | (2006.01) | |
| *A61K 47/46* | (2006.01) | |
| *A61K 47/48* | (2006.01) | |
| *A61K 38/26* | (2006.01) | |
| *A61K 35/00* | (2006.01) | |

(52) U.S. Cl.
USPC .......... 558/260; 558/61; 558/238; 536/123.1; 530/300; 530/391.9; 530/362; 530/308; 514/11.7; 514/15.2

(58) Field of Classification Search
None
See application file for complete search history.

(56) References Cited

U.S. PATENT DOCUMENTS

| | | | |
|---|---|---|---|
| 6,232,318 B1 | 5/2001 | Nerenberg et al. | |
| 6,504,005 B1 | 1/2003 | Fridkin et al. | |
| 2006/0171920 A1* | 8/2006 | Shechter et al. | 424/85.4 |
| 2008/0064863 A1 | 3/2008 | Nagasaki et al. | |

FOREIGN PATENT DOCUMENTS

| | | |
|---|---|---|
| WO | WO-2004/089279 | 10/2004 |
| WO | WO-2007/021142 | 2/2007 |

OTHER PUBLICATIONS

Testa, B. Prodrug research: futile or fertile? Biochemical Pharmacology 68, 2097-2106 (2004).*
Ettmayer et al., Lessons Learned from Marketed and Investigational Prodrugs, Journal of Medicinal Chemistry, 47(10) 2393-2404 (2004).*
Laurence, D. R.; Carpenter, J.R. (1998). Dictionary of Pharmacology and Allied Topics.. Elsevier.*
Filpula et al., Bioconjugate Chemistry (2007) 18:773-784.
International Search Report for PCT/US09/048943, mailed on Sep. 1, 2009, 1 page.
Nesher et al., Bioconjugate Chemistry (2008) 19:342-348.
Veronese, Biomaterials (2001) 22:405-417.
Written Opinion of the International Searching Authority for PCT/US09/048943, mailed on Sep. 1, 2009, 5 pages.

* cited by examiner

*Primary Examiner* — Johann R Richter
*Assistant Examiner* — Mark Luderer
(74) *Attorney, Agent, or Firm* — Morrison & Foerster LLP

(57) ABSTRACT

The present invention provides methods and compositions that permit controlled and prolonged drug release in vivo. The compounds are either prodrugs with tunable rates of release, or conjugates of the drug with macromolecules which exhibit tunable controlled rates of release.

18 Claims, 5 Drawing Sheets

PRODRUGS AND DRUG-MACROMOLECULE CONJUGATES HAVING CONTROLLED DRUG RELEASE RATES

CROSS-REFERENCE TO RELATED APPLICATIONS

This application is the national phase of PCT application PCT/US2009/048943 having an international filing date of 26 Jun. 2009, which claims priority of U.S. provisional application Ser. Nos. 61/192,050 filed 15 Sep. 2008, and 61/133,148 filed 26 Jun. 2008. The contents of these documents are incorporated herein by reference in their entirety.

TECHNICAL FIELD

The invention relates to compounds that are designed for pharmacokinetic control in delivering drugs. In particular, the invention relates to prodrugs and drug-macromolecule conjugates having desired rates of drug release.

BACKGROUND ART

Many drugs suffer from unfavorable pharmacokinetic parameters that limit their effectiveness. Rapid clearance of such drugs from physiological compartments, either via metabolism or excretion, results in short lifetimes and reduced exposure to targets. For example, the therapeutic potential of peptide- and protein-based drugs is enormous, yet peptide- and protein-based drugs often suffer rapid systemic clearance due to metabolic instability and renal clearance. Similarly, nucleic acids such as antisense DNA and small interfering RNAs (siRNAs) have great therapeutic potential, yet suffer from metabolic instability and cell impermeability. Finally, many small organic molecules also suffer from rapid clearance that limits their therapeutic effectiveness.

It would thus be highly desirable to have methods to prolong the half-life in the systemic circulation and/or other physiological compartments and improve the availability and cell uptake of small molecule, peptide-, protein-, and nucleic acid-based therapeutics in order to provide improved drug- and gene-based therapies in the treatment of disease.

One method for increasing the physiological half-life of drugs is to increase their hydrodynamic size by attaching them to macromolecules. Removal of large molecules, for example high-molecular weight proteins, antibodies, polymers, poly(ethyleneglycol) (PEG), from the systemic circulation can be extremely slow. Metabolism of PEG having mw>5000 is insignificant, and both glomerular filtration and biliary excretion of PEG having mw ~50 kDa is minimally effective. For example, the plasma half-lives in rates or mice of several PEG-superoxide dismutase (PEG-SOD) conjugates have been reported to vary from 1.5 hours for a conjugate using PEG of molecular weight 1900 to 36 hours for a conjugate using PEG of molecular weight 72,000, while the half-life of unconjugated SOD was 0.08 hour. See Veronese, "Peptide and protein PEGylation: a review of problems and solutions," *Biomaterials* (2001) 22:405-417. Monoclonal antibody and serum albumin likewise have very long resident times in the systemic and other physiological compartments, which leads to greatly extended systemic/compartmental half-lives of macromolecular conjugated drugs, largely dependent upon the molecular weight of the conjugate.

For peptide- and protein-based drugs, covalent attachment of polymer residues, for example PEG (known as "PEGylation"), has been effective at improving the pharmacokinetic parameters and can also mask the drug agent from metabolism and from the immune system, leading to reduced immunogenicity. PEGylation has resulted in such modified drugs as PEG-bovine adenosine deaminase for the treatment of X-linked severe combined immunogenicity syndrome (ADAGEN®, Enzon), PEG-alpha interferon for the treatment of hepatitis C (PEGASYS®, Hoffman-LaRoche; PEG-Intron®, Schering-Plough/Enzon), PEG-L-asparaginase from the treatment of acute lymphoblastic leukemia (Oncaspar®, Enzon), PEG-recombinant human granulocyte colony stimulating factor for the treatment of neutropenia (Neulasta®, Amgen), PEG-anti-tumor necrosis factor alpha for the treatment of Crohn's disease (Cimzia®, Enzon), PEG-growth hormone receptor antagonist for the treatment of acromegaly (Somavert®, Pfizer), and PEG-anti-TNF Fab for rheumatoid arthritis (CD870, Pfizer).

PEGylation has also been shown to improve delivery of nucleic acids to cells. For example, US patent publication 2008/0064863 discloses double-stranded nucleic acids, one strand of which is covalently attached to a poly(ethyleneoxide) unit, in complex with a polycation for use in the delivery of nucleic acid drugs to cells. PCT publication WO2007/021142 discloses covalently PEGylated siRNA molecules. PEG-anti-VEGF aptamer has been approved for intraocular treatment of age-related macular degeneration (Macugen®, OSI/Pfizer).

PEGylation of small molecules has also been reported. EZN-2208, a PEG conjugate of SN-38, the active metabolite of irinotecan, has been shown to be active in preclinical tumor models. In this instance, PEGylation improves the solubility of the small molecule drug.

Covalent attachment of peptide and protein drugs to macromolecules other than PEG has been disclosed. For example, conjugates of various peptide drugs, such as thrombospondin-1 mimetic peptides, angiopoietin-2 antagonist, glucagon-like peptide-1 (GLP-1), and exendins, with a monoclonal antibody have been reported.

Covalent modification of peptides, proteins and small molecules with PEG, or other macromolecules, often causes deleterious loss of the biological activity of the parent drug, however. Thus, some recent activity has focused on development of reversible, or transient, PEGylation, in which the polymer chains are conjugated to the drug through a cleavable linker unit. The final PEGylated conjugate is of sufficient molecular size to have favorable systemic retention. Under physiological conditions, cleavage of the linker unit by enzyme or chemical action leads to release of a drug or prodrug that is rapidly converted to the active drug. Depending upon the rate of cleavage of the linker unit relative to the clearance rate of the prodrug or free drug, sufficient steady-state concentrations of active drug for biological activity may be realized using this approach.

Success has been reported using this approach, for example, using the immunotoxin SS1P reversibly-conjugated to PEG through lysine residues. See Filpula, et al., "Releasable PEGylation of Mesothelin Targeted Immunotoxin SS1P Achieves Single Dosage Complete regression of a Human Carcinoma in Mice," *Bioconjugate Chemistry* (2007) 18:773-784. Whereas unmodified SS1P was eliminated from mouse plasma with a half-life of about 26 minutes, reversible PEGylation extended the half-life to 2.5-5 hours. Reversible PEGylation of atrial natriuretic peptide (having a plasma half-life of 2-5 minutes) has been shown to result in prolonged protracted effects on blood pressure in adrenaline-treated rats (Nesher, et al., *Bioconjugate Chem* (2008) 19:342-348).

Most methods for reversible PEGylated or other macromolecular conjugated drugs suffer potential drawbacks. For example, some require enzyme hydrolysis by serum proteases or esterases, others need a reducing environment to cleave a disulfide linker, and most release a "self-immolative" prodrug that undergoes spontaneous cleavage to the active drug and a small, potentially toxic alkylating agent. It would be beneficial to design versions of reversible PEGylation or macromolecular drug attachment that do not require and are unaffected by difficult-to-control entities such as enzymes, and redox environments.

U.S. Pat. No. 6,504,005 describes prodrug molecules that release active drug under physiological conditions by virtue of beta elimination department on pH. A specific embodiment of this approach is described in WO2004/089279. This approach, albeit limited in scope and examples, utilizing a spontaneous, first-order rate of cleavage of the drug from the PEG carrier that is initiated when the conjugate is exposed to physiological pH, is described in US Patent Publication 2006/0171920. A general strategy for providing macromolecule-drug conjugates having a variety of spontaneous, first-order release rates that are predictable and controllable under physiological conditions would provide a valuable therapeutic tool for the treatment of disease.

DISCLOSURE OF THE INVENTION

The present invention provides prodrugs and drug-macromolecule conjugates for controlling the delivery rate of therapeutic agents ("drugs") when administered to patients requiring treatment with the therapeutic agents. The prodrugs and drug-macromolecule conjugates of the invention provide a means of delivering therapeutic agents over a sustained period of time, even for therapeutic agents which are rapidly cleared from the system, thus prolonging the therapeutic effects of the therapeutic agents.

In one aspect, the invention is directed to compounds that are drug-macromolecule conjugates of the formula

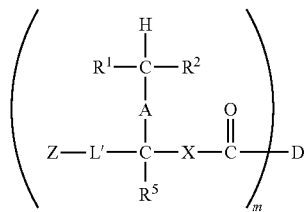

(3)

wherein m is an integer of 1-10;
Z is the residue of a macromolecule;
L' is the residue of a linker;
D is the residue of a drug or of a prodrug;
X is O or S;
A is alkenyl ($C_2$), aryl or absent;
each $R^1$ and $R^2$ is independently H; CN; $NO_2$;
optionally substituted aryl;
optionally substituted heteroaryl;
optionally substituted alkenyl;
optionally substituted alkynyl; or
each $R^1$ and $R^2$ is independently $COR^3$ or $SOR^3$ or $SO_2R^3$ wherein
 $R^3$ is H or optionally substituted alkyl;
  optionally substituted aryl;
  optionally substituted heteroaryl;
  optionally substituted alkenyl;
  optionally substituted alkynyl; or OR or $NR_2$ wherein each R is independently H or optionally substituted alkyl; or
each $R^1$ and $R^2$ is independently $SR^4$ wherein
 $R^4$ is optionally substituted alkyl;
 optionally substituted aryl;
 optionally substituted heteroaryl;
 optionally substituted alkenyl; or
 optionally substituted alkynyl;
wherein $R^1$ and $R^2$ may be joined to form a 3-8 member ring; and
wherein both $R^1$ and $R^2$ cannot be H;
wherein $R^5$ is H or alkyl ($C_{1-6}$).

Typically, the linker residue is a bivalent chain having a molecular weight between 14 Da and 20 kDa which may include unsaturation, heteroatoms, ring structures, aromatic portions, and/or heteroaromatic portions that covalently links Z to the remainder of the molecule. The linker may include a peptide backbone, a pseudopeptide backbone, a triazole, a phenylene, or a maleimido residue or combinations thereof. In some embodiments, the carbonyl shown in formula (3) originates in the drug itself. In some embodiments, m is 1 and/or $R^5$ is H. The value of m may also be any intermediate integer between 1 and 10; thus m may be 2, 5, 7, or any intervening integer.

In another aspect, the present invention provides prodrugs having the formula (2)

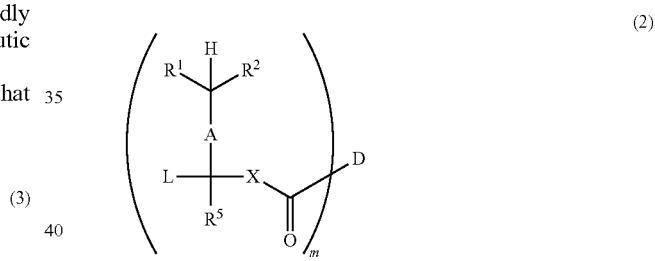

(2)

wherein
m, X, A, $R^1$, $R^2$ and $R^5$ are defined as above, L is a linking group that can attach to a macromolecule, and
D is the residue of a drug or a prodrug.
In some embodiments, m is 1 and/or $R^5$ is H.

The compounds of formula (3) and of formula (2) release the drug or prodrug at controlled rates under physiological conditions in the body, by non-enzymatic elimination. The rate of drug release is tunable by the appropriate choice of groups $R^1$ and $R^2$. In some embodiments, each of groups $R^1$ and $R^2$ may be independently substituted by electron-donating and/or electron-withdrawing substituents that alter the acidity of the intervening $R^1$—CH—$R^2$ proton so that enormous flexibility and control over the rate of drug elimination can be achieved. In certain embodiments of the invention, mixtures of compounds of formula (3) or of formula (2), each with a different rate of drug release under physiological conditions, may be used in order to provide tailored drug delivery profile to a patient in need of treatment.

The invention is also directed to methods to prepare the compounds of formulas (3) and (2) as well as compounds that are intermediates in their formation. Thus, in another aspect, the invention is directed to compounds of the formula

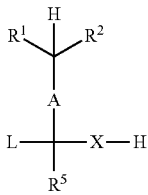

(1)

wherein A, X, L, R¹, R² and R⁵ are as above defined.

The invention also provides compounds of the formula

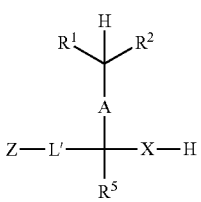

(4)

wherein

X, A, L', Z, R¹, R² and R⁵ are defined as above.

The invention is also directed to pharmaceutical compositions containing compounds of formulas (2) or (3) and to methods to prepare these prodrugs or macromolecular conjugates. In general, the starting point is the compound of formula (1) which may be converted directly to the prodrugs of formula (2) by suitable reaction with the drug compound. The prodrug of formula (2) can then, in turn, be converted to the macromolecular conjugate of formula (3) by virtue of reaction of L with the macromolecule, Z. Alternatively, the compound of formula (3) may be prepared by converting the compound of formula (1) to the compound of formula (4) which is then reacted with the drug.

MODES OF CARRYING OUT THE INVENTION

Figure 1:
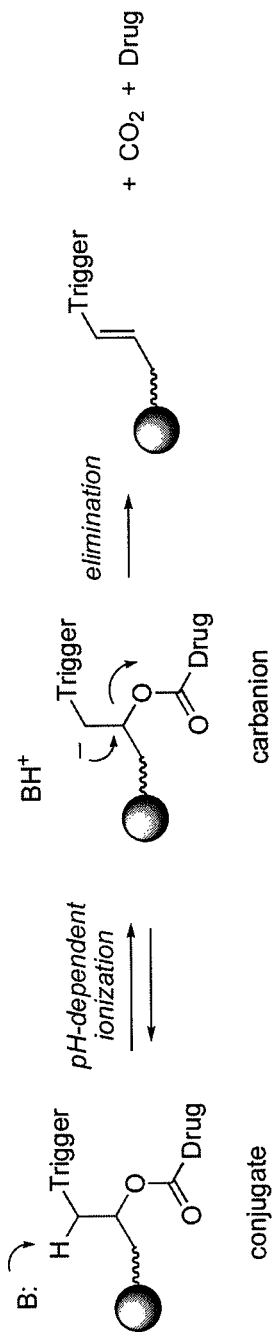
FIG. 1 shows the base-catalyzed elimination of drug from the macromolecular carrier-drug conjugate of the invention.
Figure 2:
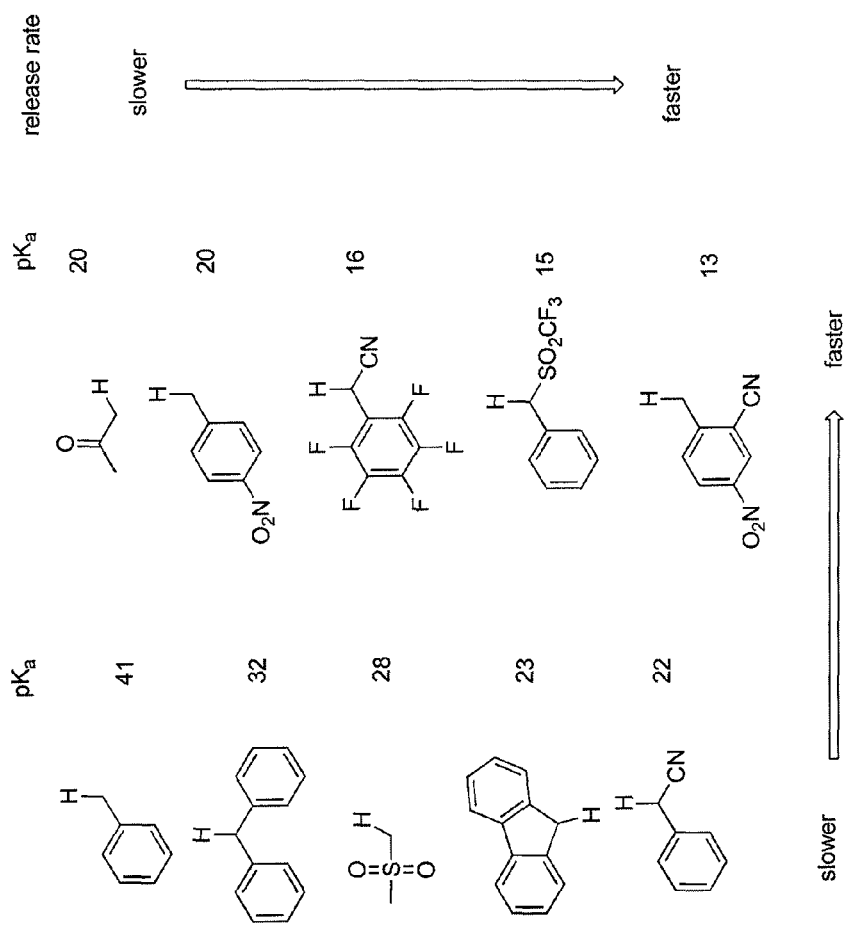
FIG. 2 shows a variety of functional groups for R¹ and R² and their effects on the acidity of adjacent protons. As the acidity increases (lower pKa), the rate of deprotonation and hence the rate of drug release from the prodrug or drug-macromolecular conjugate is expected to increase.
Figure 3:
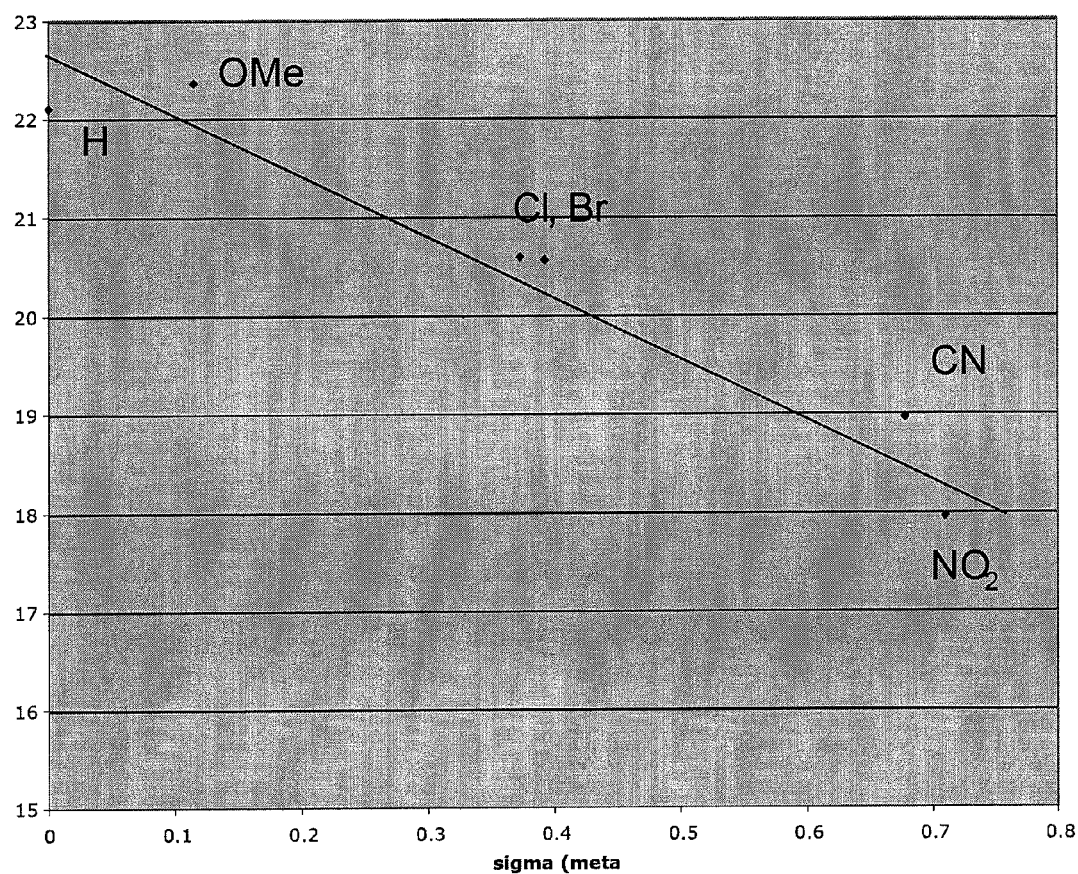
FIG. 3 shows the effect of substitution on the acidity of the 9-proton in various 2-substituted fluorenes. A shown, the effect follows the expected Hammett linear free energy correlation, such that the acidity of any given 2-substituted fluorene can be closely estimated based on the sigma-parameter of the substituent.

The compounds of formulas (2) and (3) are designed to control the pharmacokinetics of the drug or prodrug defined as "D". The mechanism whereby the drug or prodrug, D, is released is shown in FIG. 1 using formula (3) for illustration. The rate is controlled according to a pH dependent elimination mechanism. The groups R¹ and R² are selected to provide the appropriate reactivity of the intervening proton R¹—CH—R², as illustrated in part in FIG. 2, and thus providing control over the rate of drug or prodrug release from the prodrug or conjugate. The nature of the linking group and the group A also influence this process, providing multiple points of control over the rate of drug release from the resulting conjugate. The properties of R¹ and R² may be modulated by the optional addition of electron-donating or electron-withdrawing substituents, as illustrated in FIG. 3.

A particular advantage of the invention is the position of attachment of the linking group. While it is possible to attach a linking group to one of groups R¹ or R², doing so complicates any further substitution chemistry of R¹ or R², and may result in electronic interactions between the linking group and the electron-donating or electron-withdrawing substituents, thus limiting the tunability of the release rates.

While typically, the active form of the drug is directly released from the conjugates of the invention, in some cases, it is possible to release the active drug in the form of a prodrug thereof. On example of such a system is shown below:

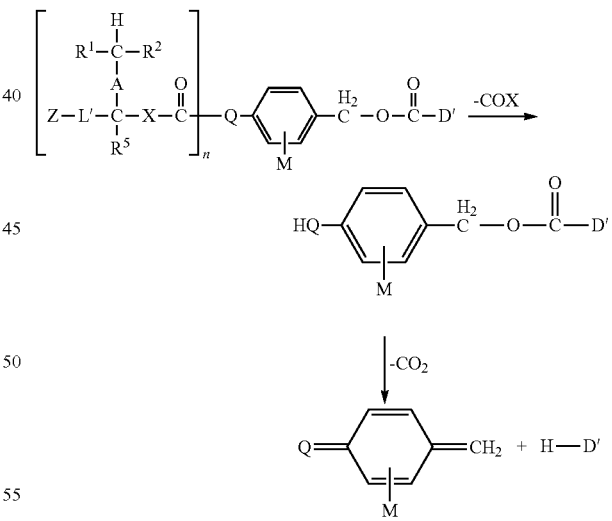

wherein Q=O or NH, D' is the active form of a drug,

M=usual aryl substitutions.

As noted above, the compounds of formulas (2) and (3) provide tunable release rates for drugs or prodrugs so as to control the pharmacokinetics of these drugs. In order to prepare these compounds, various intermediates are of the formulas (1), (2) and (4); as noted, the compounds of formula (2) are also prodrugs with tunable release rates. The compounds of formula (1) have neither the drug/prodrug nor the macromolecule attached and can be regarded as starting materials.

Because the substituents $R^1$, $R^2$, $R^5$, A, and X are shared by all of these compounds, the various embodiments of these substituents as presented in the alternative set forth below in connection with the compounds of formula (1) may be extrapolated to compounds of formulas (2), (3) and (4). In addition, the nature of L in formulas (1) and (2) determines the nature of L' in formulas (4) and (3). Thus, the alternatives described below for formula (1) are hereby imported as alternatives into formulas (2), (3) and (4).

Definitions

By the term "electron-donating group" is meant a substituent resulting in a decrease in the acidity of the benzylic H group. Examples of suitable electron-donating substituents include but are not limited to lower alkyl, lower alkoxy, lower alkylthio, amino, alkylamino, and dialkylamino. By the term "electron-withdrawing group" is meant a substituent resulting in an increase in the acidity of the benzylic H group. Examples of suitable electron-withdrawing substituents include but are not limited to halogen, difluoromethyl, trifluoromethyl, nitro, cyano, C(=O)—R, wherein R is H, lower alkyl, lower alkoxy, or amino, or SOR or $SO_2R$, where R is lower alkyl, aryl, or heteroaryl. Non-hydrogen electron-donating or electron-withdrawing substituents may be present in multiple positions on rings to which they are bound. While, for convenience, in most examples, only a single occurrence of a non-hydrogen substituent on a single ring is shown, multiple substituents may also be present and are within the scope of the invention. The substituents may be the same or different.

The term "alkyl" is meant to include linear, branched, or cyclic saturated hydrocarbon groups of 1-8 carbons, or in some embodiments 1-6 or 1-4 carbon atoms.

The term "alkenyl" is meant to include non-aromatic unsaturated hydrocarbons with carbon-carbon double bonds. By the term "alkenyl ($C_2$)" is meant a mono-, di-, tri-, or tetra-substituted carbon-carbon double bond of any geometric configuration.

The term "alkynyl" is meant to include non-aromatic unsaturated hydrocarbons with carbon-carbon triple bonds. By the term "alkynyl ($C_2$)" is meant a mono- or di-substituted carbon-carbon triple bond.

The term "alkoxy" is meant to include alkyl groups bonded to oxygen, including methoxy, ethoxy, isopropoxy, cyclopropoxy, cyclobutoxy, and similar.

The term "aryl" is meant to include aromatic hydrocarbon groups of 6-18 carbons, preferably 6-10 carbons, including groups such as phenyl, naphthyl, and anthracenyl. The term "heteroaryl" is meant to include aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

The term "halogen" includes bromo, fluoro, chloro and iodo.

By the term "maleimido" is meant a group of the formula

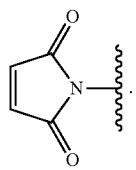

The terms "protein" and "peptide" are used herein interchangeably regardless of chain length, and these terms further include pseudopeptides which comprise linkages other than amide linkages, such as $CH_2NH_2$ linkages as well as peptidomimetics.

The terms "nucleic acids" and "oligonucleotides" are also used interchangeably regardless of chain length. The nucleic acids or oligonucleotides may be single-chain or duplexed or may be DNA, RNA, or modified forms thereof with altered linkages, such as phosphodiesters, phosphoramidates, and the like. For both the proteins and nucleic acids useful as drugs in the invention, these terms also include those with side chains not found in nature in the case of proteins and bases not found in nature in the case of nucleic acids.

Small molecules in the context of drugs is a term well understood in the art, and is meant to include compounds other than proteins and nucleic acids that either are synthesized or are isolated from nature and in general do not resemble proteins or nucleic acids. Typically, they have molecular weights <1,000, although there is no specific cutoff recognized. Nevertheless, the term is well understood in the fields of pharmacology and medicine.

By the term "macromolecule" is meant a macromolecule having a molecular weight of between about 10,000 and 100,000, which is itself essentially devoid of cytotoxic, hormonal, or cell signaling activity but is capable of conjugation to an active drug molecule so as to serve to carry the active drug molecule in the systemic circulation and provides a reservoir of active drug which is released over time.

When $R^1$ and $R^2$ are joined to form cyclic structures, this includes groups wherein the $R^1$—CH—$R^2$ moiety forms a substructure such as, for example,

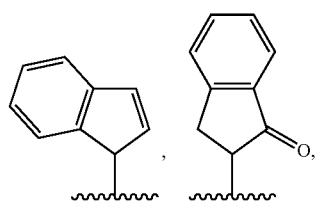

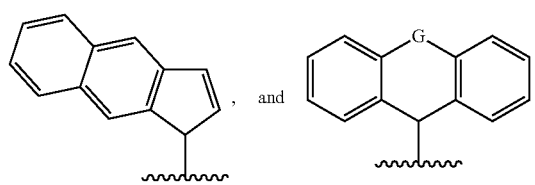

and forms thereof optionally substituted with electron-withdrawing and/or electron-donating groups as described above, wherein G is a bond; C=O; SO, $SO_2$, $CX_2$, or $CX_2CX_2$ wherein each X independently is H or Cl.

Variants of Formula (1)

In the examples set forth below, it will be noted that aryl groups, for example, typically contain only one substituent. This is for simplicity only, it will be understood that embodiments of $R^1$ and $R^2$ wherein ring systems contain multiple non-hydrogen substituents are included. Preferably the number of substituents on a single ring is 1, 2 or 3.

In some embodiments of the invention, compounds of formula (1) have more specific formula:

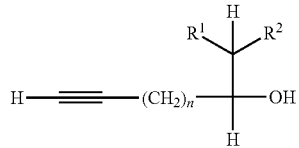

or the formula:

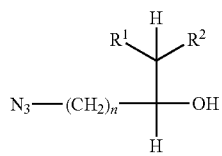

wherein n=1-6.

In some embodiments, the molecules of formula (1) have the more specific formula (1a)

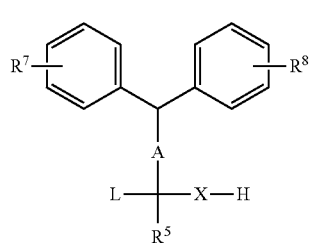
(1a)

wherein $R^7$ and $R^8$ are each independently H, an electron-donating group, or an electron-withdrawing group, and wherein electron donating and/or electron withdrawing forms of $R^7$ and $R^8$ are present at 1-5 positions preferably 3 or less, on the phenyl moieties; X is O or S; A is alkenyl ($C_2$), aryl, or absent; and L is a linking group capable of being attached to a macromolecule, $R^5$ is H or alkyl ($C_{1-6}$), for example,

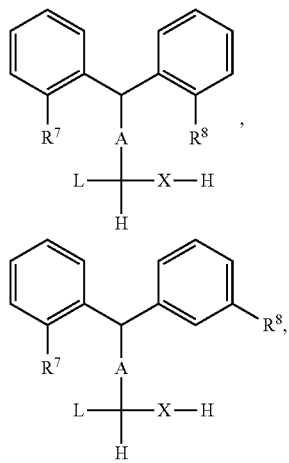

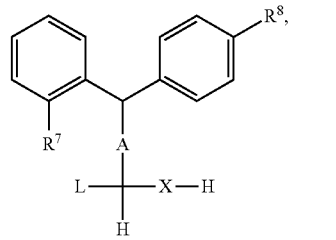

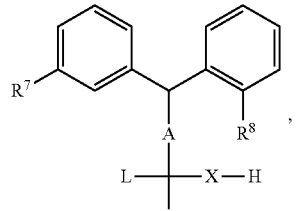

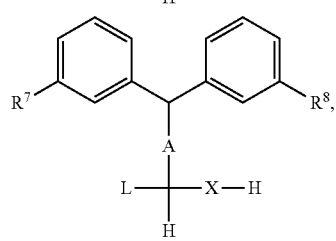

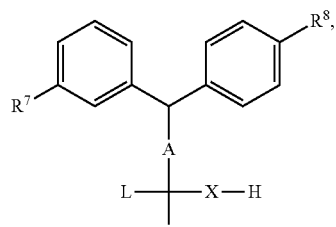

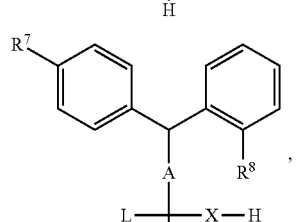

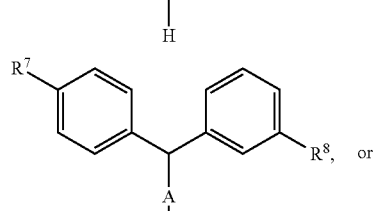

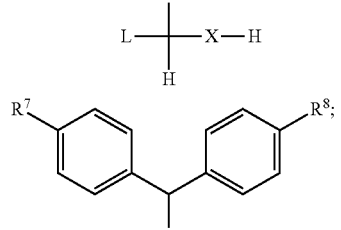, or

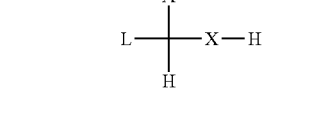

or,
for example
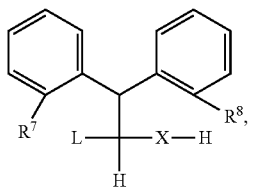
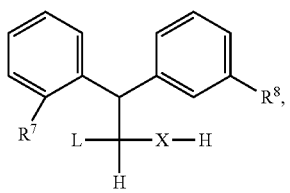
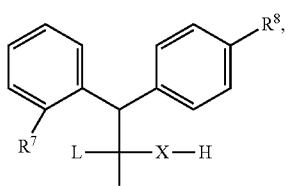
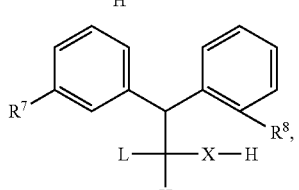
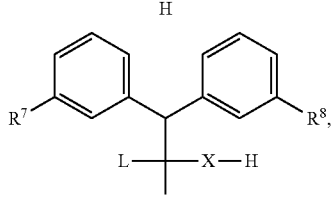
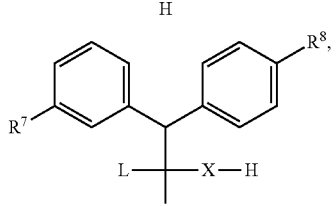
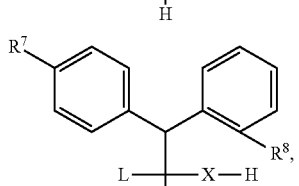
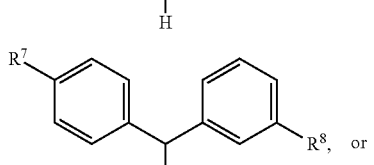, or
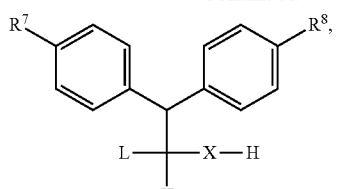
for example
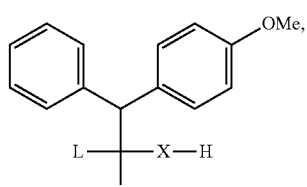
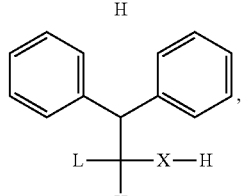
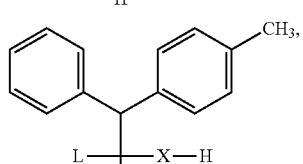
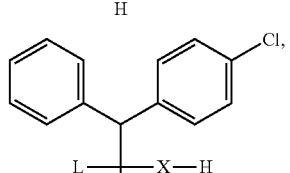
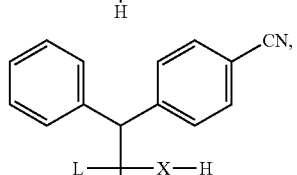
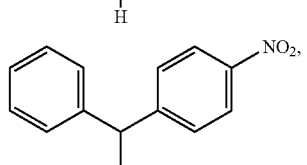
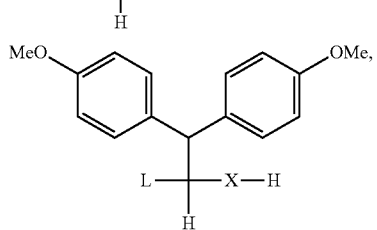

-continued
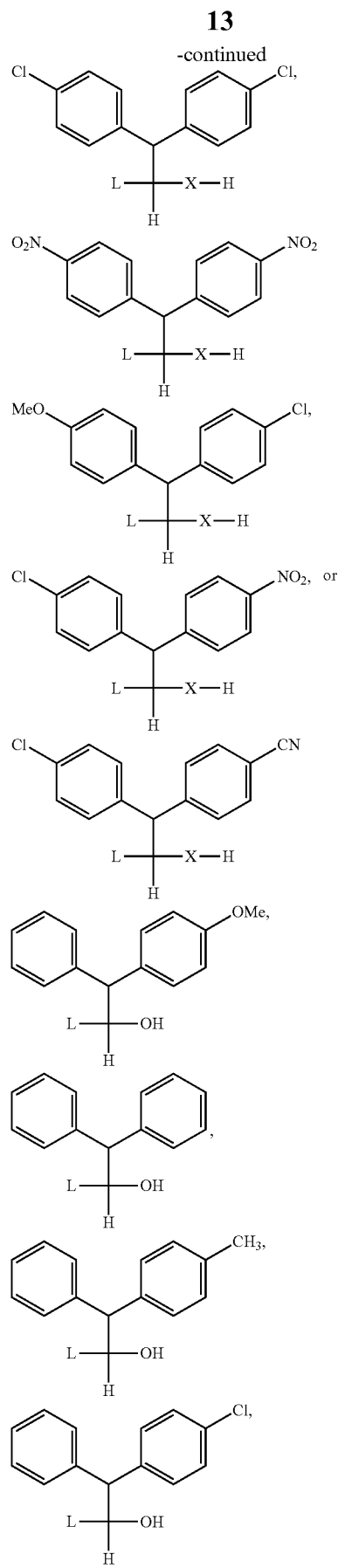
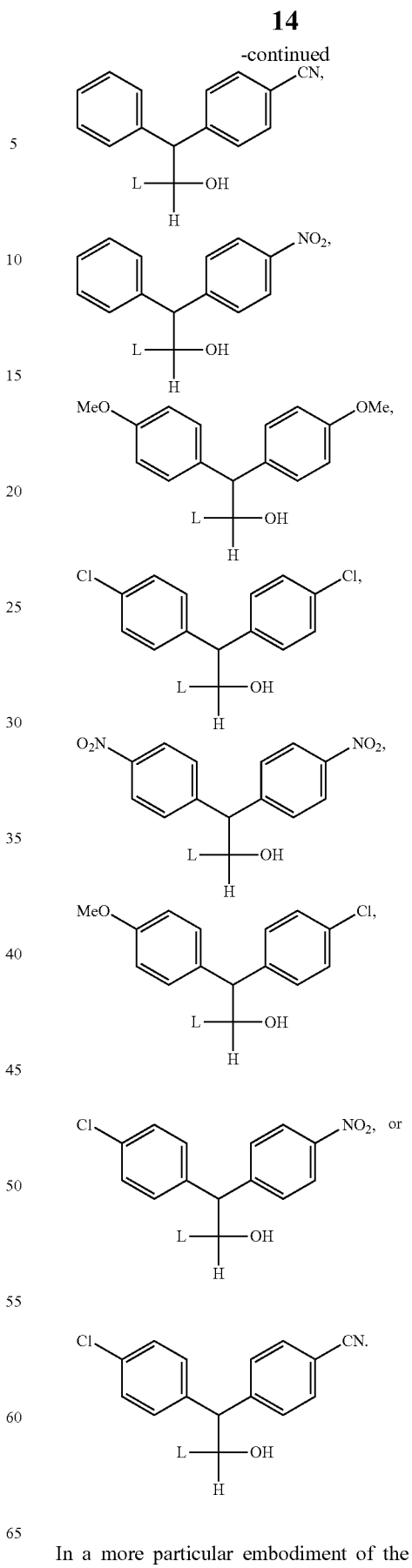
In a more particular embodiment of the invention, the molecules of formula (1) have the more specific structure (1b)

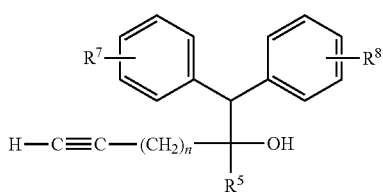
(1b)
wherein, as above, $R^7$ and $R^8$ are each independently H, an electron-donating group, or an electron-withdrawing group, and wherein electron donating and/or electron withdrawing forms of $R^7$ and $R^8$ are present at 1-5 positions on the phenyl moieties; $R^5$ is H or alkyl ($C_{1-6}$), and n=1-6.
Examples include
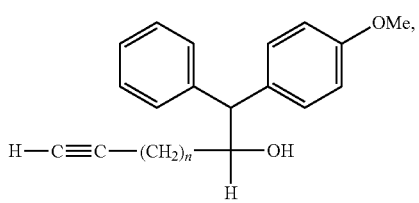
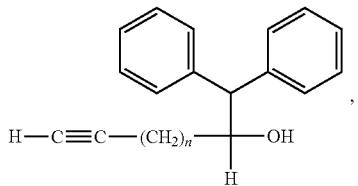
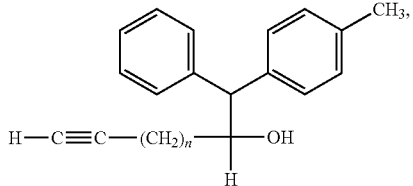
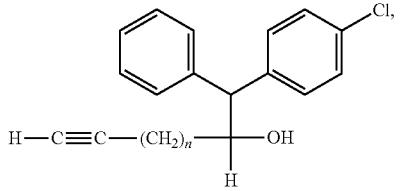
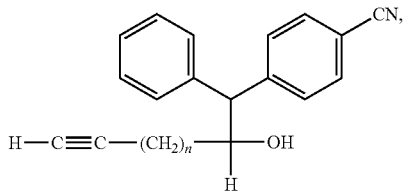
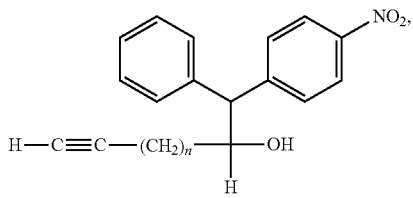
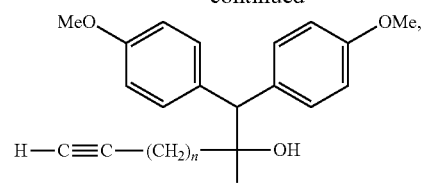
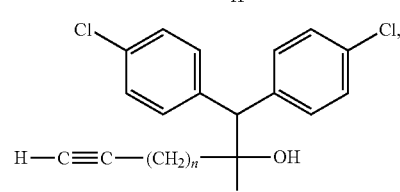
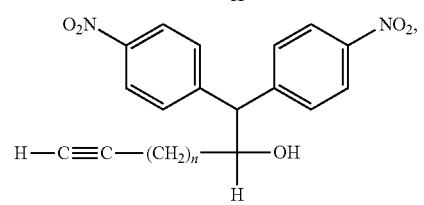
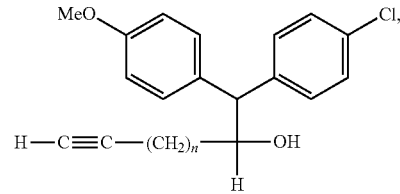
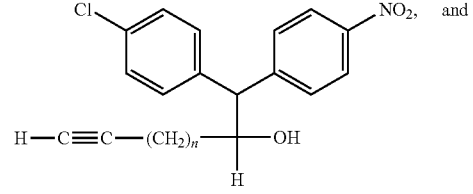
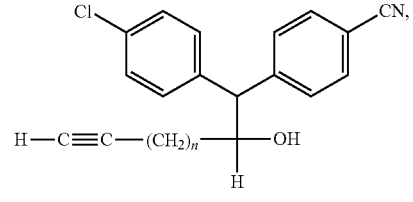
as well as
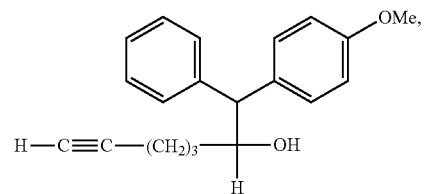
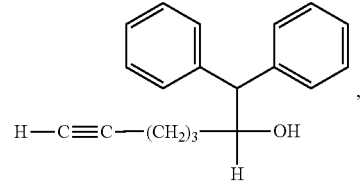

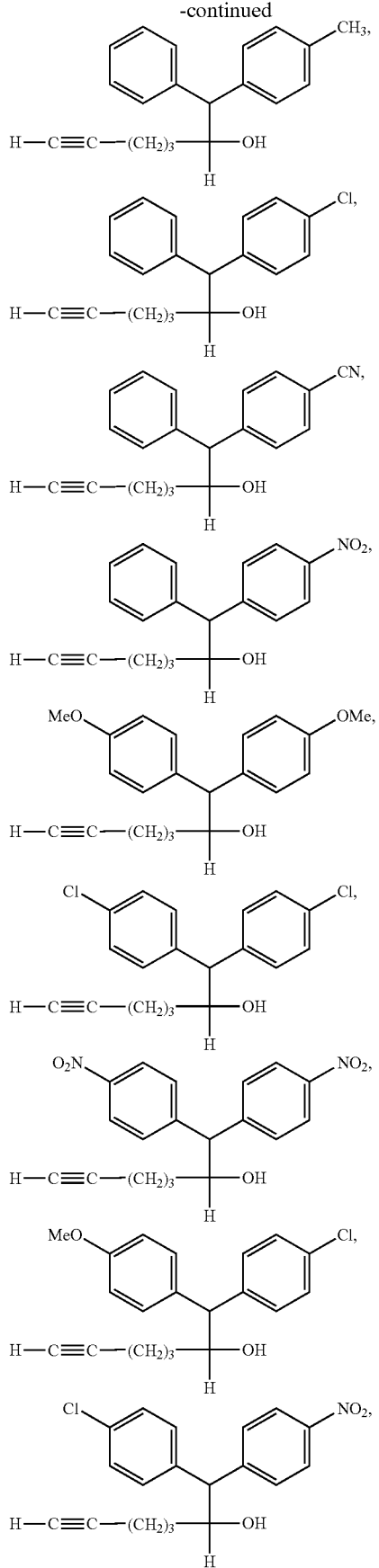

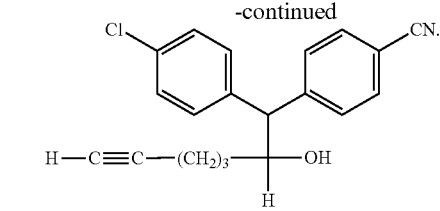

In certain embodiments of the invention, the molecules of formula (1) have the more specific formula (1c)

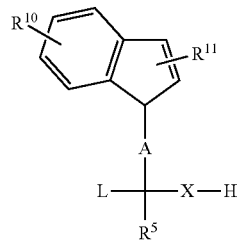

(1c)

wherein X is O or S; A is alkenyl ($C_2$), aryl, or absent; L is a linking group capable of being attached to a macromolecule; and wherein $R^5$ is H or alkyl ($C_{1-6}$), $R^{10}$ and $R^{11}$ are each independently H, an electron-donating group, or an electron-withdrawing group and wherein $R^{10}$ and $R^{11}$ may occur as non-hydrogen substituents at 1-4 or 1-2 positions in their respective rings. Examples include

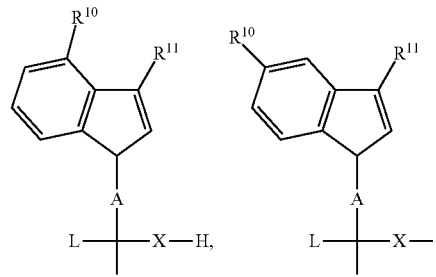

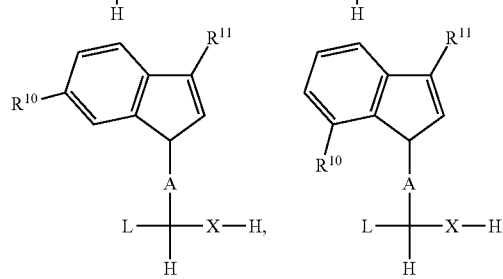

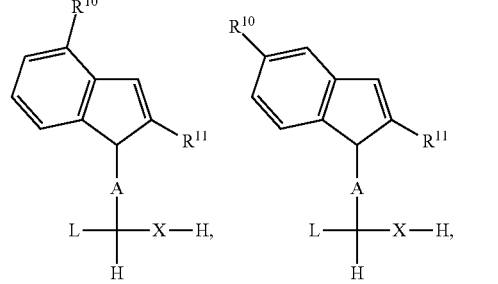

-continued

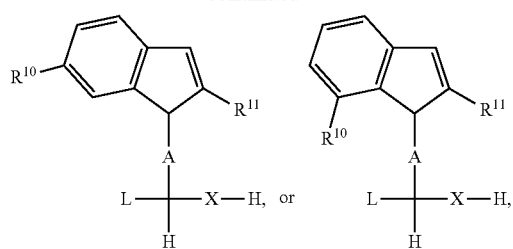

as well as

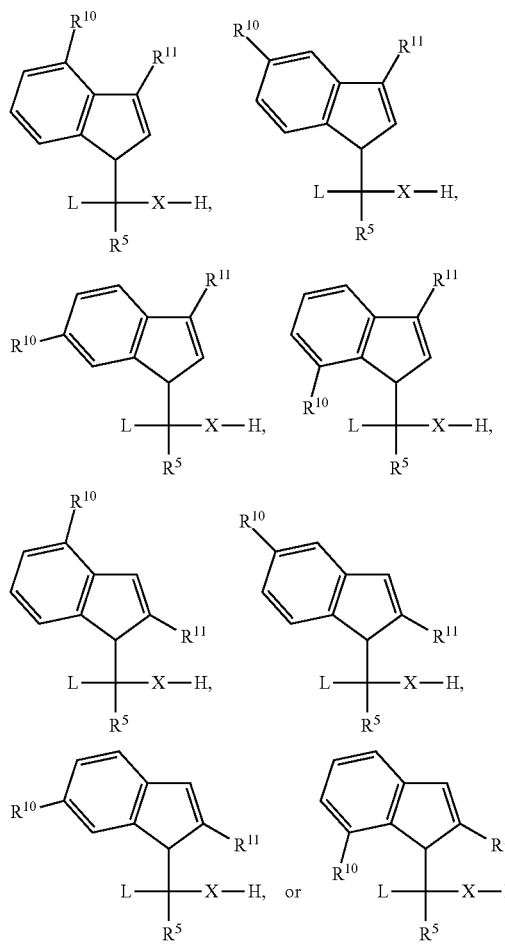

In more particular embodiments of the invention, the molecules of formula (1c) include

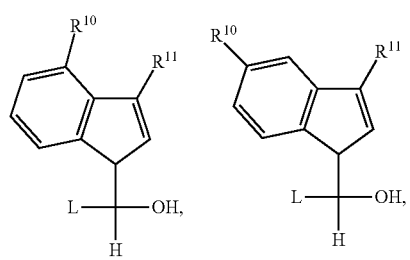

-continued

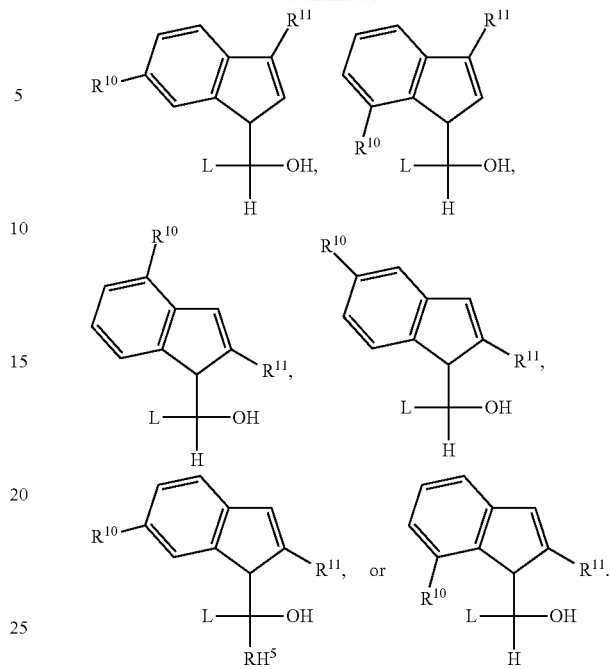

In a particular embodiment of the invention, the molecules of formula (1) have the more specific formula (1d)

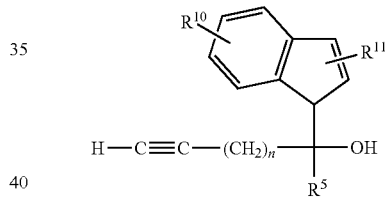

(1d)

wherein $R^{10}$ and $R^{11}$ are each independently H, an electron-donating group, or an electron-withdrawing group and wherein $R^{10}$ and $R^{11}$ may occur as non-hydrogen substituents at 1-4 or 1-2 positions in their respective rings, n=1-6, and $R^5$ is H or alkyl ($C_{1-6}$), for example,

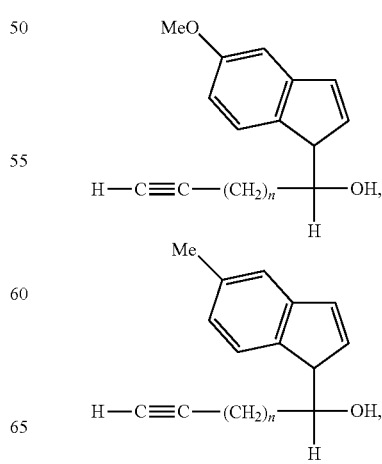

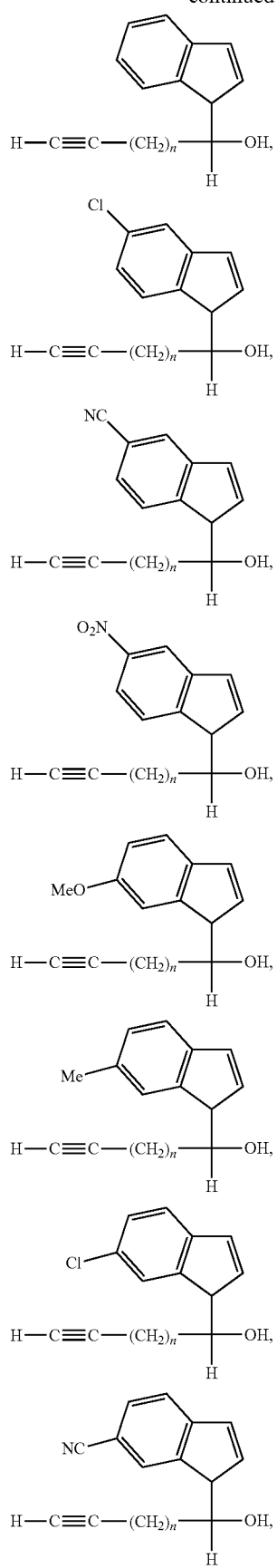
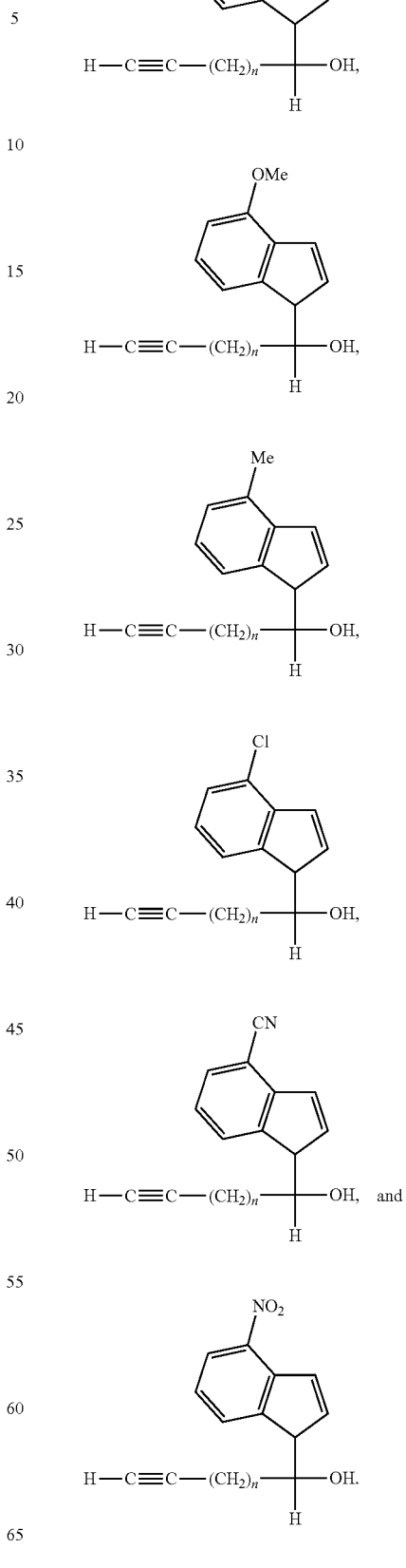

23
as well as
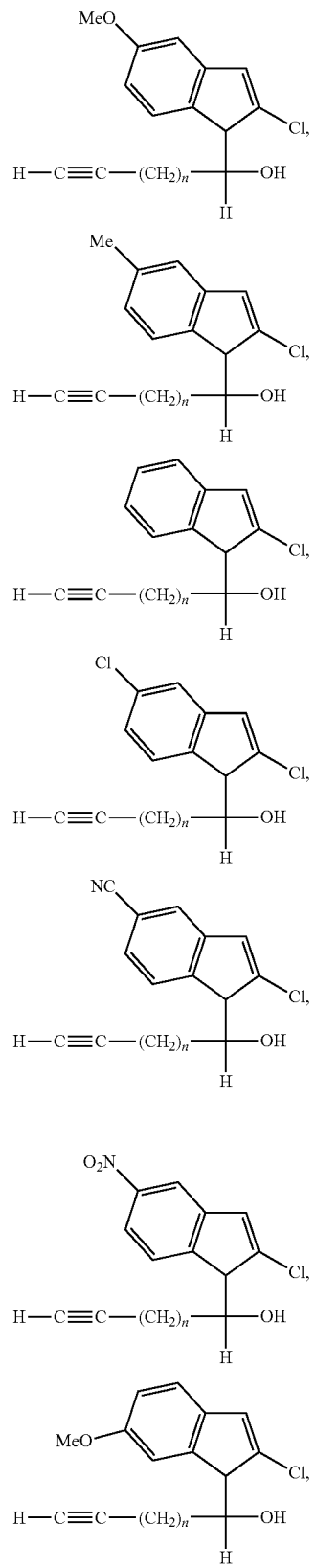
24
-continued
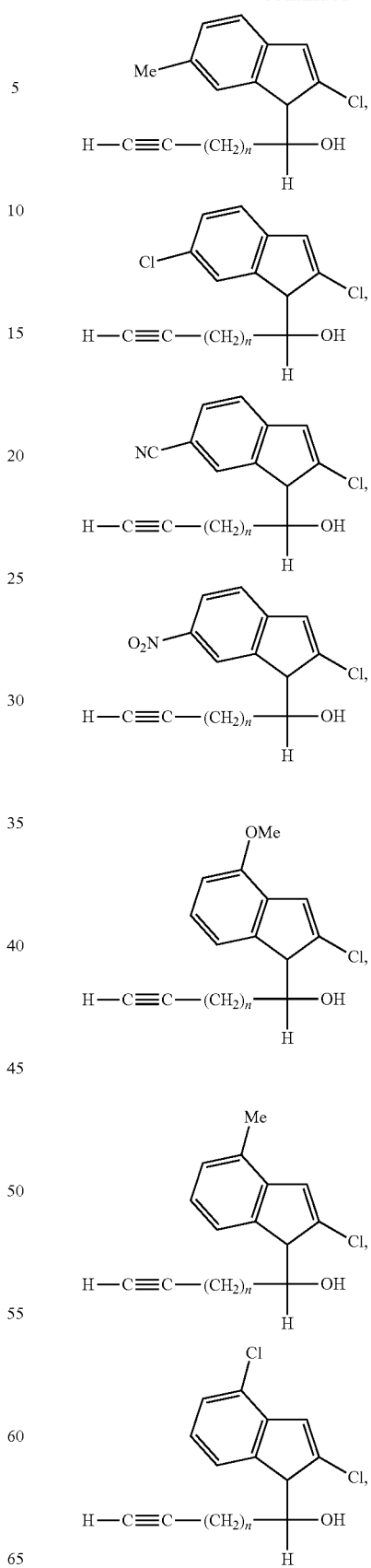

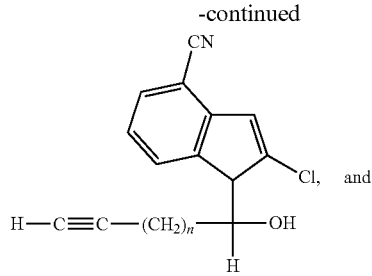

and

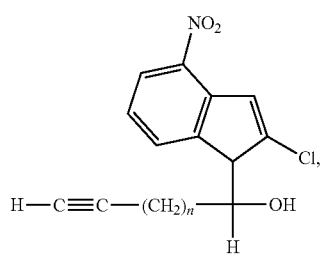

In certain embodiments, the molecules of the invention have the formula (1e)

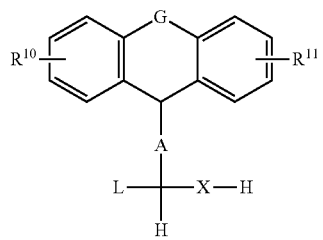

(1e)

wherein $R^{10}$ and $R^{11}$ are each independently H, an electron-donating group, or an electron-withdrawing group, wherein $R^{10}$ and $R^{11}$ may be non-hydrogen substituents at 1-4 positions of their respective rings; X is O or S; A is alkenyl ($C_2$), aryl, or absent; L is a linking group capable of being attached to a macromolecule; and G is a bond, C=O, O, SO, $SO_2$, $CX_2$, or $CX_2CX_2$, wherein each X is independently H or Cl, and $R^5$ is H or alkyl ($C_{1-6}$).

Examples include

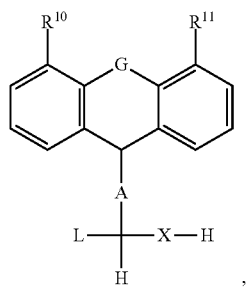

,

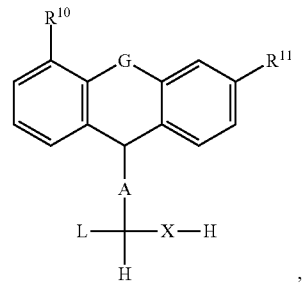

,

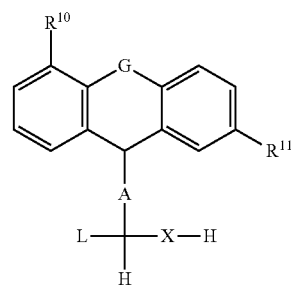

,

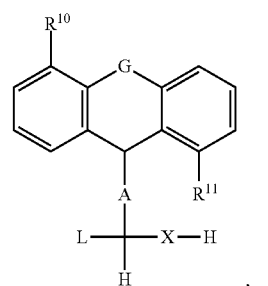

,

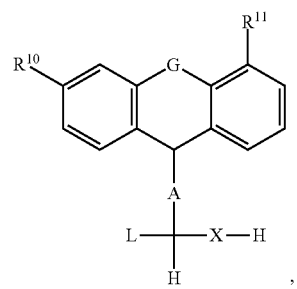

,

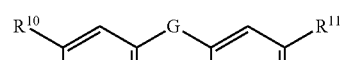

,

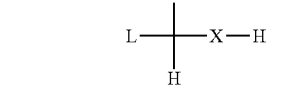

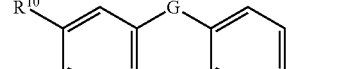

,

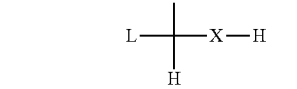

,

-continued
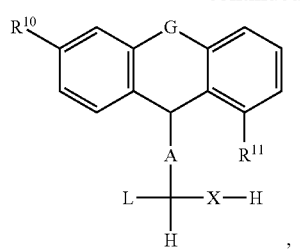,
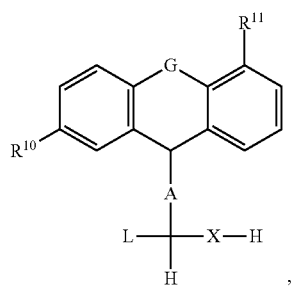,
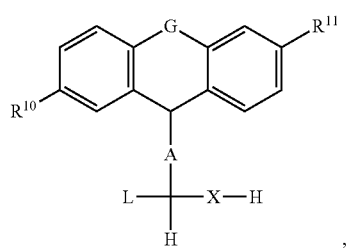,
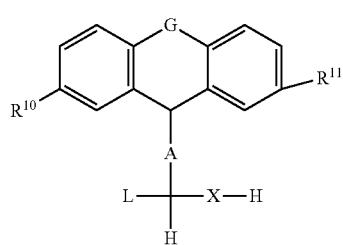,
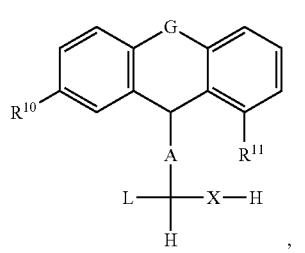,
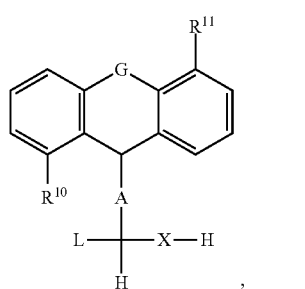,
-continued
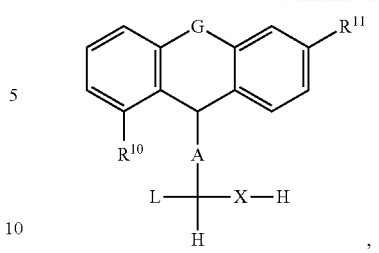,
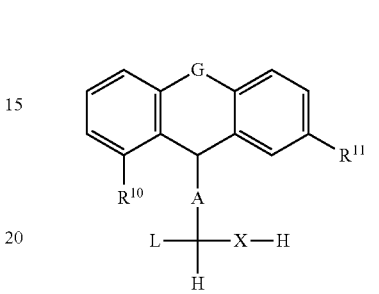
and
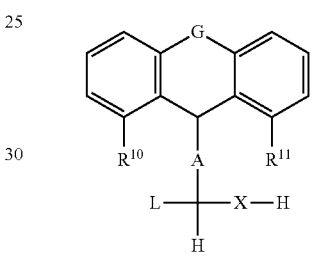,
as well as
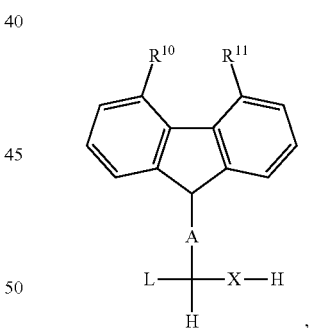,
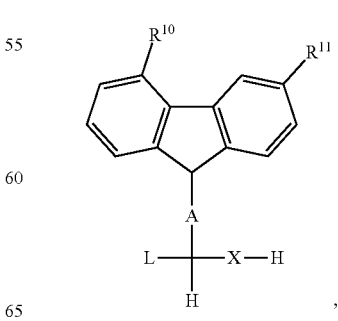,

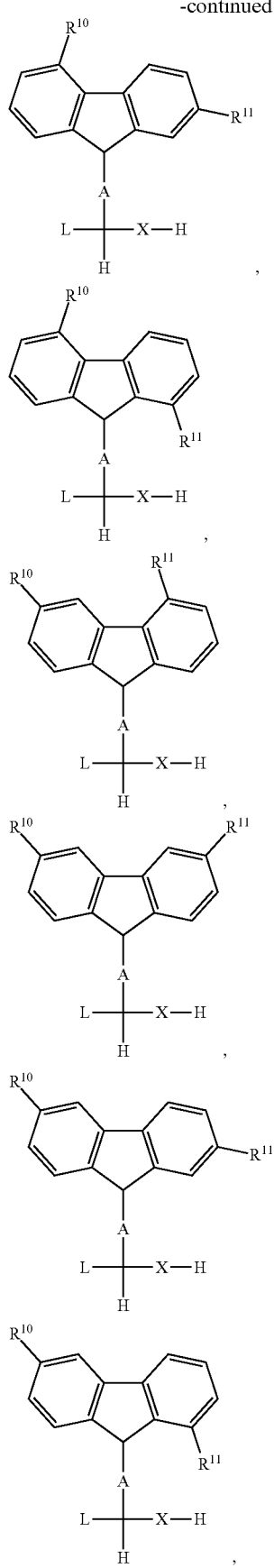
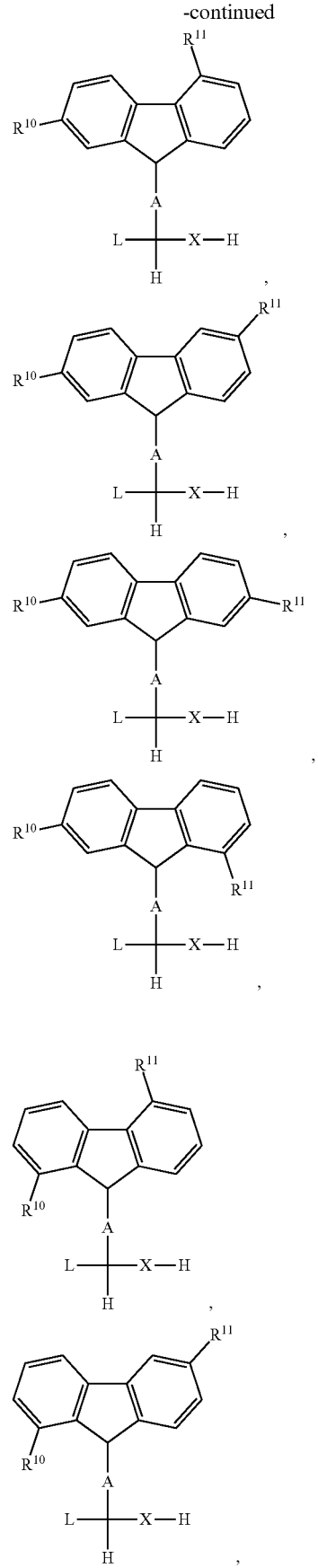

-continued

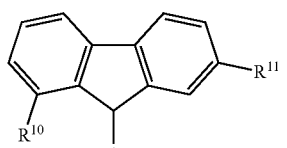, or

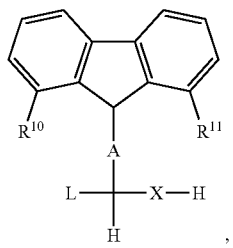, including

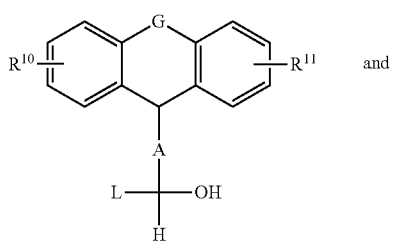 and

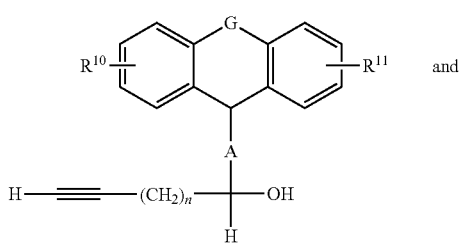 and

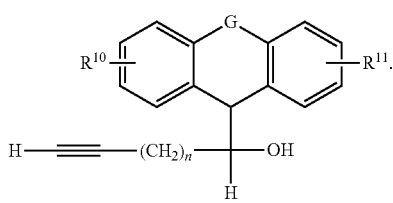.

In certain embodiments of the invention, the molecules of formula (1) have the more specific formula (1f)

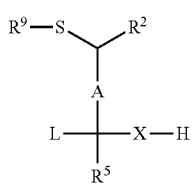 (1f)

-continued

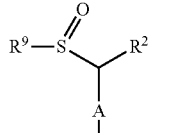

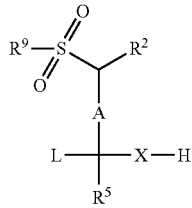

wherein $R^2$ is H, aryl, substituted aryl, heteroaryl, substituted heteroaryl, alkenyl, alkynyl, CN, NO$_2$, C(=O)—R$^3$, SOR$^3$; SO$_2$R$^3$, SR$^4$, X is O or S; A is alkenyl (C$_2$), aryl, or absent; L is a linking group capable of being attached to a macromolecule; R$^9$ is alkyl, substituted alkyl, aryl, substituted aryl, heteroaryl, substituted heteroaryl, alkenyl, or alkynyl, and R$^5$ is H or alkyl (C$_{1-6}$).

In one embodiment, $R^2$ is H. In another embodiment, $R^2$ is aryl, substituted aryl, heteroaryl, or substituted heteroaryl. In another embodiment, $R^2$ is CN.

Examples of formula (1f) wherein $R^{10}$ is H or an electron withdrawing or electron donating group include

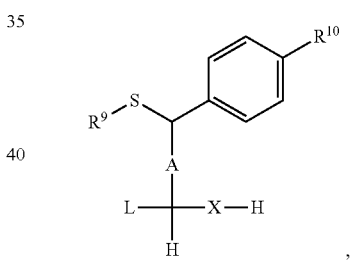,

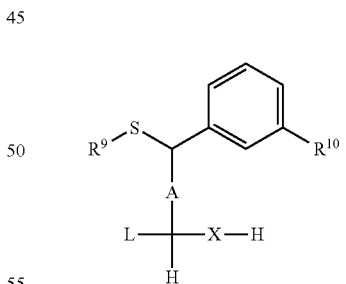,

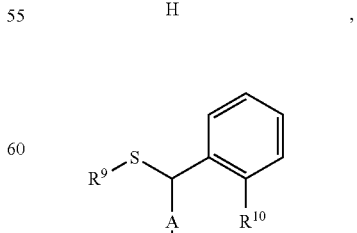,

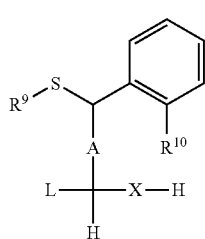,

-continued
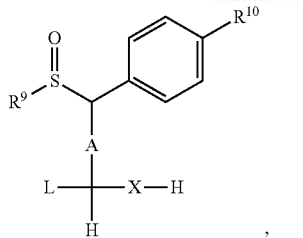
,
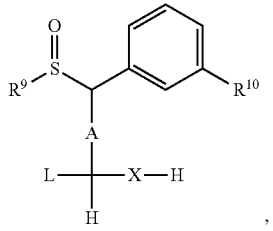
,
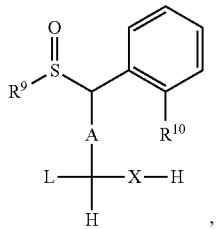
,
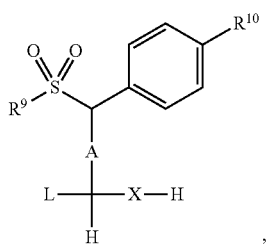
,
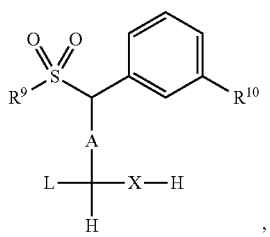
, or
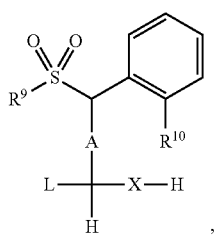
,
as well as
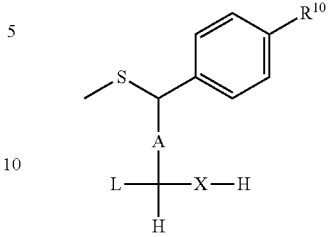
,
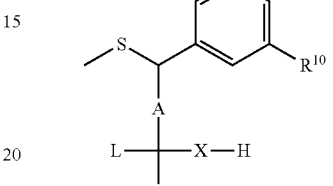 , 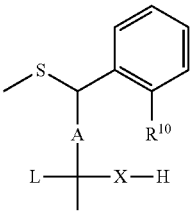 ,
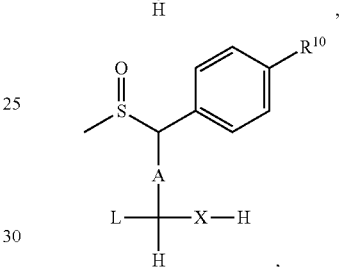 , 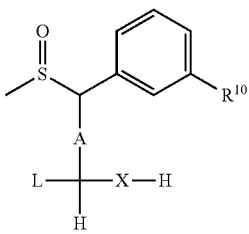 ,
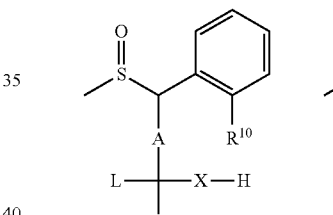 , 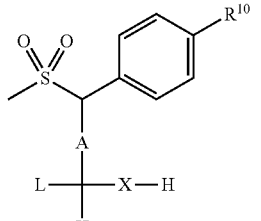 ,
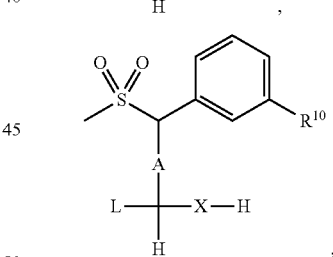 , or 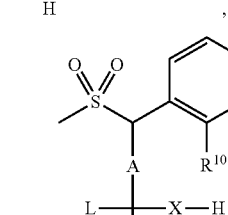 .
In even more particular embodiments of the invention, the molecules of formula (1f) include
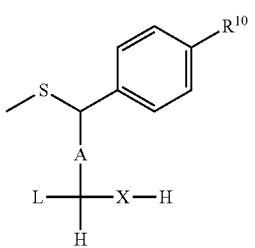 ,

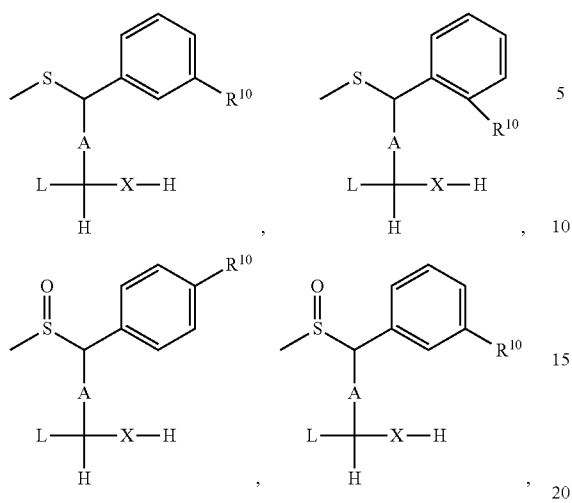

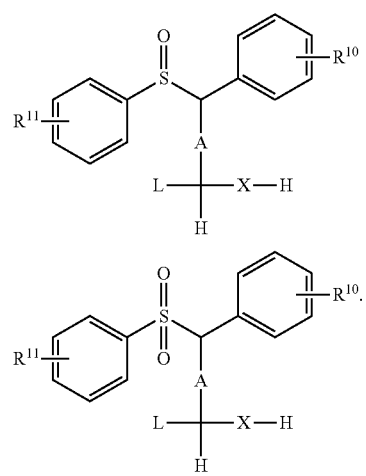

Although only one instance of substitution by $R^{10}$ is shown, $R^{10}$ as an electron-withdrawing or an electron-donating substituent may occur at 1-5 positions of the phenyl rings to which it is attached.

In one particular embodiment of the invention, the molecules of formulas (1f) wherein $R^{10}$ and $R^{11}$ is each independently H or an electron withdrawing or electron donating group, wherein $R^{10}$ and $R^{11}$ as non-hydrogen substituents may be present at 1-5 positions of their respective phenyl rings have formula

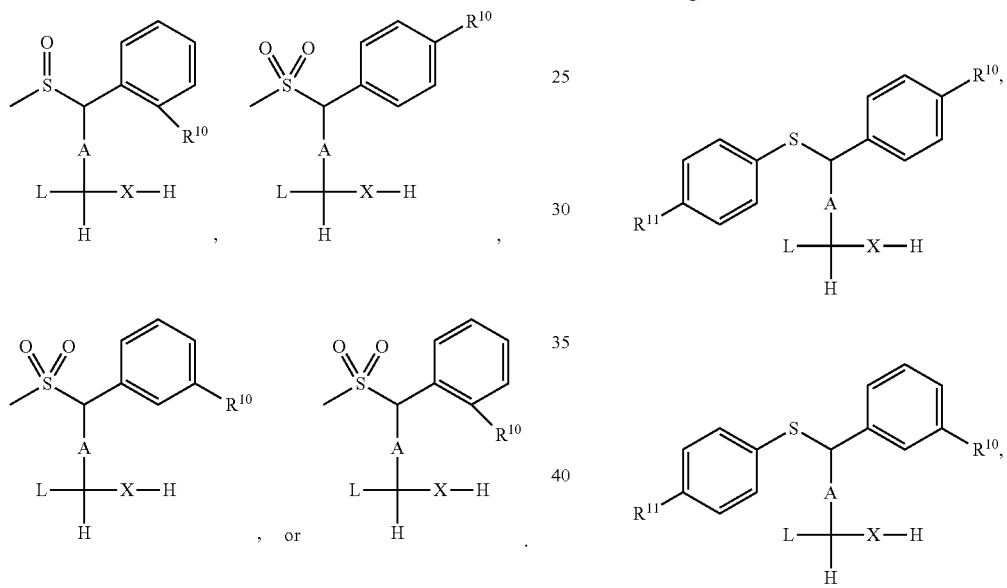

including

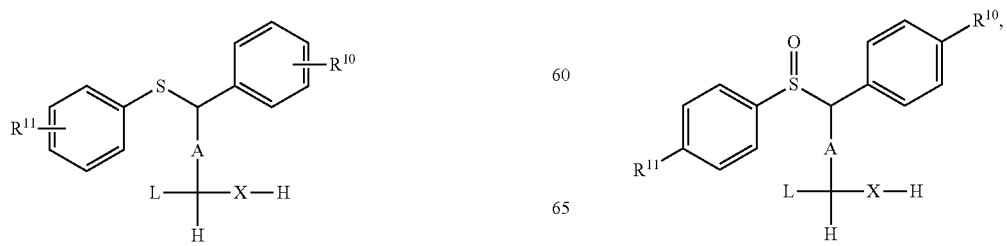

-continued
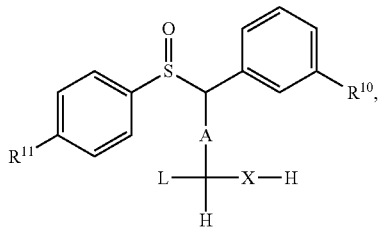
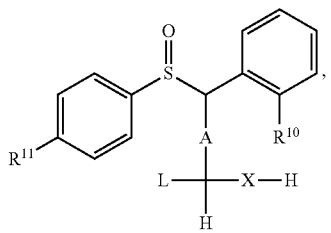
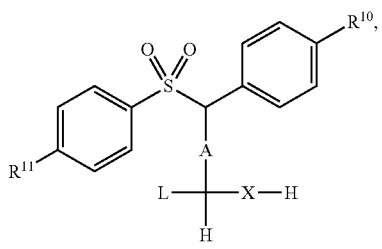
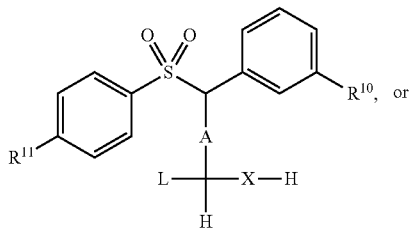
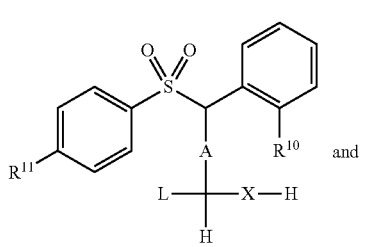 and
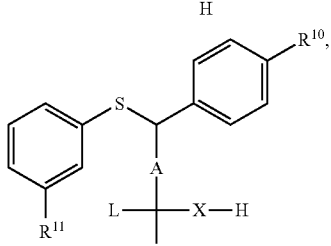
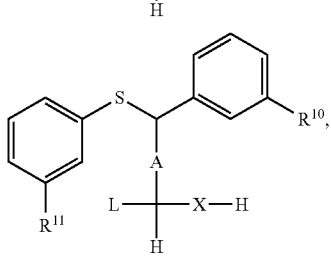
-continued
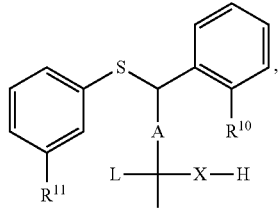
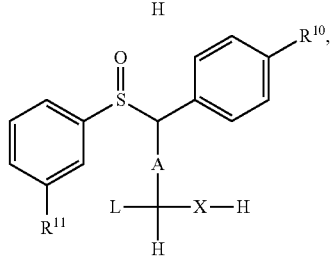
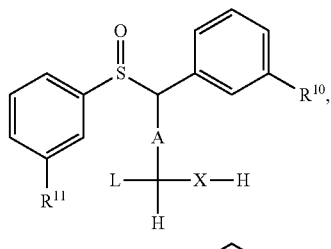
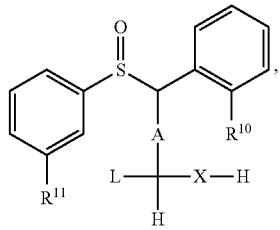
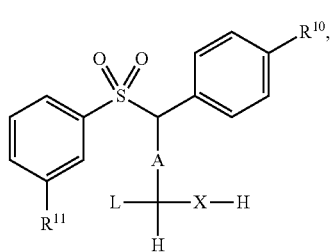
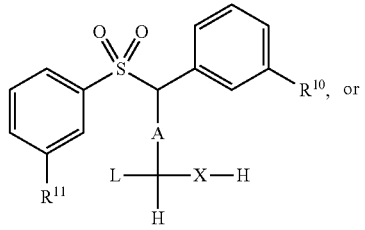 or
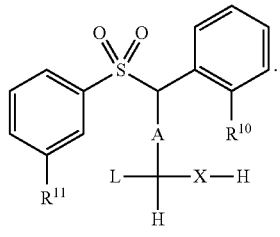

In another more particular embodiment, the compounds of the invention have the formula

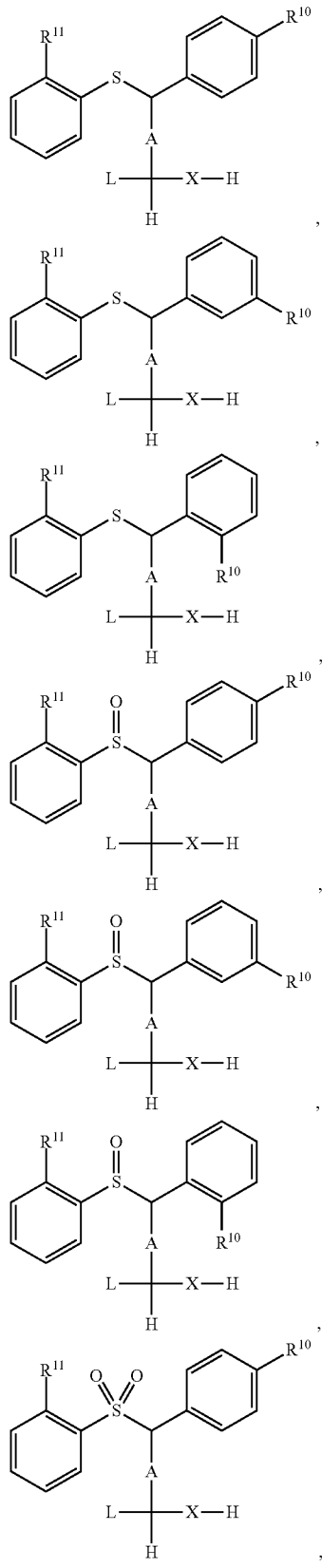

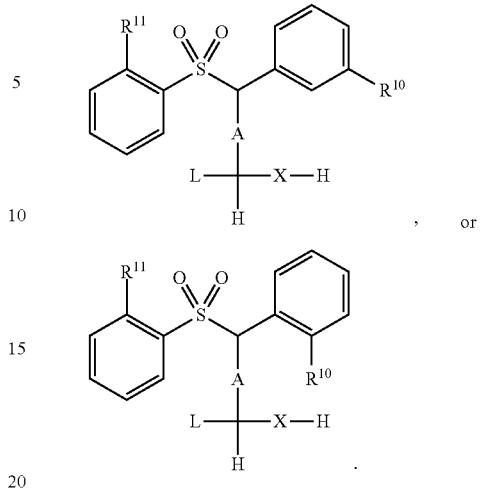

In certain embodiments of the invention, the molecules of formula (1) have the more specific formula (1g)

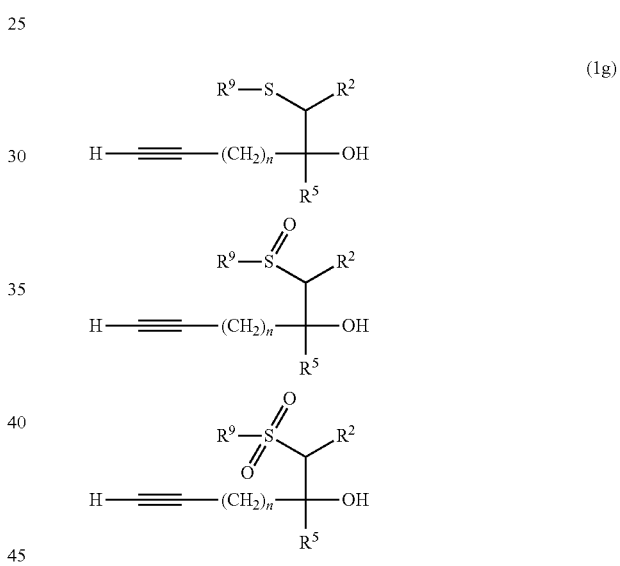

wherein $R^2$ is H, aryl, substituted aryl, heteroaryl, substituted heteroaryl, alkenyl, alkynyl, CN, $NO_2$, C(O)—$R^3$, $SOR^3$, $SO_2R^3$, or $SR^4$; $R^9$ is alkyl, substituted alkyl, aryl, substituted aryl, heteroaryl, substituted heteroaryl, alkenyl, or alkynyl; n=1-6, and $R^5$ is H or alkyl ($C_{1-6}$).

Molecules of formula (1g) wherein $R^{10}$ is H or an electron withdrawing or electron donating group include

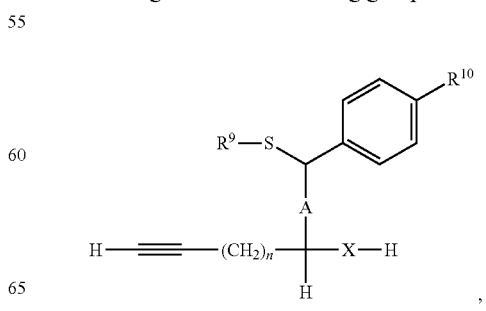

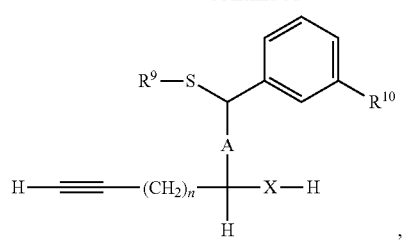
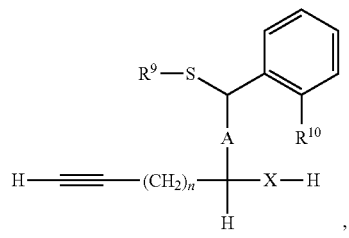
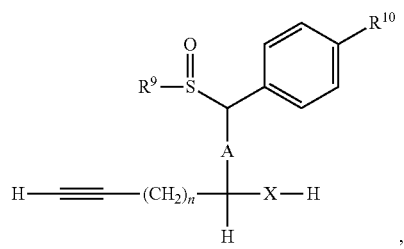
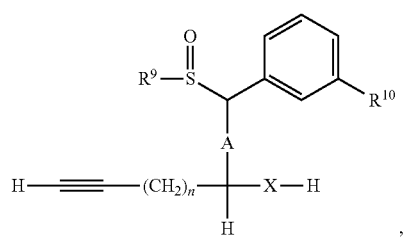
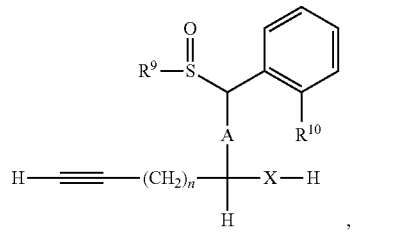
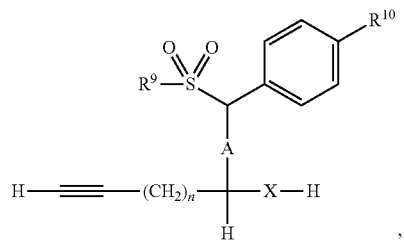
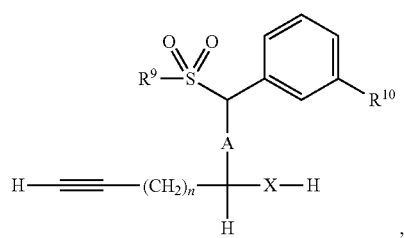
, and
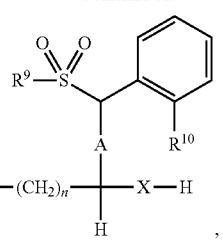
,
as well as
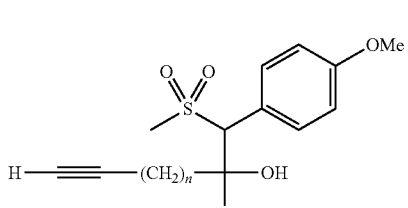
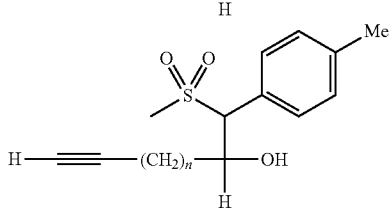
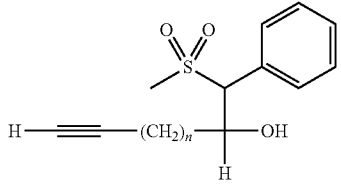
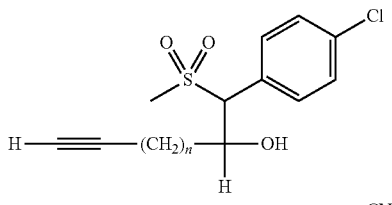
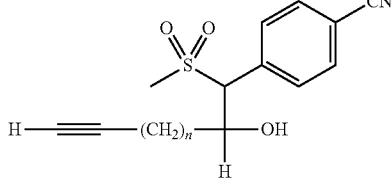
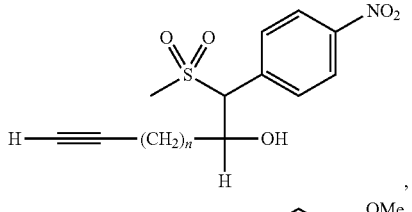
, and
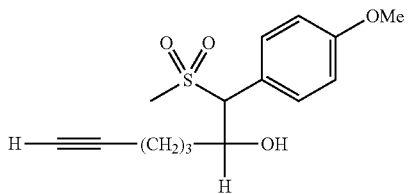

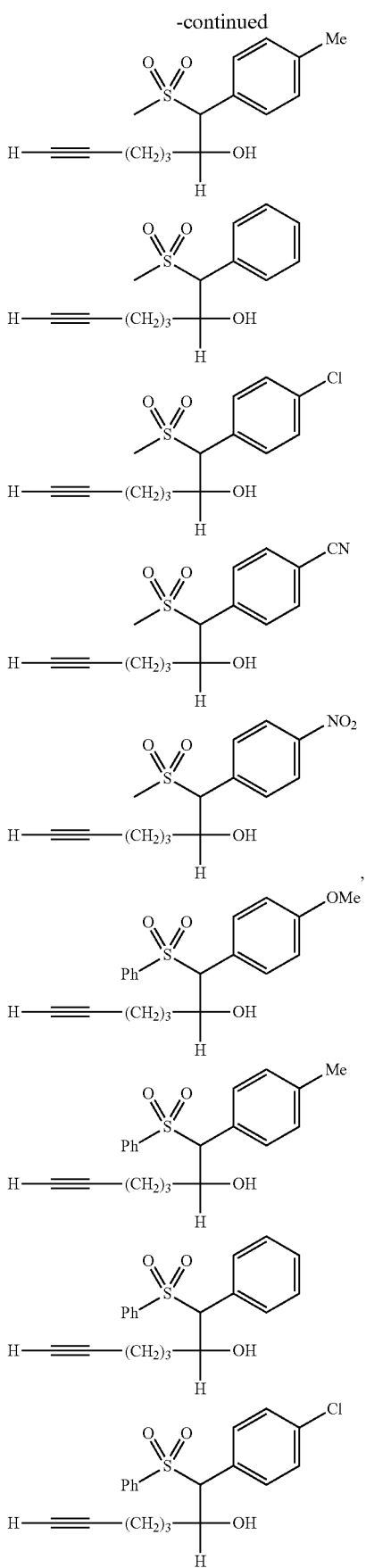

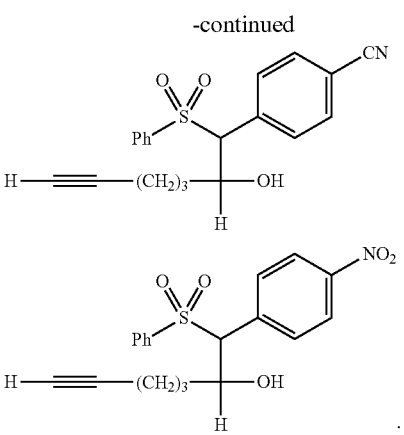

Although R[10] as a non-hydrogen substituent has been shown in only one position, such non-hydrogen substituent can be present at 1-5 positions on the phenyl moiety shown.

In certain embodiments of the invention, the molecules of formula (1) have the more specific formula (1h)

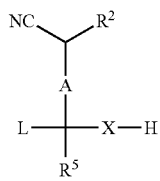

(1h)

wherein R[2] is H, aryl, substituted aryl, heteroaryl, substituted heteroaryl, alkenyl, alkynyl, CN, NO$_2$, C(=O)—R[3], SOR[3], SO$_2$R[3] or SR[4]; X is O or S; A is alkenyl (C$_2$), aryl, or absent; L is a linking group capable of being attached to a macromolecule, and R[5] is H or alkyl (C$_{1-6}$).

In one embodiment, R[2] is H. In another embodiment, R[2] is aryl, substituted aryl, heteroaryl, or substituted heteroaryl.

Molecules of formula (1h) include

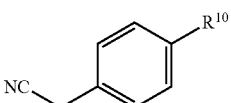

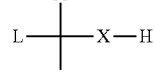

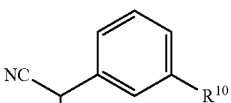

, or

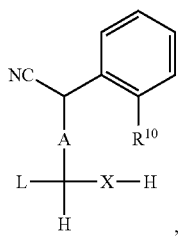
wherein $R^{10}$ is H, an electron-withdrawing group, or an electron-donating group. Although $R^{10}$ is specifically shown at only one position in the phenyl rings above, a non-hydrogen embodiment of $R^{10}$ may be present in 1-5 positions, preferably 3 or less positions on the phenyl ring.
Molecules of formula (1h) also include
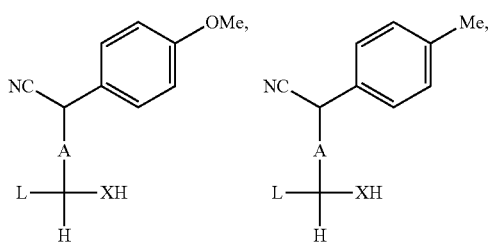
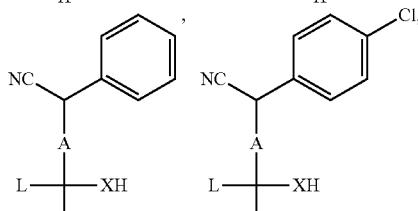
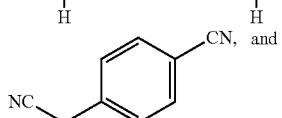
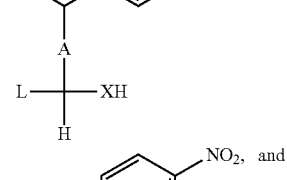
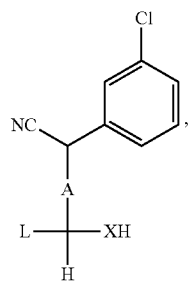
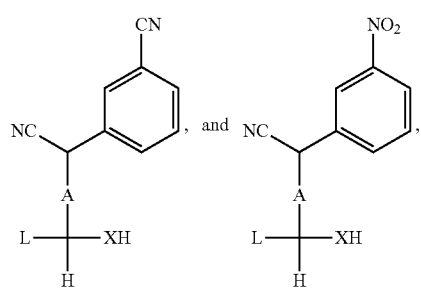
as well as
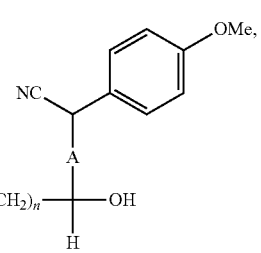
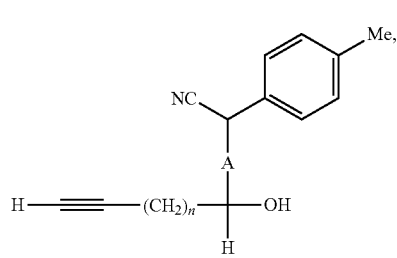
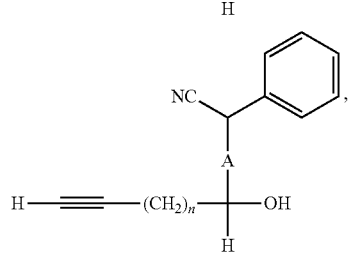
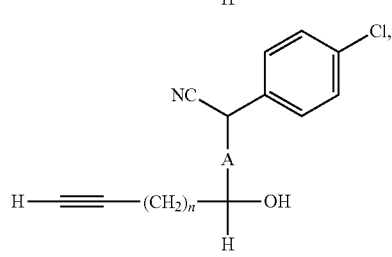
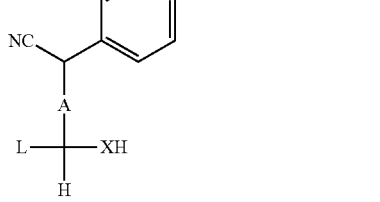
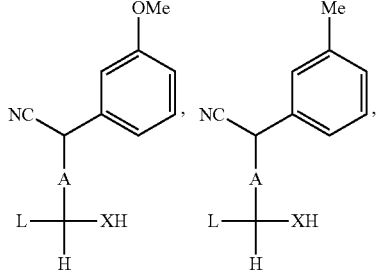

-continued

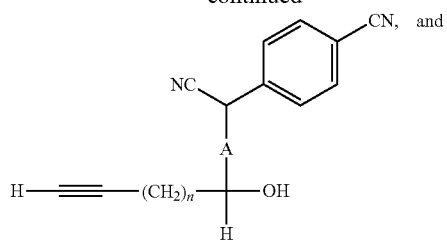

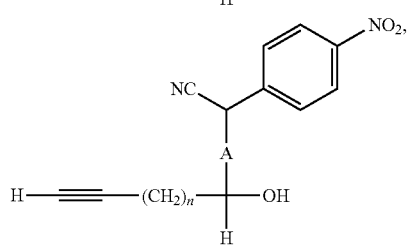

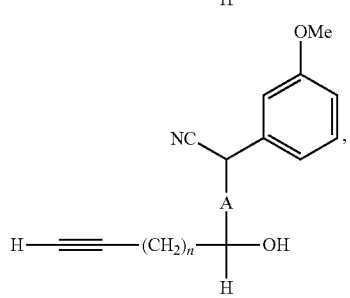

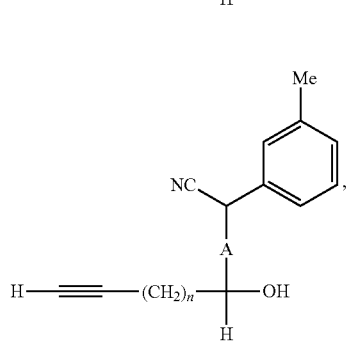

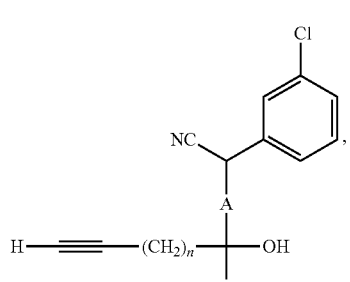

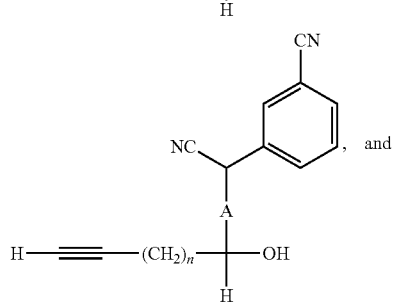

-continued

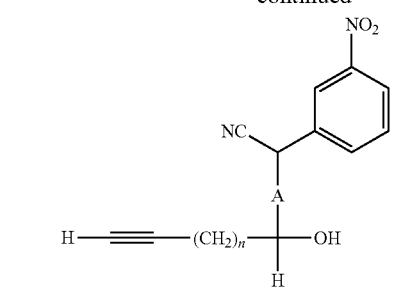

wherein n=1-6.

In certain embodiments of the invention, the molecules of formula (1) have the more specific formula (1k)

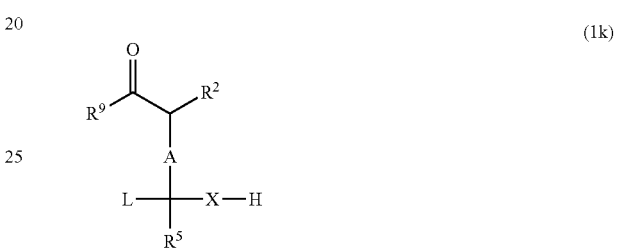

(1k)

wherein $R^2$ is H, aryl, substituted aryl, heteroaryl, substituted heteroaryl, alkenyl, alkynyl, CN, $NO_2$, C(=O)—$R^3$, $SOR^3$, $SO_2R^3$ or $SR^4$; X is O or S; A is alkenyl ($C_2$), aryl, or absent; and L is a linking group capable of being attached to a macromolecule, and $R^5$ is H or alkyl ($C_{1-6}$).

In a particular embodiment of the invention, the molecules of formula (1k) have $R^2$=H, giving molecules of formula (1m), wherein $R^{11}$ is H or an electron withdrawing or electron donating group, wherein $R^{11}$ as a non-hydrogen substituent may be present at 1-5 positions, preferably less than 3 positions on the phenyl moiety.

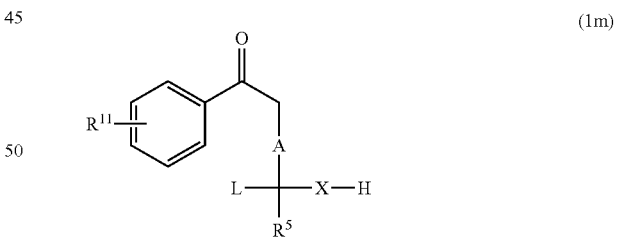

(1m)

Molecules of formula (1m) include

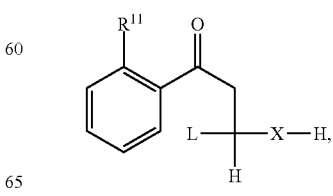

-continued
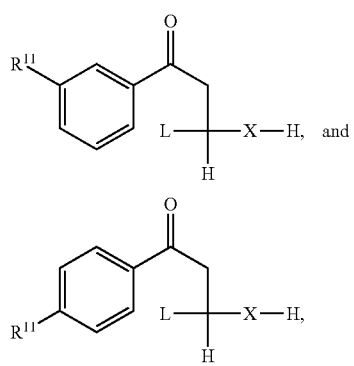
as well as
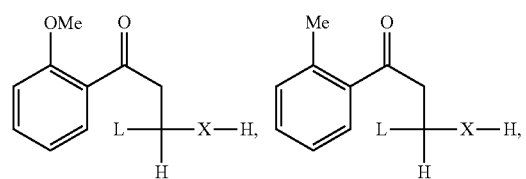
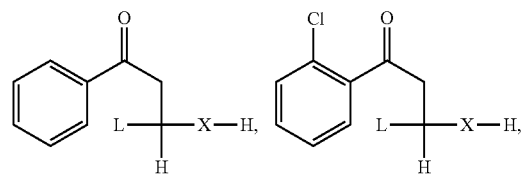
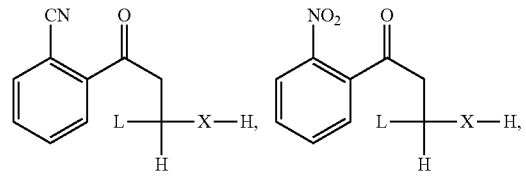
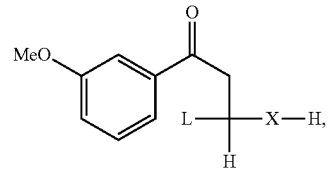
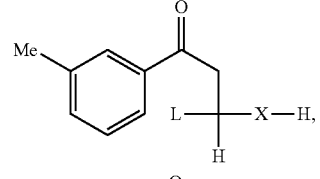
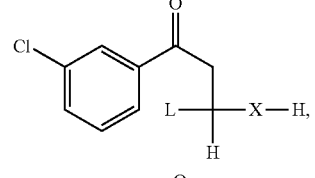
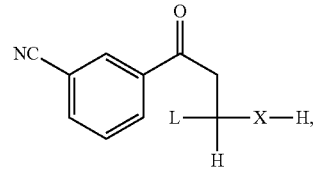
-continued
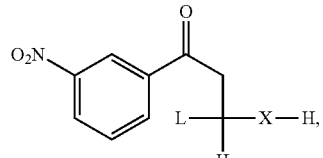
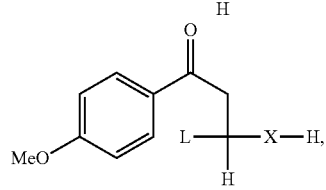
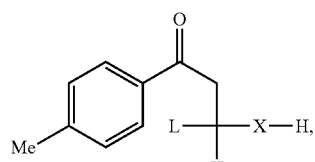
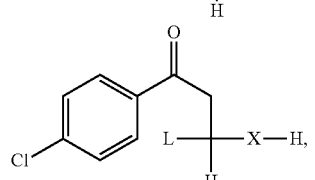
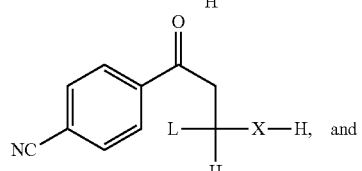
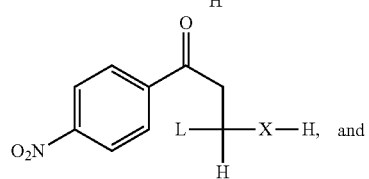
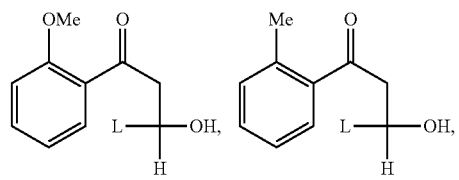
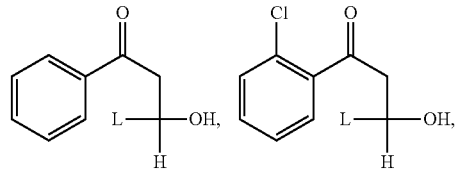
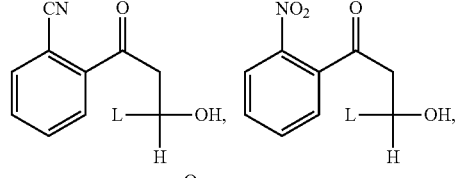
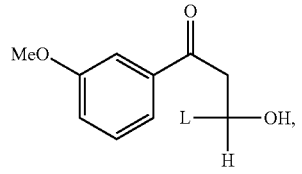

-continued

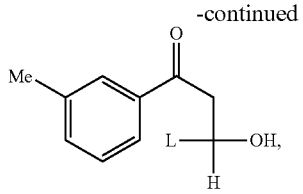
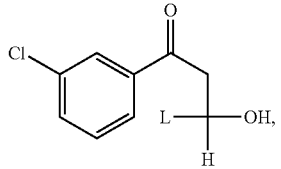
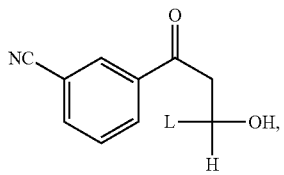
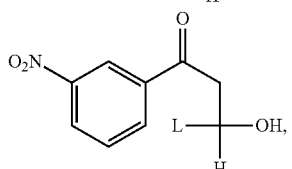
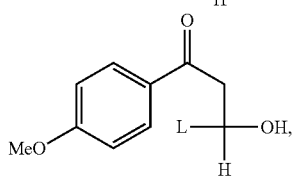
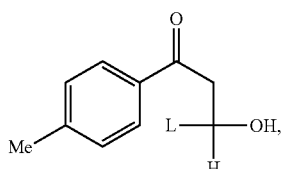
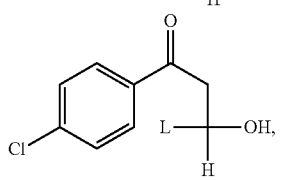
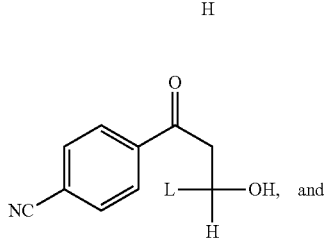
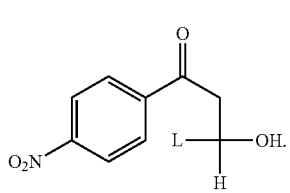

In a particular embodiment of the invention, the molecules of formula (1m) have the formula (1n)

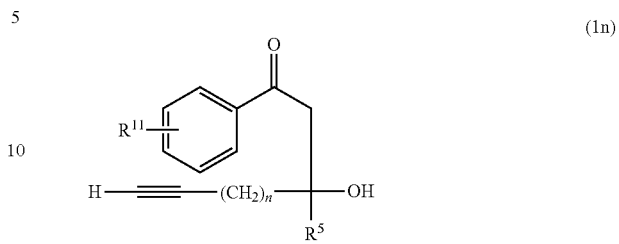

(1n)

wherein n=1-6; $R^{11}$ is H, an electron-withdrawing group, or an electron-donating group wherein $R^{11}$ as a non-hydrogen substituent may be present at 1-5 positions, preferably less than 3 positions on the phenyl moiety, and $R^5$ is H or alkyl ($C_{1-6}$).

Molecules of formula (1n) include

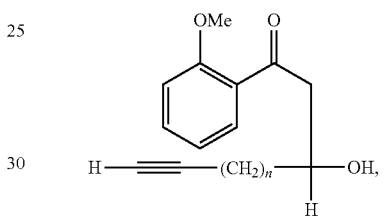
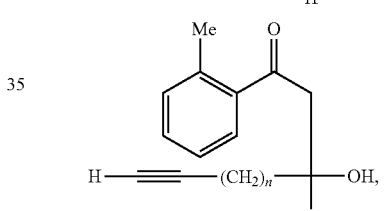
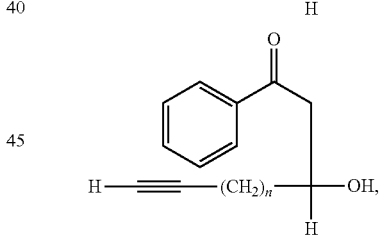
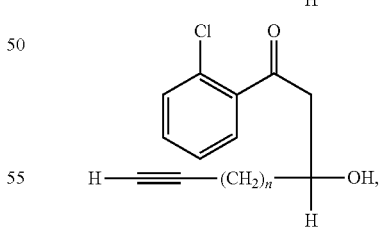
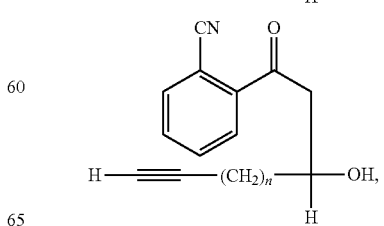

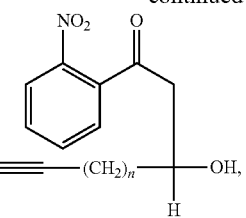
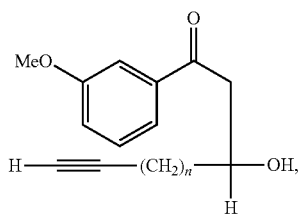
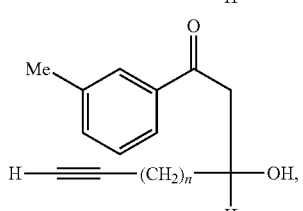
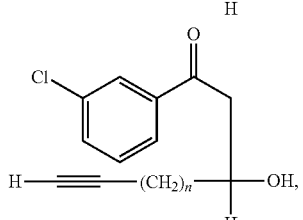
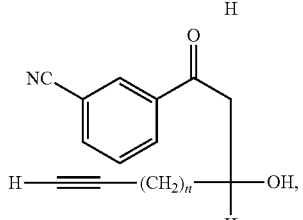
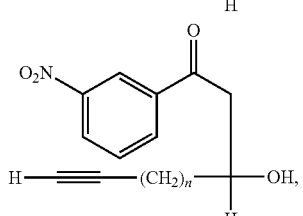
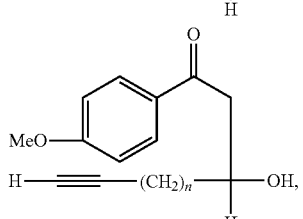
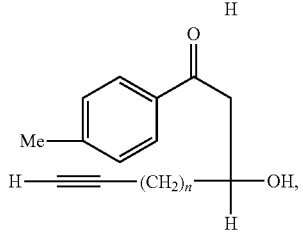

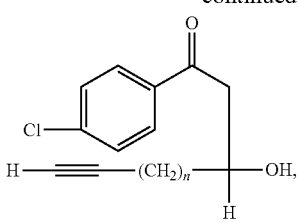
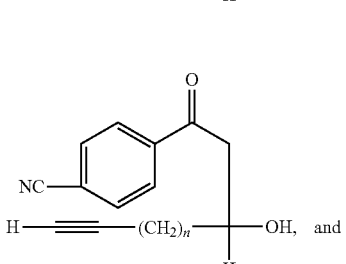
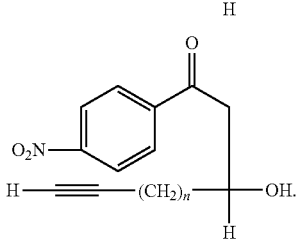

In a particular embodiment of the invention, the molecules of formula (1k) have $R^2$=aryl, and have the formula (1p)

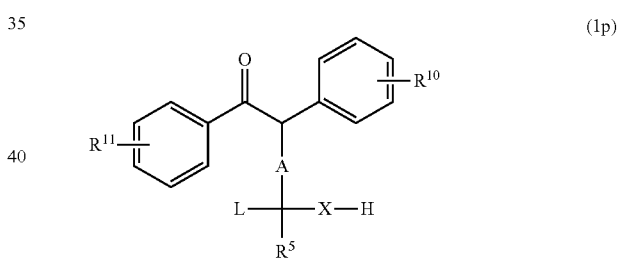

(1p)

wherein X is O or S; A is alkenyl ($C_2$), aryl, or absent; L is a linking group capable of being attached to a macromolecule; $R^{10}$ and $R^{11}$ are each independently H, an electron-withdrawing group, or an electron-donating group, wherein a non-hydrogen form of $R^{10}$ and $R^{11}$ may be present at 1-5 positions, preferably 3 or less positions of the phenyl moiety, and $R^5$ is H or alkyl ($C_{1-6}$).

Molecules of formula (1p) include

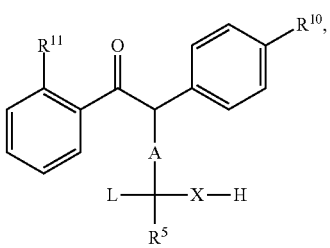

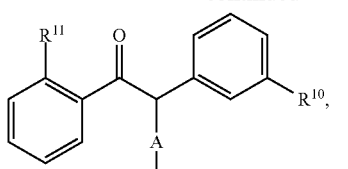

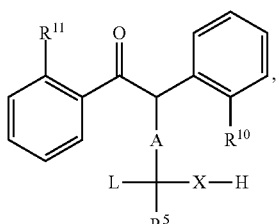

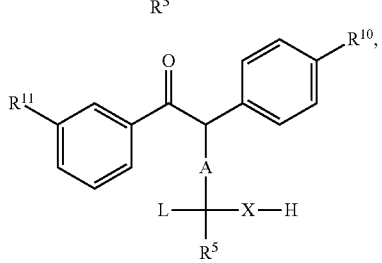

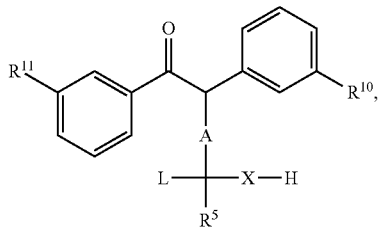

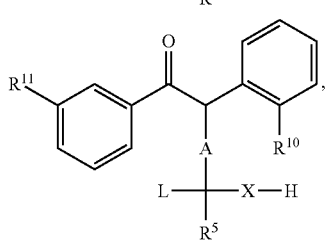

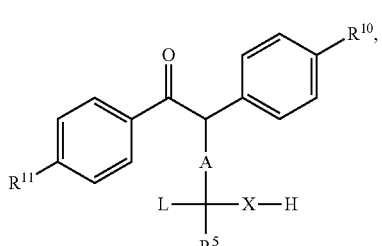

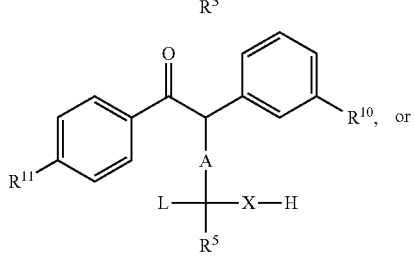

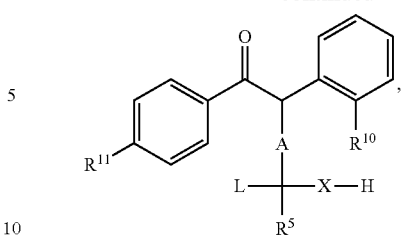

as well as

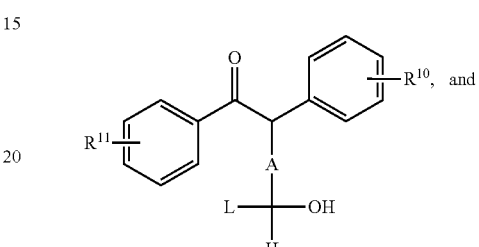

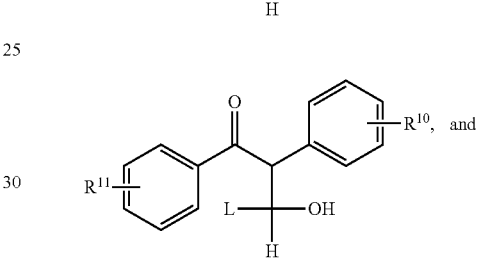

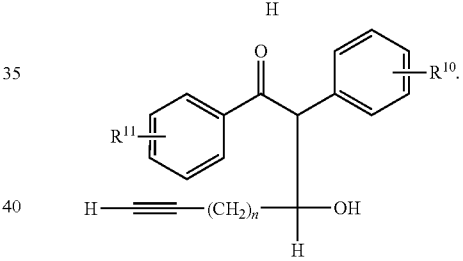

In a particular embodiment of the invention, the molecules of formula (1) have the more specific formula (1q)

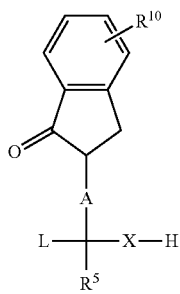

(1q)

wherein X is O or S; A is alkenyl ($C_2$), aryl, or absent; L is a linking group capable of being attached to a macromolecule; $R^{10}$ is H, an electron-withdrawing group, or an electron-donating group, wherein a non-hydrogen form of $R^{10}$ may be present at 1-4 positions, preferably 2 or less positions of the ring to which it is bound, and $R^5$ is H or alkyl ($C_{1-6}$).

Molecules of formula (1q) include
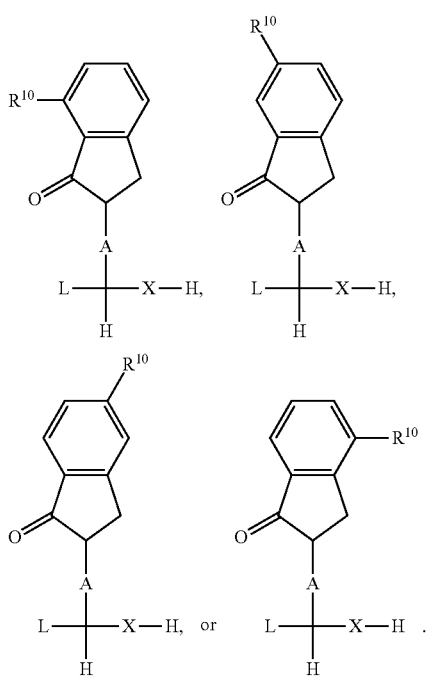
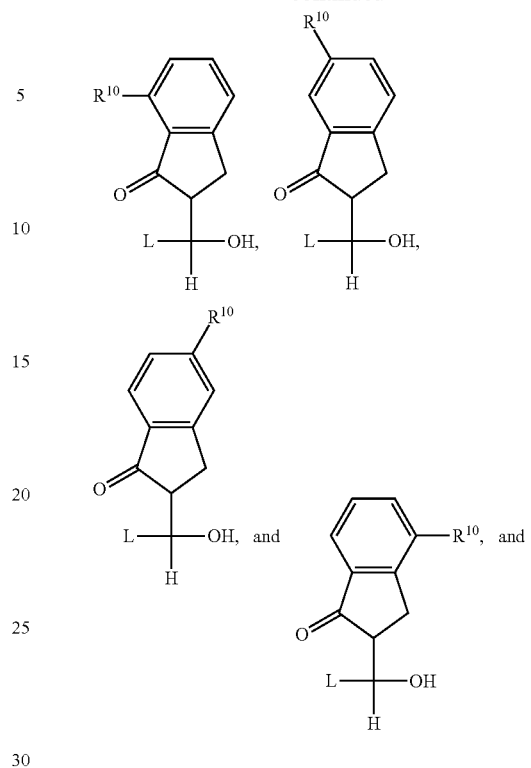
Molecules of formula (1q) include
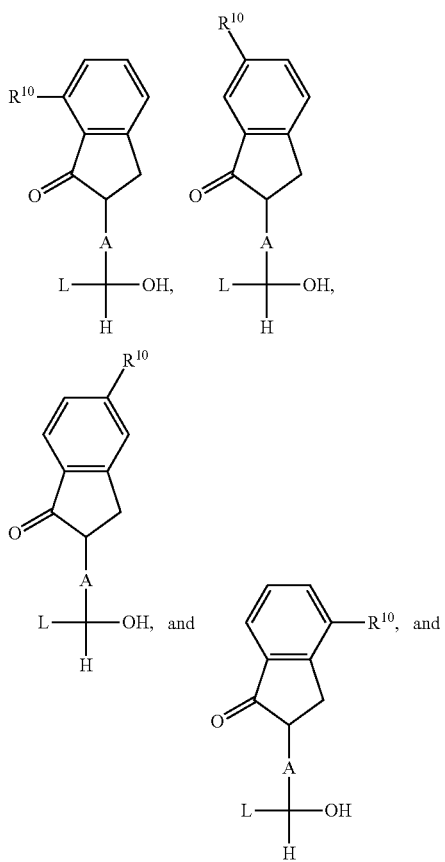
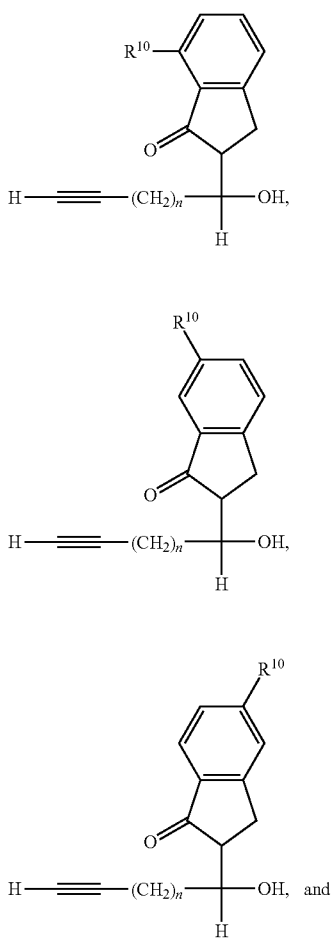

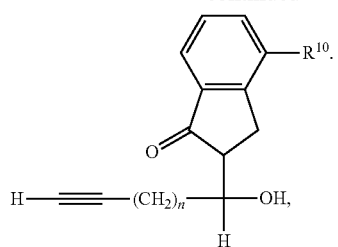
Molecules of formula (1q) also include
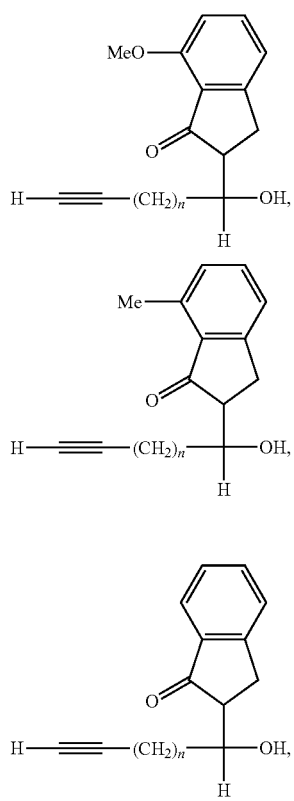
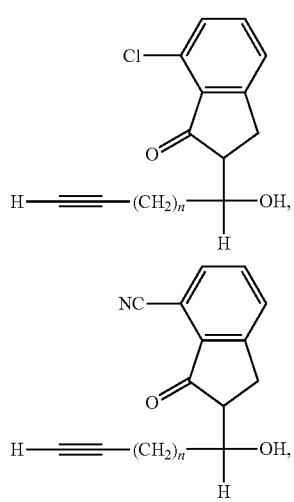
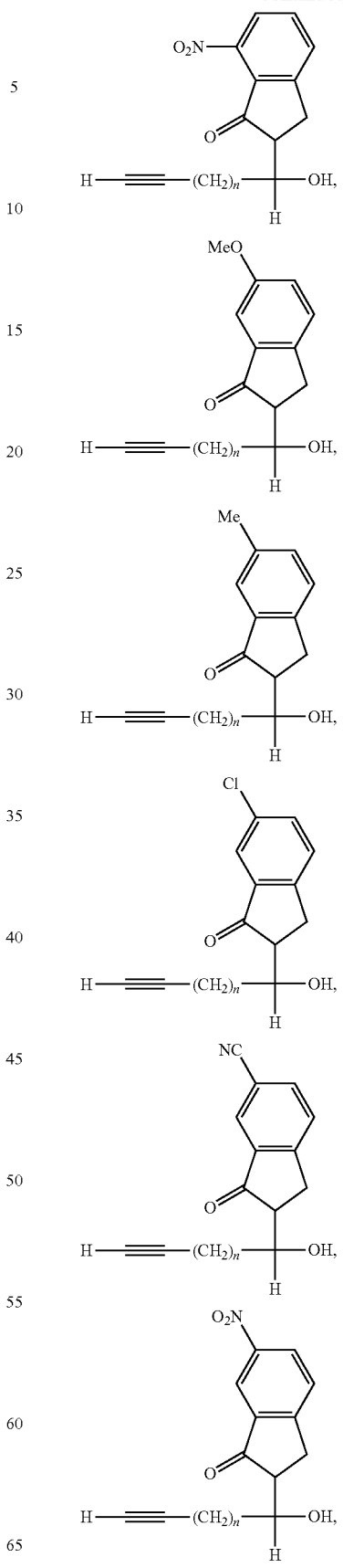

-continued
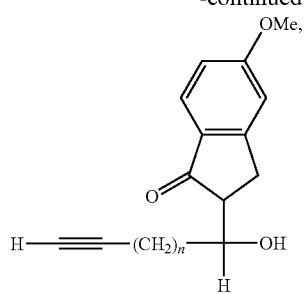
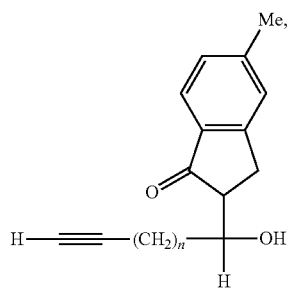
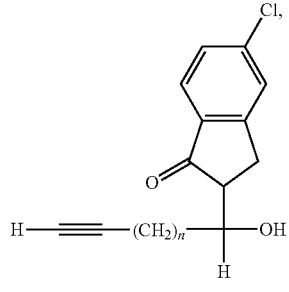
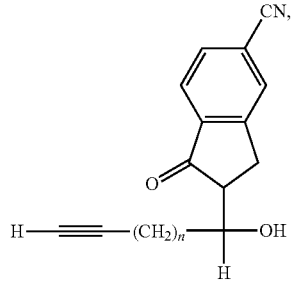
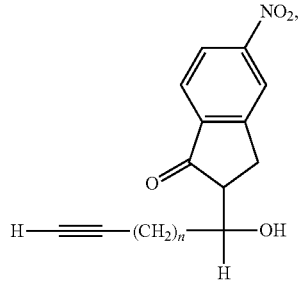
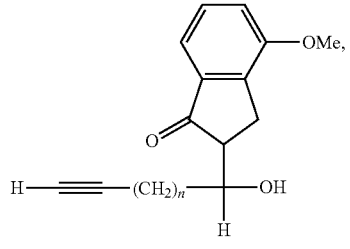
-continued
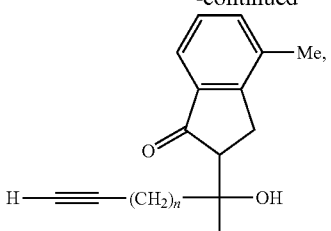
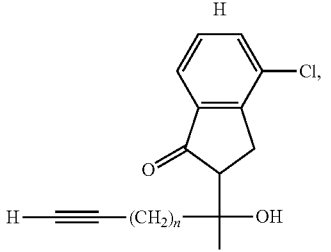
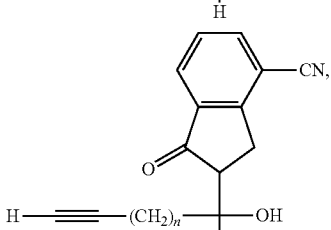
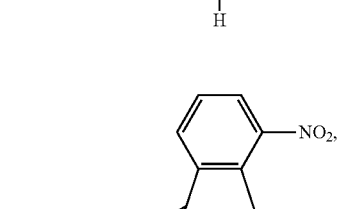
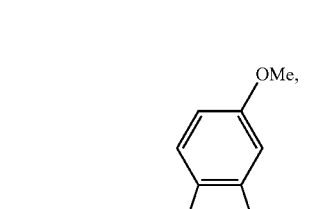
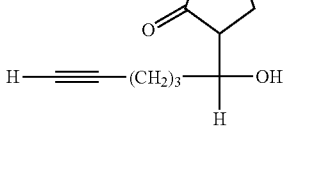
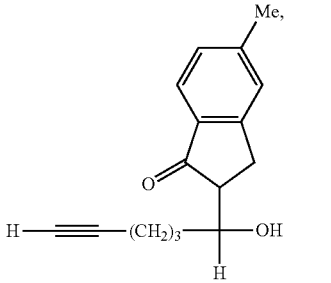

-continued

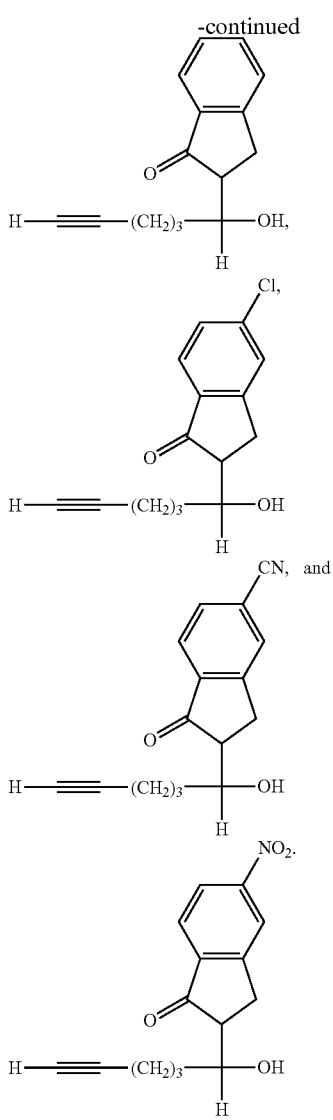

L is a linking group capable of being attached to a macromolecule. By the term "linking group capable of being attached to a macromolecule" is meant a group comprising a functionality through which L can be chemically bonded to a macromolecule. Examples of suitable functionality include but are not limited to amines, alcohols, thiols, chlorides, iodides, bromides, azides, maleimides, alkenes, alkynes, aldehydes, carboxylates, and phosphates. Thus, in one embodiment, L is $(CH_2)_nR^{12}$,

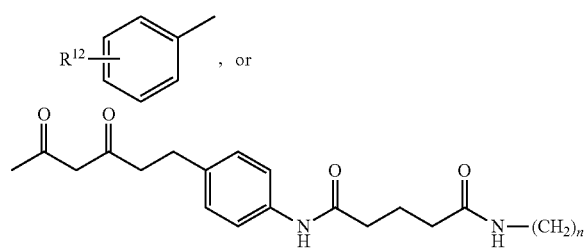

wherein n=1-6 and $R^{12}$ is $NH_2$, $N_3$, Cl, Br, I, SH, COOH, CHO, $CH=CH_2$, CCH, or maleimido.

In a particular embodiment, L is $(CH_2)_nR^{12}$, wherein n=1-6, and $R^{12}$ is $NH_2$, $N_3$, I, SH, COOH, CHO, CCH, or maleimido, or $R^{12}$ is $N_3$, SH, CHO, CCH, or maleimido, or $R^{12}$ is $N_3$ or CCH.

In certain embodiments, L is $(CH_2)_nCCH$, giving compounds of the invention having the formula

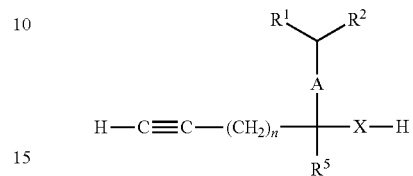

wherein X, $R^1$, $R^2$, $R^5$, A and X are as defined above.

Exemplary molecules of formula (1) thus have the formula

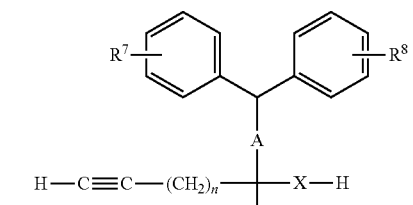

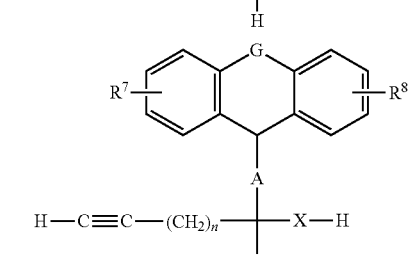

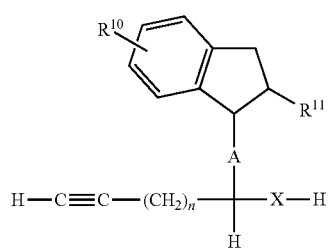

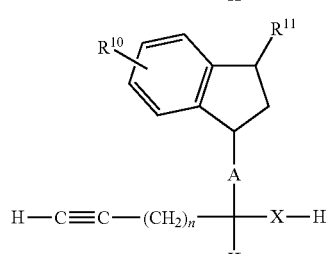

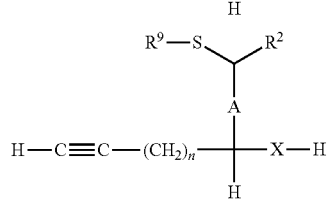

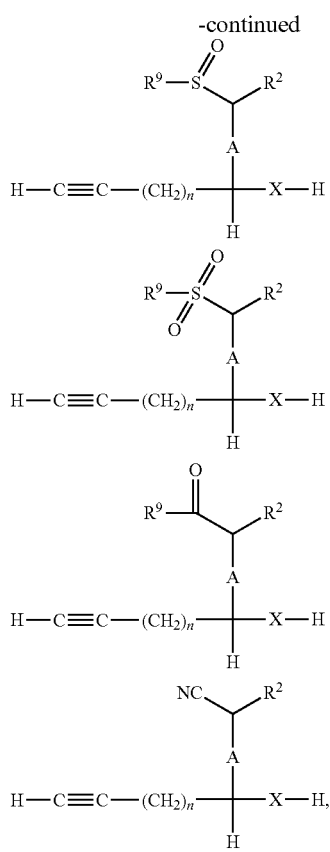
such as
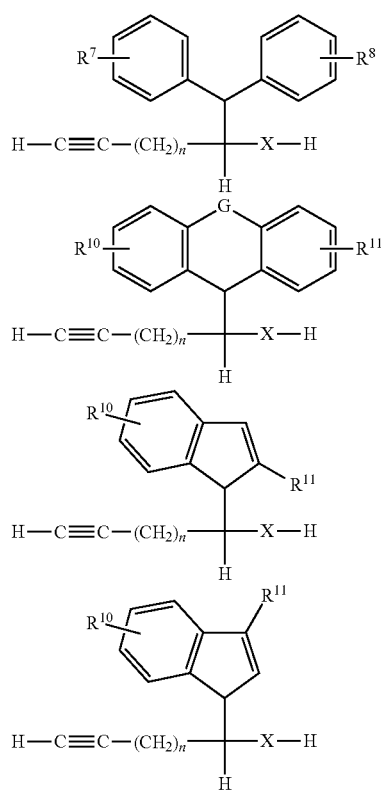
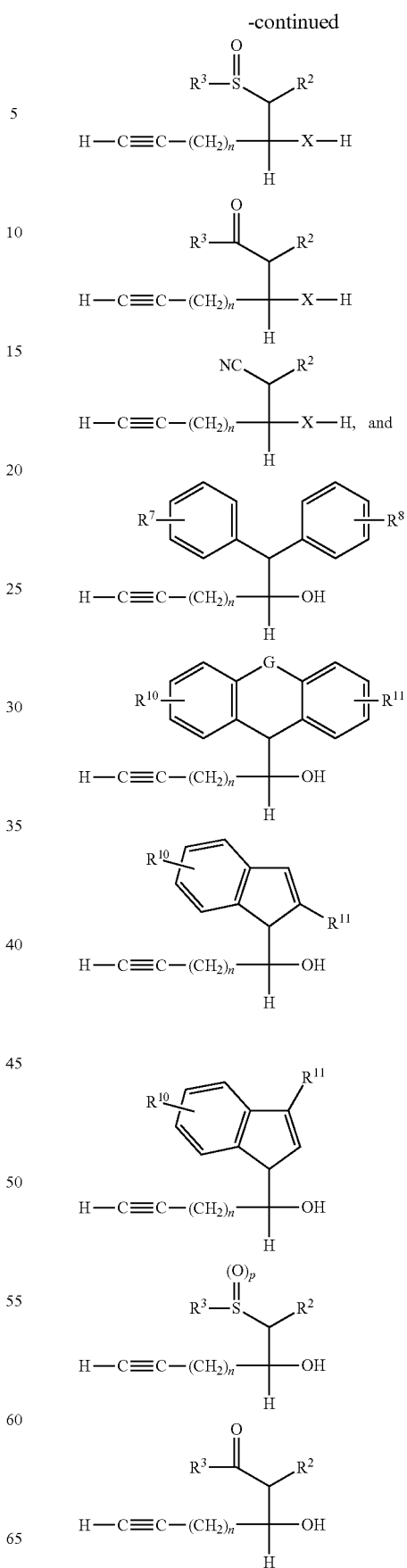

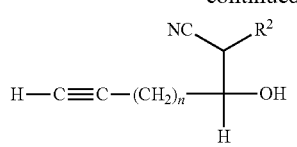
In more particular embodiments, the molecules of formula (1) include
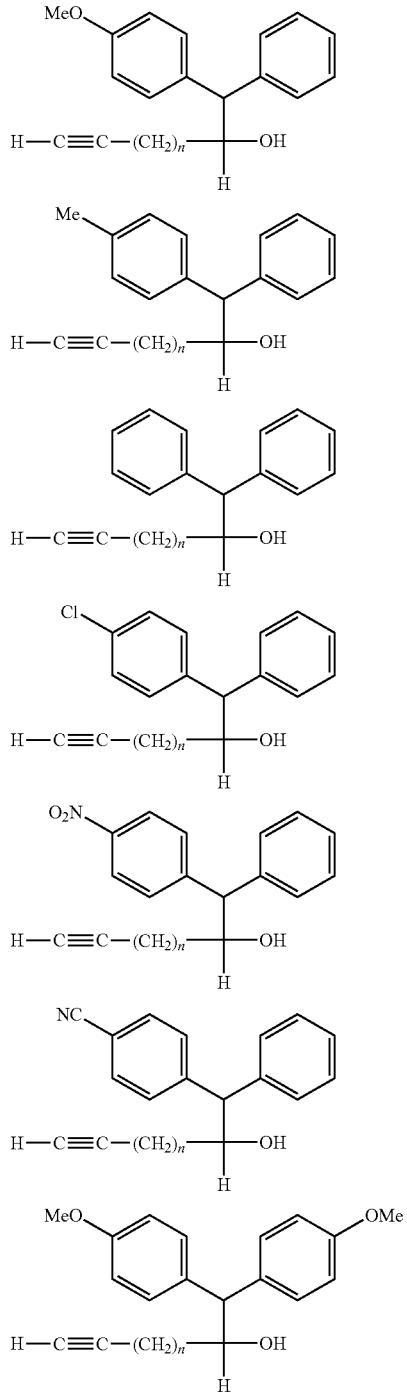
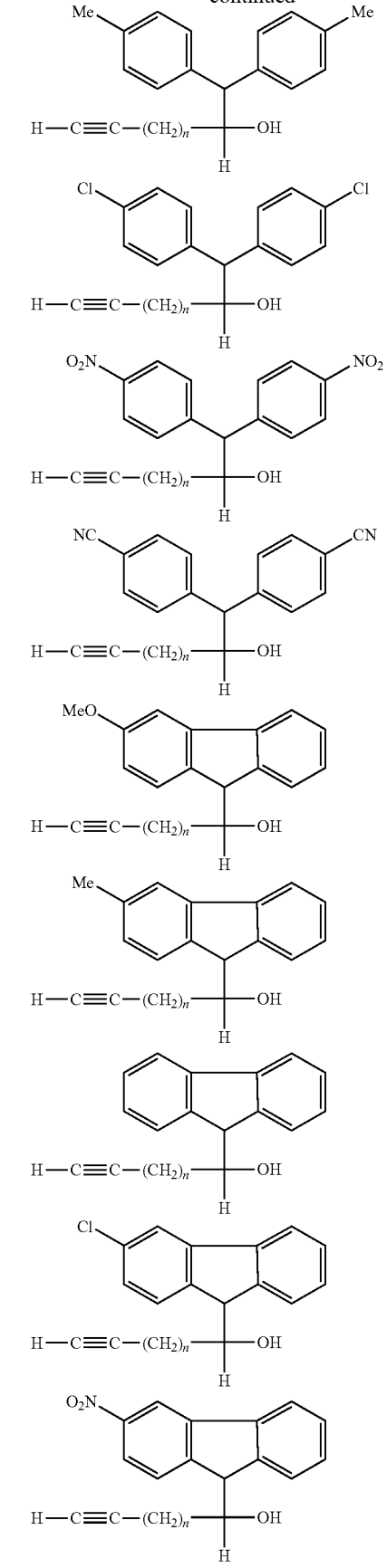

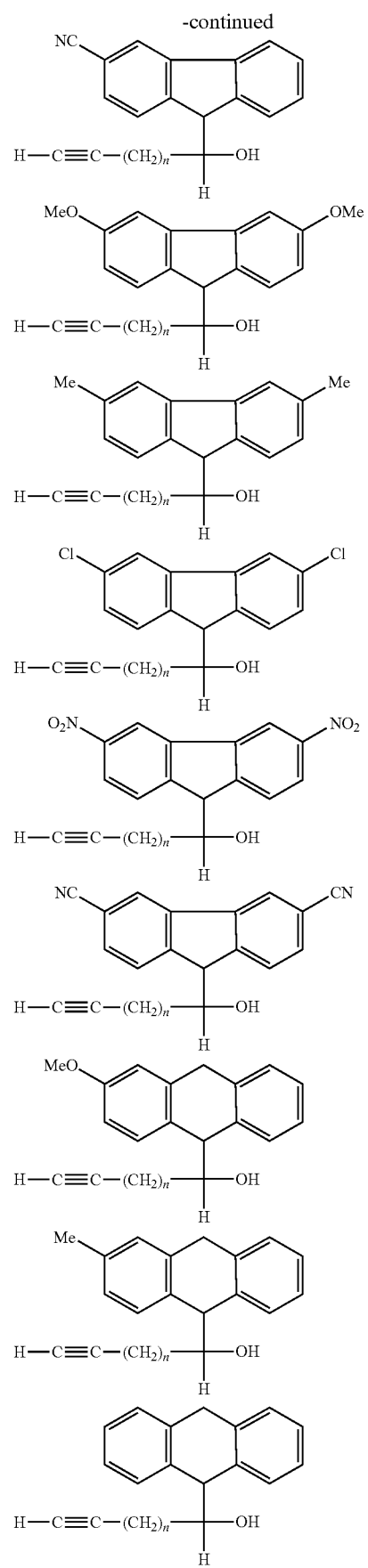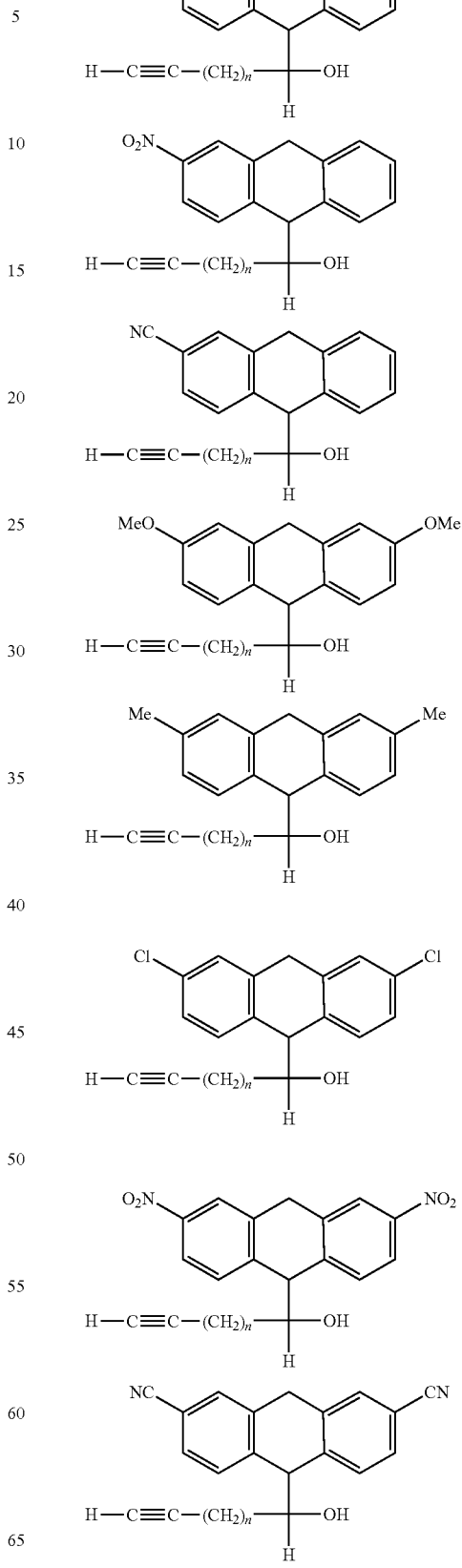

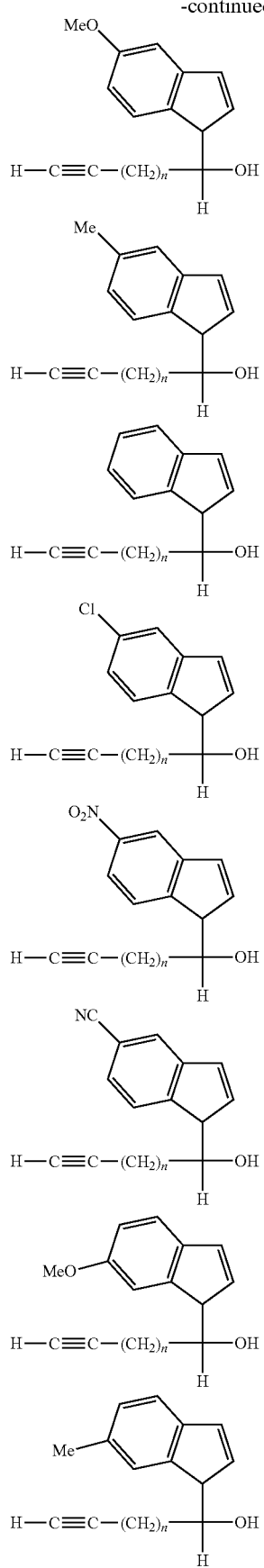
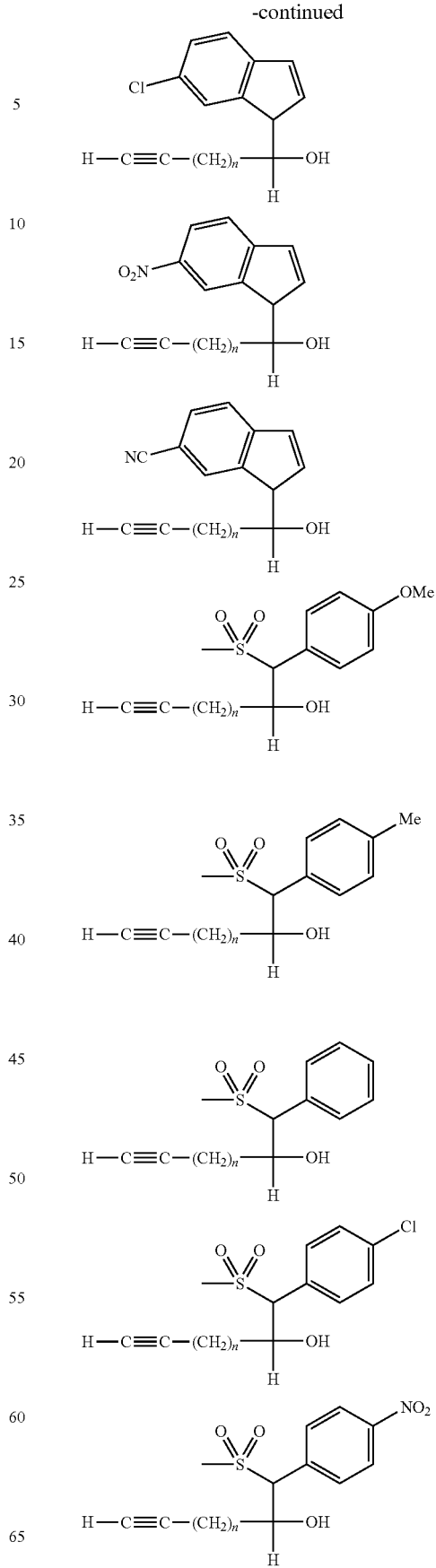

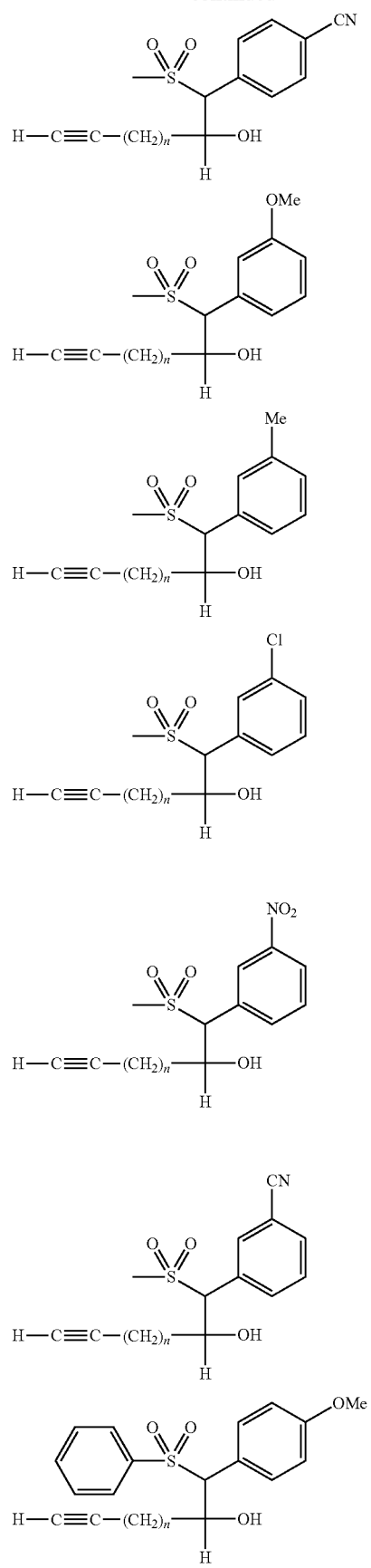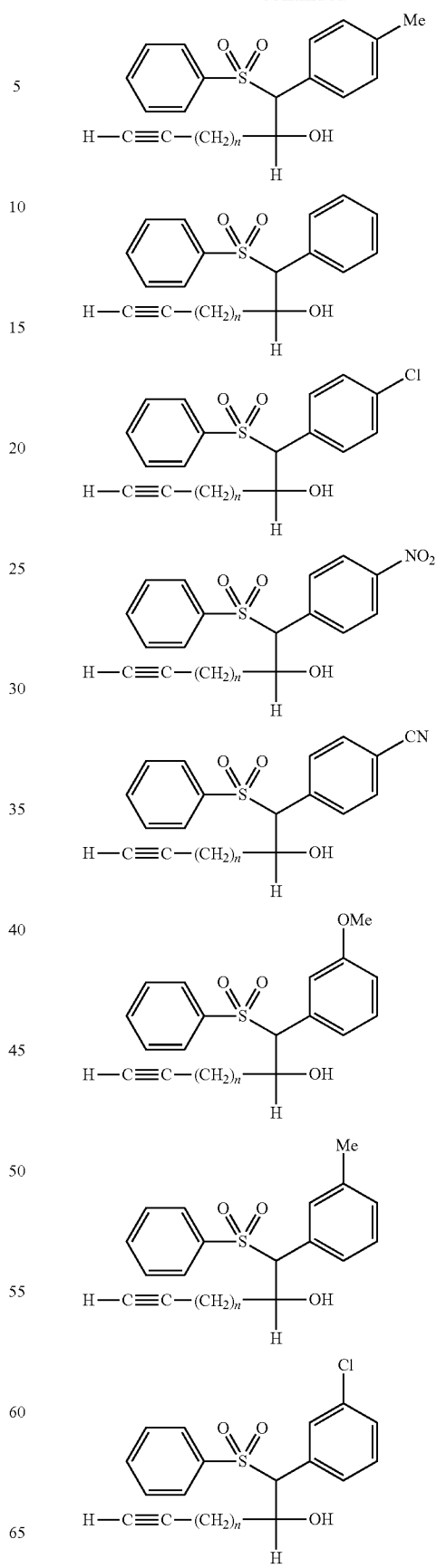

75
-continued
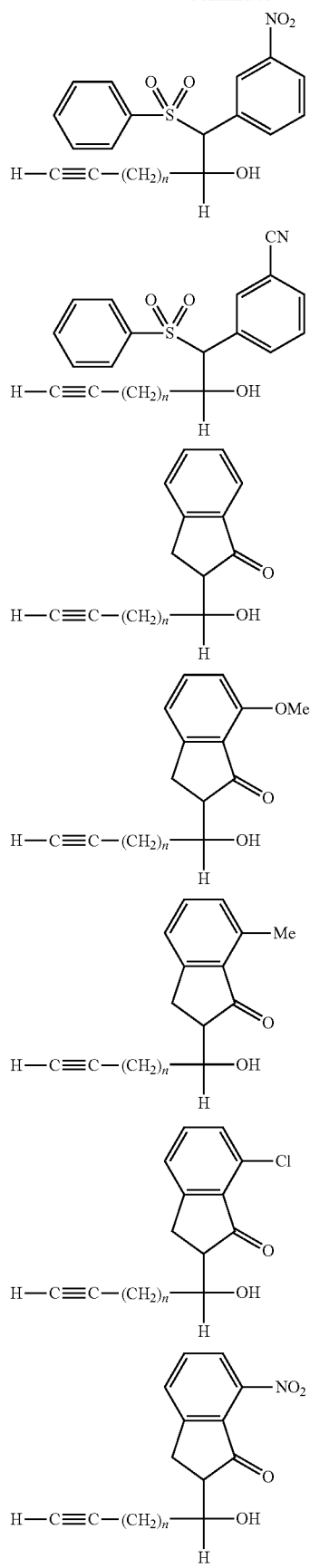
76
-continued
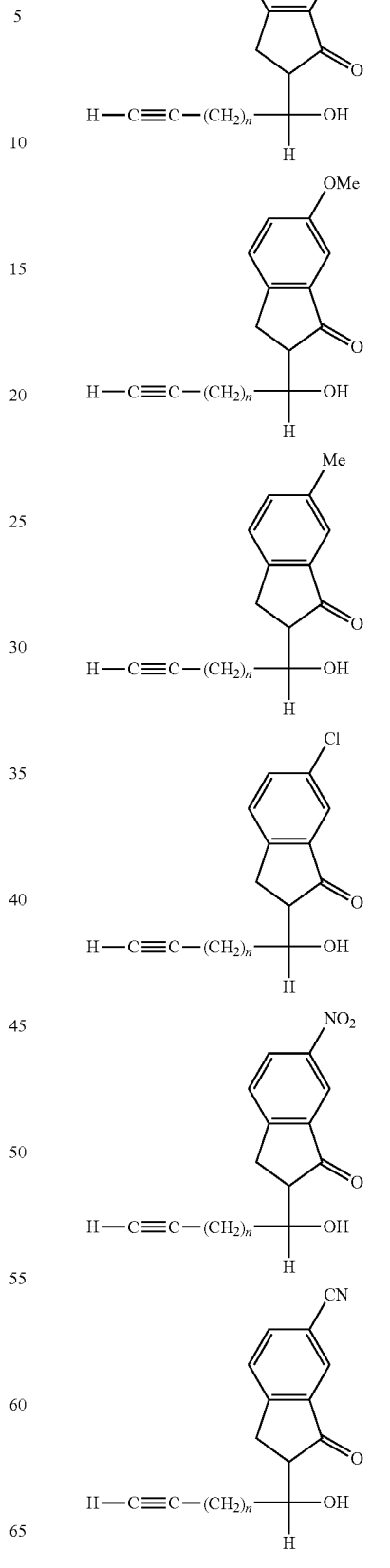

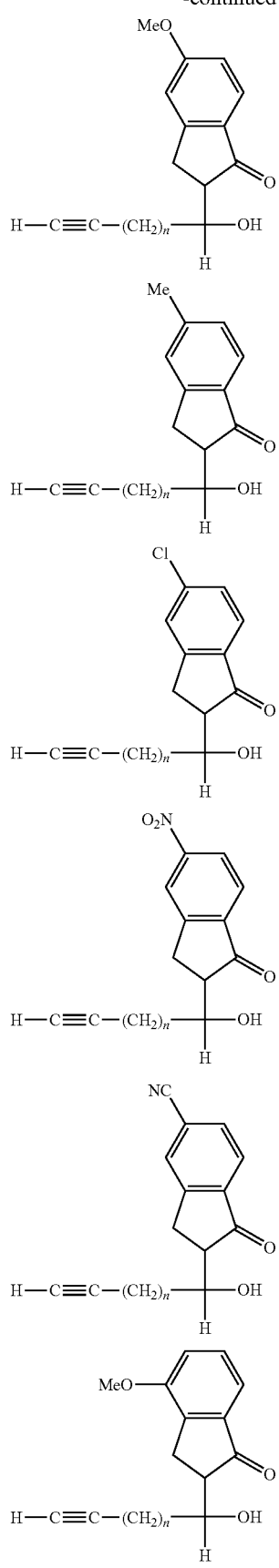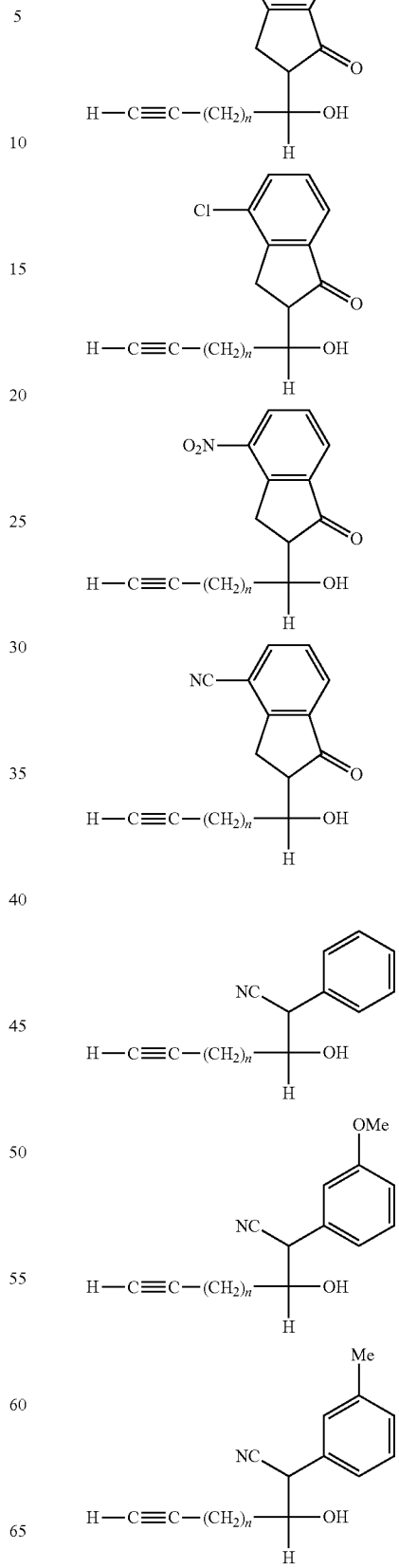

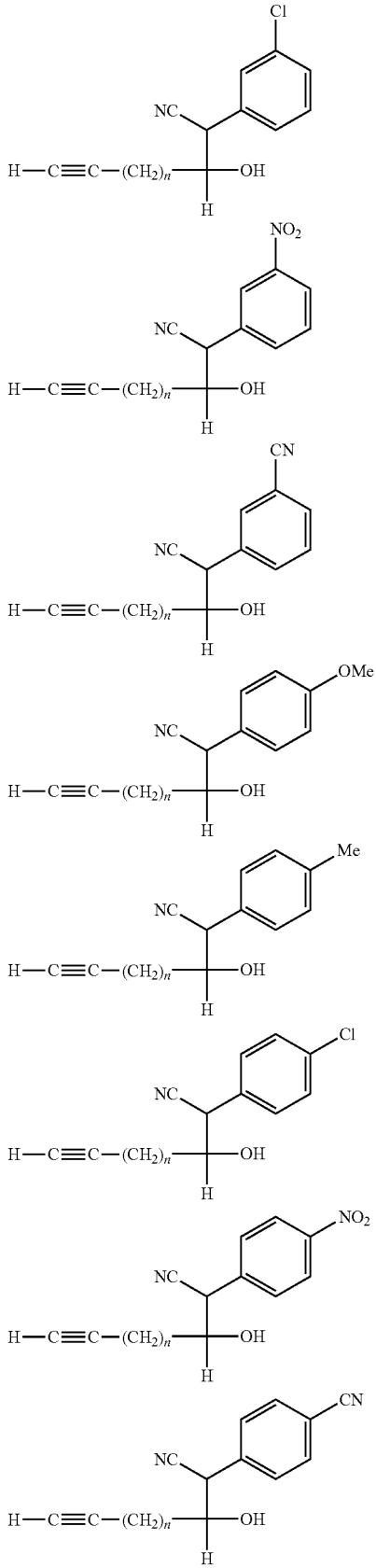

wherein n=1-6. In more particular embodiments, n=3.

In all of the foregoing examples of compounds (1a)-(1q), non-hydrogen forms of substituents on ring systems may be present in multiple locations, preferably at no more than 2 or 3 locations. The non-hydrogen substituents on a single ring may be the same or different.

In another embodiment, L is

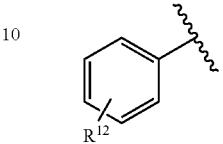

wherein $R^{12}$ is $NH_2$, $N_3$, Cl, Br, I, SH, OH, COOH, CHO, $CH=CH_2$, CCH, or maleimido.

In another embodiment, L is a group of the formula

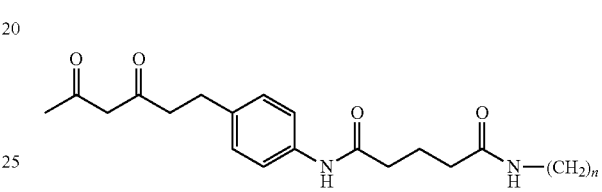

wherein n=1-6. These compounds may be prepared starting from compounds wherein $L=(CH_2)_nNH_2$, by reaction with 4-[4-(3,5-Dioxo-hexyl)-phenylcarbamoyl]-butyric acid in the presence of a condensing agent, for example a carbodiimide (DCC, EDCI) or a uronium reagent (e.g., HATC, HBTA, TATU).

The nature of L' is determined by the nature of the foregoing embodiments of L, and thus these embodiments are illustrative of formulas (3) and (4).

Preparation of Compounds of Formula (1)

The compounds of formula (1) wherein A is absent may be prepared by the addition of a carbanion $R^1R^2CH^-$ formed by reacting $R^1R^2CH_2$ with a strong base, for example butyllithium, NaH, lithium diisopropylamide, lithium bis(trimethylsilylamide), or similar, with a molecule $L-C(=X)R^5$ to produce a compound of formula (1x)

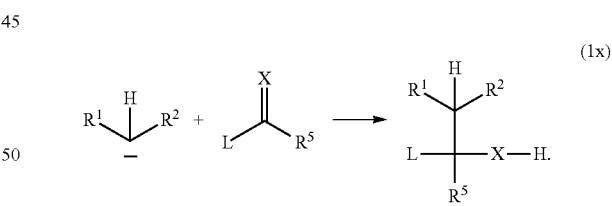

Alternatively, compounds of formula (1x) wherein A is absent and X=O may be prepared by a two-step process. In the first step, the addition of a carbanion $R^1R^2CH^-$ formed by reacting $R^1R^2CH_2$ with a strong base, for example butyllithium, NaH, lithium diisopropylamide, lithium bis(trimethylsilylamide), or similar, with an ester $L-C(=O)OR^*$, wherein R* is lower alkyl, produces an intermediate ketone $R^1R^2CH-C(=O)-L$, which may in the second step be reacted with a suitable reducing agent, for example $NaBH_4$ or $NaBH_3CN$, to provide the compound of formula (1) wherein X=O.

For example, when L-CHO is 5-hexenal, a compound of formula (1a) wherein X=O and L is $(CH_2)_3CH=CH_2$ is obtained. When L-CHO is 5-hexynal, a compound of formula (1a) wherein X=O and L is (CH$_2$)$_3$CCH is obtained. When L is 6-azidohexanal, a compound of formula (1a) wherein X=O and L is (CH$_2$)$_5$N$_3$ is obtained. When L is 3-azidobenzaldehyde, a compound of formula (1a) is obtained wherein X=O and L is 3-azidophenyl. When L=4-bromobenzaldehyde, a compound of formula (1a) wherein X=O and L is 4-bromophenyl is obtained.

For example, when R$^1$R$^2$CH$_2$=fluorene is reacted with a strong base, for example butyllithium, NaH or lithium diisopropylamide, to form a fluorenyl carbanion, which is then reacted with L-CHO, the reaction is as follows:

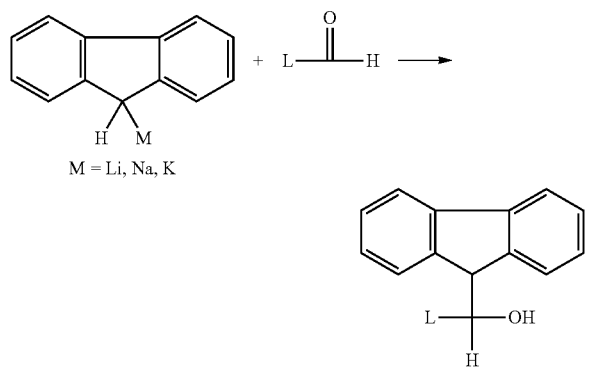

Corresponding compounds wherein X=S may be similarly prepared using the appropriate analogue Z—C(=S)R$^5$, or may alternatively be prepared by subsequent chemical transformation of compounds (1a) using methods known in the art, for example activation of the alcohol group in (1a), for example by conversion to a bromide using PBr$_3$ or Ph$_3$PBr$_2$, or by conversion to the tosylate or triflate, and displacement by a suitable nucleophilic group such as thiourea or thiosulfate to form a compound of formula (1b). In a preferred embodiment, thiosulfate is used to form an intermediate that is hydrolyzed by acid treatment to form the thiol.

In certain embodiments of the invention, A=alkenylene (C$_2$). Compounds wherein A=alkenyl (C$_2$) may be prepared by addition of the carbanion derived by lithiation of R$^1$R$^2$CH$_2$, for example using a strong base such as NaH, butyllithium, lithium bis(trimethyl-silylamide), or similar, to an unsaturated compound such as methyl 3-(dimethylamino)-acrylate to provide an intermediate ester, which may be reduced, either via one step or through multiple steps, to the corresponding unsaturated aldehyde:

Reaction of the unsaturated aldehyde with an arylboronic acid R$^{12}$-aryl-B(OH)$_2$ in the presence of a palladium catalyst, for example as described in *Org. Letts.* (2005) 7:4153-5, provides a compound of formula (1c), wherein A=alkenyl (C$_2$), L=substituted aryl, and X=O.

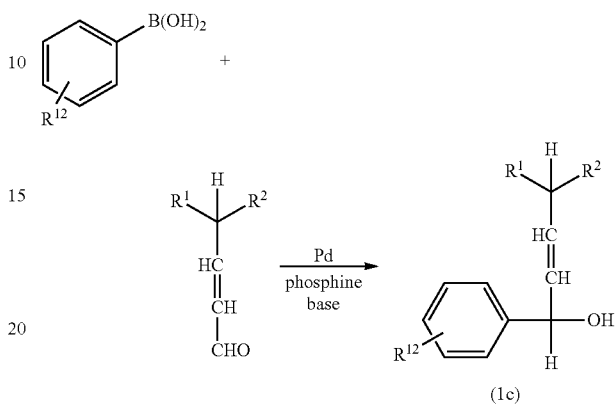

Alternatively, reaction of the unsaturated aldehyde with an allylborane according to the method of Soderquist provides compounds of formula (1d), wherein A=alkenyl (C$_2$), X=O and L=CH$_2$CH=CH$_2$, and formula (1e), wherein A=alkenyl (C$_2$), X=O and L=CH$_2$CCH. See Burgos, C. H., et al., *J. Am. Chem. Soc.* (2005) 127:8044.

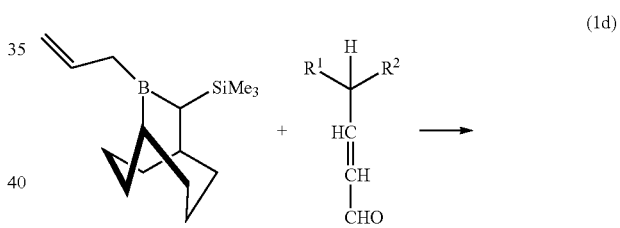

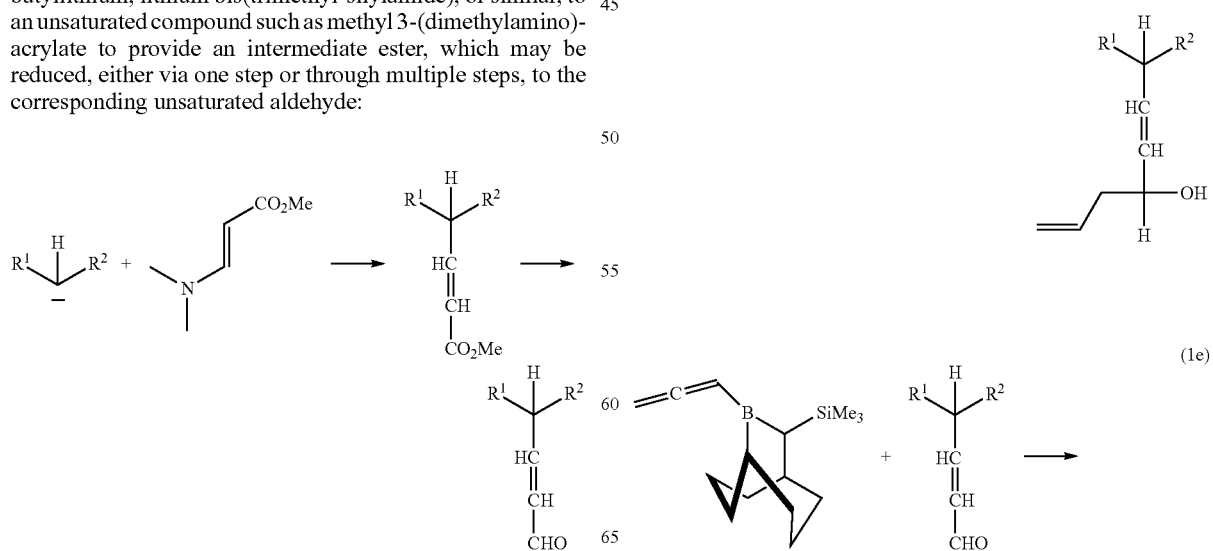

-continued

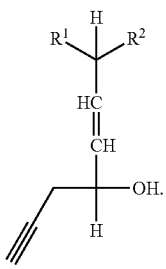

Preparation of Compounds of Formulas (2), (3) and (4)

The starting materials of formula (1) are then derivatized either first to the drug or first to the macromolecule to obtain an intermediate in the formation of the compound of formula (3). In these intermediates and in the product of formula (3), all of the embodiments which result from the many illustrated forms of formula (1), and specifically embodiments of L, A, X, $R^1$, $R^2$ and $R^5$ are retained in the intermediates and in the final product of formula (3), except that L, when reacted with the macromolecule, becomes L' as a result of this reaction.

Thus, in the following illustrations of the intermediate wherein the drug is first added, all of the embodiments of R1, R2, R5, A, X and L set forth above for formula (1) are included as illustrations of the compounds of formula (2):

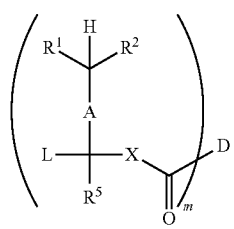

(2)

wherein m is an integer of 1-10;
Z is the residue of a macromolecule;
L is a linking moiety that can react to couple a macromolecule;
D is the residue of a drug or of a prodrug;
X is O or S;
A is alkenyl ($C_2$), aryl or absent;
each $R^1$ and $R^2$ is independently H; CN, $NO_2$;
optionally substituted aryl;
optionally substituted heteroaryl;
optionally substituted alkenyl;
optionally substituted alkynyl; or
each $R^1$ and $R^2$ is independently $COR^3$ or $SOR^3$ or $SO_2R^3$ wherein
$R^3$ is H or optionally substituted alkyl;
optionally substituted aryl;
optionally substituted heteroaryl;
optionally substituted alkenyl;
optionally substituted alkynyl; or
OR or $NR_2$ wherein each R is independently H or optionally substituted alkyl; or
each $R^1$ and $R^2$ is independently $SR^4$ wherein
$R^4$ is optionally substituted alkyl;
optionally substituted aryl;
optionally substituted heteroaryl;
optionally substituted alkenyl; or
optionally substituted alkynyl;

wherein $R^1$ and $R^2$ may be joined to form a 3-8 member ring; and
wherein both $R^1$ and $R^2$ cannot be H;
wherein $R^5$ is H or alkyl ($C_{1-6}$).

Thus, L, A, $R^1$, $R^2$ and $R^5$ as well as X are generically defined as above for the compound of formula (1), and the specific embodiments of these substituents illustrated above for formula (1) are hereby incorporated by reference as examples of the compounds of formula (2).

The compounds of formula (2) can themselves release the therapeutic agent at a controlled rate or they can be used as intermediates to connect the therapeutic agent with a macromolecule. Both formula (2) and (3) release the therapeutic agent at a controlled rate according to a pH-dependent elimination mechanism.

As set forth above, the nature of $R^1$, $R^2$, A and L all influence the rate of release.

Compounds of formula (2) may be generally prepared by condensation of a molecule of formula (1), described above, with a drug molecule D. In one embodiment of the invention, a compound of formula (1) is first activated for condensation by reaction with a suitable reagent, for example phosgene or triphosgene, optionally in the presence of N-hydroxysuccinimide; 1,1-carbonyldiimidazole; 1,1-carbonylditriazole; or similar reagents for the conversion of a compound of formula (1) into an activated compounds of formula (1*), wherein W=F, Cl, imidazolyl, triazolyl, or O-succinimidyl:

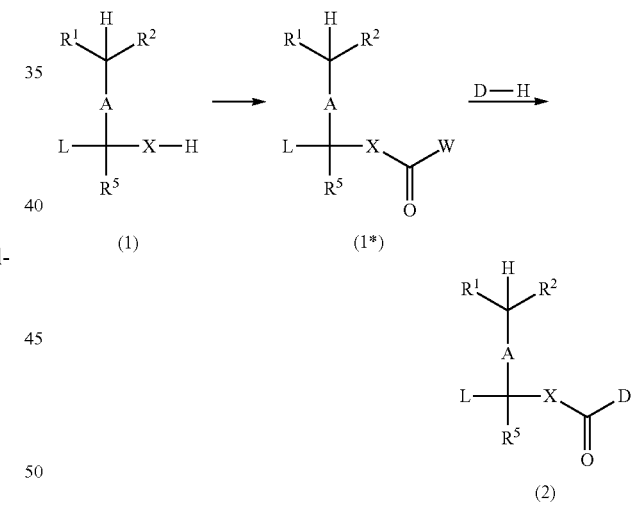

For example, reaction of a compound of formula (1) wherein X=O with triphosgene and N-hydroxysuccinimide yields a compounds of formula (1*) wherein X=O and W=O-succinimidyl.

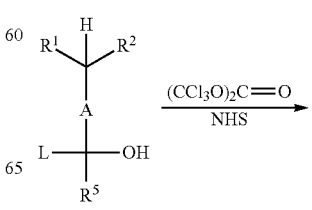

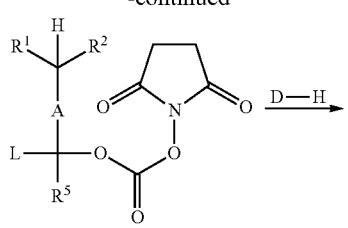

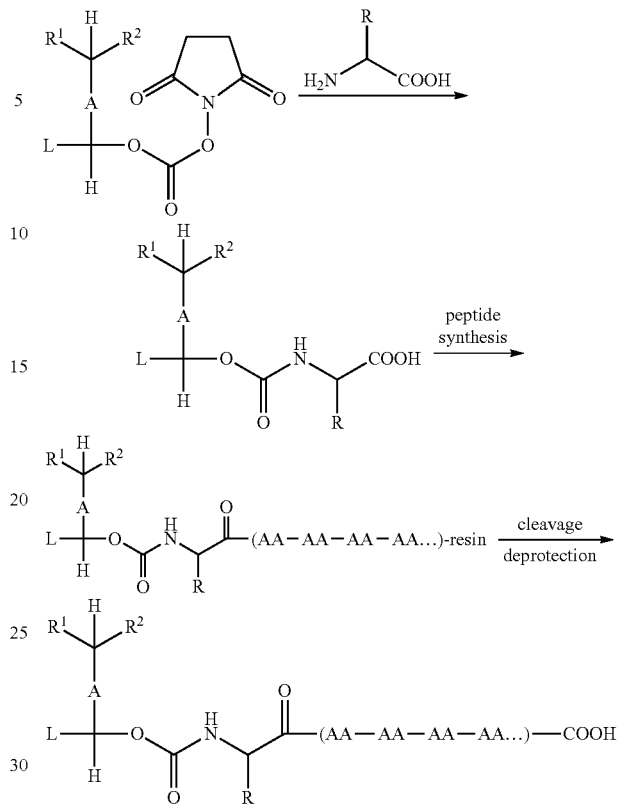

Compounds of formula (1*) wherein X=O and W=O-succinimidyl are particularly preferred when the drug molecule to be conjugated, D-H, has an amino group. In this case, the resulting prodrug of formula (2) comprises a carbamate linkage. For cases wherein D-H is a peptide or protein drug, the amino group that reacts with the compounds of formula (1*) may be a terminal alpha-amino group or the amino group of a side-chain, for example of a lysine, ornithine, or unnatural amino acid residue.

Alternatively, the activating reagent may be a substituted phenyl chloroformate, for example, 4-nitrophenyl chloroformate, 2,4-dinitrophenyl chloroformate, or pentafluorophenyl chloroformate, resulting in formation of an intermediate substituted phenyl carbonate.

Compounds of formula (1*) wherein X=O and W=F or Cl are particularly preferred when the drug molecule to be conjugated, D-H, has no amino group but instead has a hydroxy group, for example when D-H is a peptide or protein drug from a side-chain tyrosine, serine, or threonine residue, or when D-H is a nucleic acid-based drug such as a deoxynucleic acid or ribonucleic acid.

In the case of peptide-, protein-, or nucleic acid-based drugs, multiple reactive groups may be present leading to multiple reactions with the compound of formula (1*). The extent of this multiple reaction may be controlled using standard conditions known in the art, for example by varying the reaction temperature, concentrations, and stoichiometries in order to obtain the desired reaction product.

In one embodiment of the invention, D is a peptide drug, wherein D is conjugated to the molecule of formula (1) to produce a molecule of formula (2). In another embodiment of the invention, D is a peptide drug, wherein the molecule of formula (2) is prepared by a method in which the molecule of formula (1) is attached during the synthesis of D. For example, the final step in the synthesis of D by solid-phase peptide synthesis methods well-known in the art involves attachment of the N-terminal amino acid of the sequence of peptide D in protected form. In the present embodiment, this final step uses the N-terminal amino acid in a form using a compound of formula (1) as the protecting group.

wherein R is the side chain of an amino acid.

This embodiment is advantageous in that the position and stoichiometry of derivitization is completely controlled.

As described above, the drug is conjugated via the XH group, which is OH, or SH. The drug will comprise a compatible functional group, for example carboxyl, OH, $NH_2$, alkyl-NH such as MeNH, EtNH, and $^iPrNH$, aryl-NH such as phenyl-NH or substituted phenyl-NH, and SH. The functional groups on the carrier and on the drug are conjugated using a carbonyl (C=O) group.

In general, the drugs of interest are peptides or proteins or nucleic acids, such as aptamers or antisense oligomers, or small molecules.

Examples of suitable drugs include those for human or veterinary use including, but not limited to, antidiabetic drugs (e.g., insulin); growth promoters (e.g., human or bovine growth hormone); antibacterials including aminoglycosides (e.g., gentamicin, neomycin and streptomycin), penicillins, (amoxicillin, ampicillin, piperacillin), cephalosporins, (e.g., cefaclor, cefminox and cephalexin), macrolides (e.g., carbomycin, erythromycin, telithromycin) and peptides (e.g., bacitracin, gramicidins, and polymyxins), trimethoprim, piromidic acid, and sulfamethazine; analgesic and anti-inflammatory drugs (e.g., acetaminophen, aspirin, ibufenac, indomethacin), antiallergic and antiasthmatic drugs (e.g., amlexanox and cromolyn), antihypercholesterolemic drugs (e.g., clofibric acid, oxiniacic acid and triparanol), beta-adrenergic blockers and antihypertensive drugs (e.g., bupranolol, captopril, indenolol, propranolol and 4-aminobutanoic acid), antineoplastic drugs (e.g., daunorubicin, azacytidine, 6-mercaptopurine, interferons, interleukin-2, methotrexate, taxol 5-fluorouridine, 5-fluorouracil, capcitibine, and vinblastine), antiviral drugs (e.g., acyclovir, ganciclovir, amantadine, interferons, AZT and ribavirin, etc).

Particularly preferred are peptide, protein, and nucleic acid drugs. Examples of peptide drugs suitable for use in the invention include but are not limited to: glucagon-like peptide 1 (GLP-1), exendin-2, exendin-3, exendin-4, atrial natriuretic factor (ANF), ghrellin, vasopressin, growth hormone, growth hormone-releasing hormone (GHRH), RC-3095, somatostatin, bombesin, PCK-3145, Phe-His-Ser-Cys-Asn (PHSCN), IGF1, B-type natriuretic peptide, peptide YY (PYY), interferons, thrombospondin, angiopoietin, calcitonin, gonadotropin-releasing hormone, hirudin, glucagon, anti-TNF-alpha, fibroblast growth factor, granulocyte colony stimulating factor, obinepitide, pituitary thyroid hormone (PTH), leuprolide, sermorelin, pramorelin, nesiritide, rotigaptide, cilengitide, MBP-8298, AL-108, enfuvirtide, thymalfasin, daptamycin, HLF1-I1, Lactoferrin, Delmitide, glutathione, T-cell epitope PR1, Protease-3 peptides 1-11, B-cell epitope P3, lutenizing hormone-releasing hormone (LHRH), substance P, neurokinin A, neurokinin B, CCK-8, enkephalins, including leucine enkephalin and methionine enkephalin, dermaseptin, [des-Ala20, Gln34]-dermaseptin, surfactant-associated antimicrobial anionic peptide, Apidaecin IA; Apidaecin IB; OV-2; 1025, Acetyl-Adhesin Peptide (1025-1044) amide; Theromacin (49-63); Pexiganan (MSI-78); Indolicidin; Apelin-15 (63-77); CFPlO (71-85); Lethal Factor (LF) Inhibitor Anthrax related; Bactenecin; Hepatitis Virus C NS3 Protease Inhibitor 2; Hepatitis Virus C NS3 Protease Inhibitor 3; Hepatitis Virus NS3 Protease Inhibitor 4; NS4A-NS4B Hepatitis Virus C(NS3 Protease Inhibitor 1); HIV-I, HIV-2 Protease Substrate; Anti-FM Peptide; Bak-BH3; Bax BH3 peptide (55-74) (wild type); Bid BH3-r8; CTT (Gelatinase Inhibitor); E75 (Her-2/neu) (369-377); GRP78 Binding Chimeric. Peptide Motif; p53(17-26); EGFR2/KDR Antagonist; Colivelin AGA-(C8R) HNGl 7 (Humanin derivative); Activity-Dependent Neurotrophic Factor (ADNF); Beta-Secretase Inhibitor 1; Beta-Secretase Inhibitor 2; ch[beta]-Amyloid (30-16); Humanun (HN) sHNG, [Glyl4]-HN, [Glyl 4]-Humanin; Angiotensin Converting Enzyme Inhibitor (BPP); Renin Inhibitor III; Annexin 1 (ANXA-1; Ac2-12); Anti-Inflammatory Peptide 1; Anti-Inflammatory Peptide 2; Anti-Inflammatory Apelin 12; [D-Phel2, Leul4]-Bombesin; Antennapedia Peptide (acid) (penetratin); Antennepedia Leader Peptide (CT); Mastoparan; [Thr28, Nle31]-Cholecystokinin (25-33) sulfated; Nociceptin (1-13) (amide); Fibrinolysis Inhibiting Factor; Gamma-Fibrinogen (377-395); Xenin; Obestatin (human); [Hisl, Lys6]-GHRP (GHRP-6); [Ala5, [beta]-Ala8]-Neurokinin A (4-10); Neuromedin B; Neuromedin C; Neuromedin N; Activity-Dependent Neurotrophic Factor (ADNF-14); Acetalin 1 (Opioid Receptor Antagonist 1); Acetalin 2 (Opioid Receptor Antagonist 2); Acetalin 3 (Opioid Receptor Antagonist 3); ACTH (1-39) (human); ACTH (7-38) (human); Sauvagine; Adipokinetic Hormone (Locusta Migratoria); Myristoylated ADP-Ribosylation Factor 6, myr-ARF6 (2-13); PAMP (1-20) (Proadrenomedullin (1-20) human); AGRP (25-51); Amylin (8-37) (human); Angiotensin I (human); Angiotensin II (human); Apstatin (Aminopeptidase P Inhibitor); Brevinin-1; Magainin 1; RL-37; LL-37 (Antimicrobial Peptide) (human); Cecropin A; Antioxidant peptide A; Antioxidant peptide B; L-Carnosine; Bcl 9-2; NPVF; Neuropeptide AF (hNPAF) (Human); Bax BH3 peptide (55-74); bFGF Inhibitory Peptide; bFGF inhibitory Peptide II; Bradykinin; [Des-Argl O]-HOE 140; Caspase 1 Inhibitor II; Caspase 1 Inhibitor VIII; Smac N7 Protein (MEK1 Derived Peptide Inhibitor 1; hBD-1 ([beta]-Defensin-1) (human); hBD-3 ([beta]-Defensin-3) (human); hBD-4 ([beta]-Defensin-4) (human); HNP-I (Defensin Human Neutrophil Peptide 1); HNP-2 (Defensin Human neutrophil Peptide-2 Dynorphin A (1-17)); Endomorphin-1; [beta]-Endorphin (human porcine); Endothelin 2 (human); Fibrinogen Binding Inhibitor Peptide; Cyclo(-GRGDSP); TP508 (Thrombin-derived Peptide); Galanin (human); GIP (human); Gastrin Releasing Peptide (human); Gastrin-1 (human); Ghrelin (human); PDGF-BB peptide; [D-Lys3]-GHRP-6; HCV Core Protein (1-20); a3Bl Integrin Peptide Fragment (325) (amide); Laminin Pentapeptide (amide) Melanotropin-Potentiating Factor (MPF); VA-[beta]-MSH, Lipotropin-Y (Proopiomelanocortin-derived); Atrial Natriuretic Peptide (1-28) (human); Vasonatrin Peptide (1-27); [Ala5, B-Ala8]-Neurokinin A (4-10); Neuromedin L (NKA); Ac-(Leu28, 31)-Neuropeptide Y (24-26); Alytesin; Brain Neuropeptide II; [D-tyrll]-Neurotensin; IKKy NEMO Binding Domain (NBD) Inhibitory Peptide; PTD-p50 (NLS) Inhibitory Peptide; Orexin A (bovine, human, mouse, rat); Orexin B (human); Aquaporin-2(254-267) (human Pancreastatin)(37-52); Pancreatic Polypeptide (human); Neuropeptide; Peptide YY (3-36) (human); Hydroxymethyl-Phytochelatin 2; PACAP (1-27) (amide, human, bovine, rat); Prolactin Releasing Peptide (1-31) (human); Salusin-alpha; Salusin-beta; Saposin C22; Secretin (human); L-Selectin; Endokinin A/B; Endokinin C (Human); Endokinin D (Human); Thrombin Receptor (42-48) Agonist (human); LSKL (Inhibitor of Thrombospondin); Thyrotropin Releasing Hormone (TRH); P55-TNFR Fragment; Urotensin II (human); VIP (human, porcine, rat); VIP Antagonist; Helodermin; Exenatide; ZPlO (AVEOO1OO); Pramlinitide; AC162352 (PYY)(3-36); PYY; Obinepitide; Glucagon; GRP; Ghrelin (GHRP6); Leuprolide; Histrelin; Oxytocin; Atosiban (RWJ22164); Sermorelin; Nesiritide; bivalirudin (Hirulog); Icatibant; Aviptadin; Rotigaptide (ZP123, GAP486); Cilengitide (EMD-121924, RGD Peptides); AlbuBNP; BN-054; Angiotensin II; MBP-8298; Peptide Leucine Arginine; Ziconotide; AL-208; AL-108; Carbeticon; Tripeptide; SAL; Coliven; Humanin; ADNF-14; VIP (Vasoactive Intestinal Peptide); Thymalfasin; Bacitracin; Gramidicin; Pexiganan (MSI-78); Pl 13; PAC-113; SCV-07; HLF1-I1 (Lactoferrin); DAPTA; TRI-1144; Tritrpticin; Antiflammin 2; Gattex (Teduglutide, ALX-0600); Stimuvax (L-BLP25); Chrysalin (TP508); Melanonan II; Spantide II; Ceruletide; Sincalide; Pentagastin; Secretin; Endostatin peptide; E-selectin; HER2; IL-6; IL-8; IL-10; PDGF; Thrombospondin; uPA (1); uPA (2); VEGF; VEGF (2); Pentapeptide-3; XXLRR; Beta-Amyloid Fibrillogenesis; Endomorphin-2; TIP 39 (Tuberoinfundibular Neuropeptide); PACAP (1-38) (amide, human, bovine, rat); TGFB activating peptide; Insulin sensitizing factor (ISF402); Transforming Growth Factor Bl Peptide (TGF-Bl); Caerulein Releasing Factor; IELLQAR (8-branch MAPS); Tigapotide PK3145; Goserelin; Abarelix; Cetrorelix; Ganirelix; Degarelix (Triptorelin); Barusiban (FE 200440); Pralmorelin; Octreotide; Eptifibatide; Netamiftide (INN-00835); Daptamycin; Spantide II; Delmitide (RDP-58); AL-209; Enfuvirtide; IDR-I; Hexapeptide-6; Insulin-A chain; Lanreotide; Hexa[rho]eptide-3; Insulin B-chain; Glargine-A chain; Glargine-B chain; Insulin-LisPro B-chain analog; Insulin-Aspart B-chain analog; Insulin-Glulisine B chain analog; Insulin-Determir B chain analog; Somatostatin Tumor Inhibiting Analog; Pancreastatin (37-52); Vasoactive Intestinal Peptide fragment (KKYL-NH2); and Dynorphin A. These and other peptide and protein drugs listed, for example, in PCT publication WO2008/058016 A1 (incorporated herein by reference for identity and sequence) are suitable for use with the present invention.

Examples of protein drugs suitable for use in the invention include but are not limited to: immunotoxin SS1P, adenosine deaminase, argininase, and others.

Examples of nucleic acid-based drugs suitable for use in the invention include, but are not limited to the sense strand and antisense strand of any gene from an animal, and particularly from a mammal. Such genes can be those that are already the subjects of antisense DNAs that have been provided with the purpose of treating various diseases, for example genes for protein kinase C-alpha (Aprinocarsen, non-small cell lung cancer), BCL-2 (Oblimersen, malignant melanoma, lung cancer), ICAM-1 (ISIS-3082, Crohn's disease, HCV-related hepatitis C, ischemic/reperfusion injury in transplant), tumor necrosis factor alpha (rheumatoid arthritis, SARS, and psoriasis), adenosine A1 receptor (asthma), c-raf kinase (ovarian cancer), H-ras (pancreatic cancer), c-myc (coronary artery disease), protein kinase A RI alpha (colon cancer, AIDS), DNA methyl-transferase (solid cancers), VEGF receptor (cancer), ribonucleotide reductase (kidney cancer), cytomegalovirus IE2 (CMV retinitis), matrix metalloproteinase-9 (prostate cancer), TGF beta 2 (malignant glioma), CD49d (multiple sclerosis), PTP-1B (diabetes), c-myb (cancer), EGFR (breast cancer), mdr1 (cancer), autotaxin (cancer), phosphatidylinositol glycan anchor class F (PIGF, cancer), and GLUT-1 (cancer). The nucleic acid drugs may be DNA, modified DNA such as phosphorothioate-DNA, RNA, modified RNA such as 2'-OMe-RNA, locked nucleic acids, peptide nucleic acids, or hybrids.

In one embodiment of the invention, D is an oligonucleotide drug. The compounds of formula (2) wherein D is an oligonucleotide may be prepared by chemical synthesis of the oligonucleotide drug comprising a 5'-terminal modification that allows for conjugation with a molecule of formula (1). For example, the oligonucleotide may be chemically synthesized such that the 5'-terminal nucleotide unit, added at the last round of synthesis, comprises a phosphate group modified to contain an amino-alkyl group. The resulting amine-modified oligonucleotide is then conjugated to a molecule of formula (1) to form a molecule of formula (2) wherein D is an oligonucleotide drug. See, for example, Zhao, et al., *Bioconjugate Chemistry* (2005) 16(4):758-766.

Figure 4:
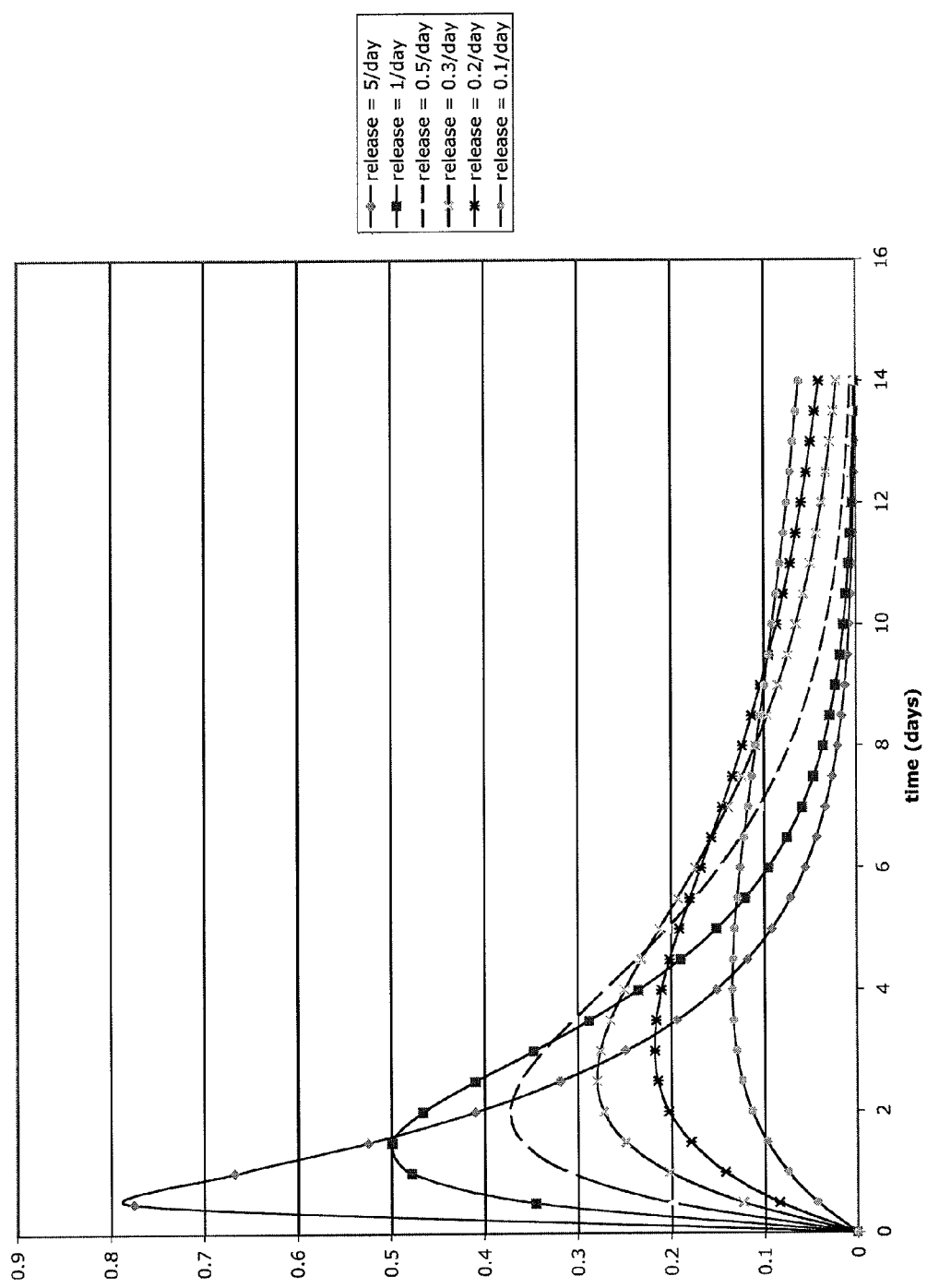
FIG. 4 shows calculated drug release profiles for a series of prodrugs having different release rates, with a fixed rate of clearance from the system of 0.5 per day, expressed as the fraction of total drug administered. Relatively fast release rates (for example, a release rate of 5 per day) gives a higher maximum concentration of released drug over a shorter duration. Relatively slow release rates (for example, a release rate of 0.1 per day) give a lower maximum concentration of released drug over a longer duration.
Figure 5:
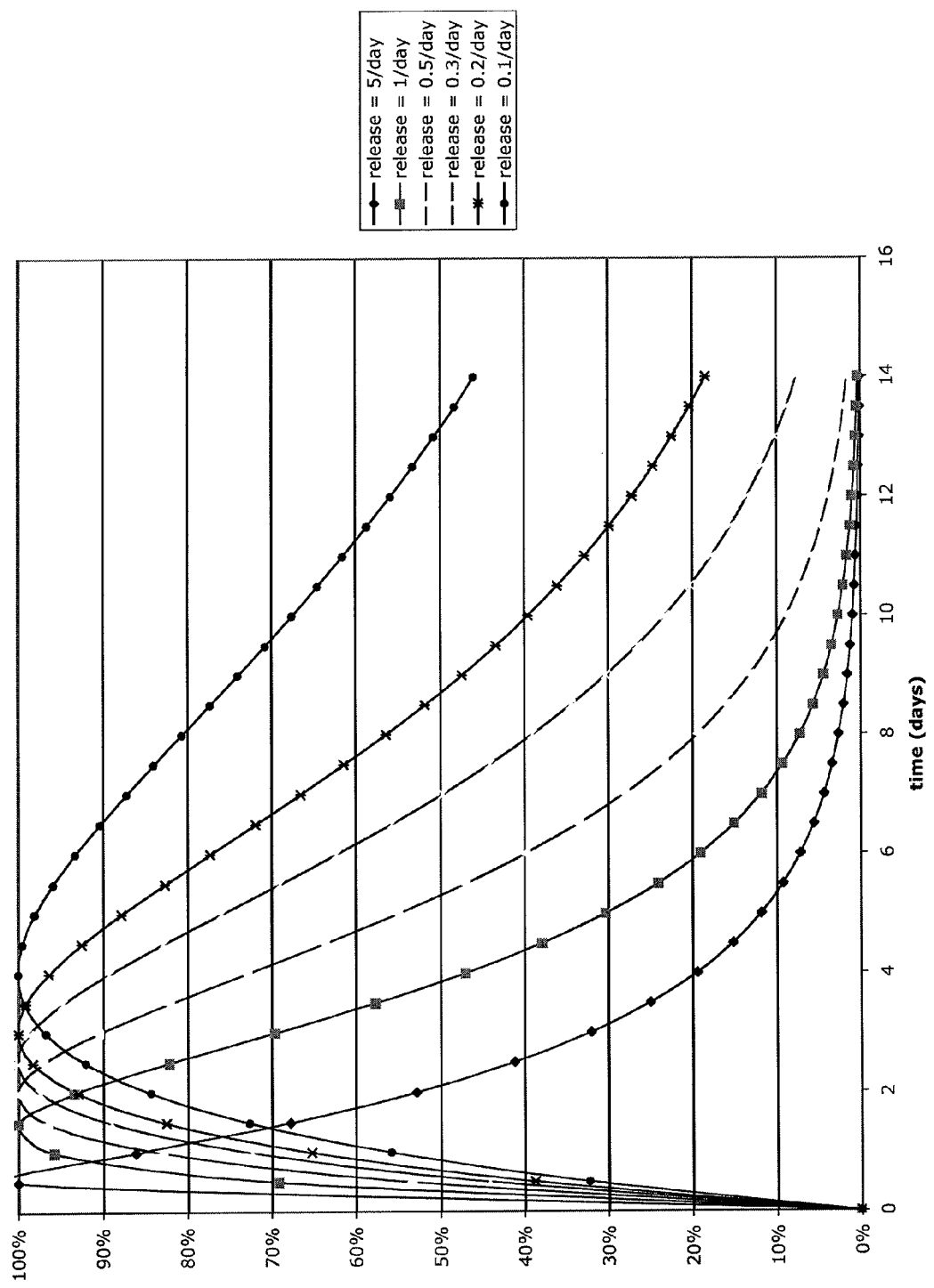
FIG. 5 shows calculated drug release profiles for a series of prodrugs having different release rates, with a fixed rate of clearance from the system of 0.5 per day, expressed as percent of the maximal concentration (% Cmax) versus time. As the rate of drug release from the prodrug or drug-macromolecular conjugate slows, the period of time after administration wherein the free drug concentration is above a particular percentage of the maximal concentration is extended.

The predicted effects of changing the release rate of the drug from the prodrug of formula (2) are illustrated in FIGS. 4 and 5. FIG. 4 shows calculated drug release profiles for a series of prodrugs having different release rates, with a fixed rate of clearance from the system of 0.5 per day, expressed as the fraction of total drug administered, assuming slow clearance of the prodrug. Relatively fast release rates (for example, a release rate of 5 per day) gives a higher maximum concentration of released drug over a shorter duration. Relatively slow release rates (for example, a release rate of 0.1 per day) gives a lower maximum concentration of released drug over a longer duration.

As the total amount of drug administered can be varied according to need, it is useful to consider the release of drug from the compound of formula (2) in terms relative to the maximal level of free drug achieved. FIG. 5 shows calculated drug release profiles for a series of prodrugs having different release rates, with a fixed rate of clearance from the system of 0.5 per day, expressed as percent of the maximal concentration (% Cmax) versus time. As the rate of drug release from the prodrug or drug-macromolecular conjugate slows, the period of time after administration wherein the free drug concentration is above a given percentage of the maximal concentration is extended.

The models illustrated in FIGS. 4 and 5 serve to demonstrate that various drug time-concentration profiles may be achieved by selecting the appropriate drug release rate from the prodrug of formula (2) relative to the clearance rate of the drug from the system.

The invention also includes compositions containing mixtures comprising two or more prodrugs of formula (2) where the drugs, D, are the same or different. In one embodiment, of such a mixture each prodrug of formula (2) has a different rate of drug release under physiological conditions.

The pharmacokinetics are also further controlled by including a macromolecule as on compounds of the formula

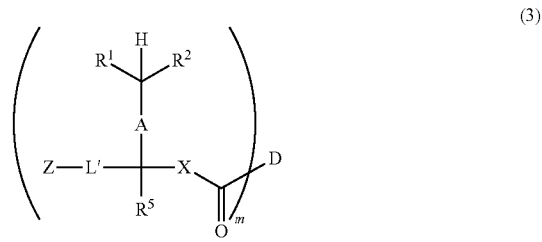

(3)

wherein m is an integer of 1-10;
Z is the residue of a macromolecule;
L' is the residue of a linker;
D is the residue of a drug or of a prodrug;
X is O or S;
A is alkenyl ($C_2$), aryl or absent;
each $R^1$ and $R^2$ is independently H; CN;
$NO_2$;
optionally substituted aryl;
optionally substituted heteroaryl;
optionally substituted alkenyl;
optionally substituted alkynyl; or
each $R^1$ and $R^2$ is independently $COR^3$ or $SOR^3$ or $SO_2R^3$ wherein
$R^3$ is H or optionally substituted alkyl;
optionally substituted aryl;
optionally substituted heteroaryl;
optionally substituted alkenyl;
optionally substituted alkynyl; or
OR or $NR_2$ wherein each R is independently H or optionally substituted alkyl; or
each $R^1$ and $R^2$ is independently $SR^4$ wherein
$R^4$ is optionally substituted alkyl;
optionally substituted aryl;
optionally substituted heteroaryl;
optionally substituted alkenyl; or
optionally substituted alkynyl;
wherein $R^1$ and $R^2$ may be joined to form a 3-8 member ring; and
wherein both $R^1$ and $R^2$ cannot be H; and
wherein $R^5$ is H or alkyl ($C_{1-6}$).

When m=1, the drug-macromolecule conjugates of formula (3) have the more specific formula:

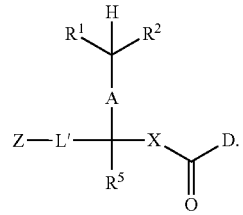

In many embodiments, $R^5$ is H.

As was the case for compounds of formula (2), the embodiments set forth for $R^1$, $R^2$, A, X, $R^5$ and L illustrated in the case of formula (1) apply and these embodiments are hereby incorporated by reference as appropriate substituents of formula (3). In the case of L', the nature of L determines its structure, and thus the variants described in connection with formulas (1) and (2) apply here as well.

The drugs illustrated and listed above in connection with formula (2) apply to formula (3) as well.

Upon release of the drug from formula (3) by non-enzymatic elimination, the linking group remains attached to the macromolecule. It has been demonstrated that clearance rate of molecules from the body is dependent upon their hydrodynamic radius, and hence their molecular weight. See, for example, Veronese, *Biomaterials* (2001) 22:405-417, which shows that the half-life of superoxide dismutase (SOD) in mouse increases from 0.08 hours for free SOD, to 1.5 hours for SOD conjugated to PEG of molecular weight 1,900 Da, to 36 hours for SOD conjugated to PEG of molecular weight 72,000 Da. Thus, conjugation of the prodrugs of formula (2) to a macromolecule to give a molecule of formula (3) can be used to increase the circulating lifetime of the prodrug.

Macromolecular carriers for the delivery of drugs are also alternative intermediates in the formation of the compounds of formula (3).

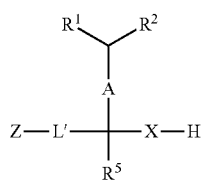

(4)

As was the case for the compounds of formulas (2) and (3), all of the variations specifically described for $R^1$, $R^2$, $R^5$, X and L described for formula (1) are incorporated into specific embodiments of compounds of formula (4).

In some embodiments, Z is a protein, oligosaccharide, or synthetic polymer having a molecular weight of between 10,000 and 250,000.

In certain embodiments, the macromolecule Z is a synthetic polymer having a molecular weight of between 10,000 and 250,000. In more specific embodiments, the macromolecule Z is a synthetic polymer having a molecular weight of between 10,000 and 100,000. In certain embodiments of the invention, Z is a derivatized linear, branched, or dendrimeric poly(ethyleneglycol) (PEG), monomethoxy-PEG (mPEG), poly(ethyleneimine) (PEI), or PEG-PEI copolymer. Various sizes of derivatized synthetic polymers like PEG and mPEG are commercially available, having a variety of terminal functional groups resulting in molecules comprising hydroxyl, amine, azide, carboxyl, aldehyde, N-hydroxysuccinimidyl ester, imidazolylcarboxamino, imidazolylcarboxy, nitrophenyl carbonate, isocyanate, maleimide, thiol, or epoxide functional groups. Other synthetic polymer derivatives may be prepared using methods known in the art, for example by derivitization using a bromomethyl-substituted aromatic or heteroaromatic aldehyde or an allyl or propargyl halide.

In another embodiment, the macromolecule Z is a protein of molecular weight between 10,000 and 250,000. In a more specific embodiment of the invention, Z is an antibody or antibody fragment, either monoclonal or polyclonal. Depending upon the sequence of the protein, various reactive functional groups such as amines and thiols will be present. Alternatively, the protein can be chemically derivatized using methods known in the art to add groups such as thiols and maleimides.

In another embodiment, Z is an oligosaccharide having a molecular weight of between 10,000 and 250,000. In certain embodiments, Z is a dextran having a molecular weight of between 10,000 and 250,000. In more specific embodiments, Z is a dextran having a molecular weight of between 10,000 and 100,000.

The macromolecule Z will comprise at least one functional group $R^{13}$ suitable for reaction with a molecule of formula (1) or (2). For compounds of the invention, suitable $R^{13}$ groups include but are not limited to: hydroxyl, amine, azide, carboxyl, aldehyde, N-hydroxysuccinimidyl ester, imidazolylcarboxamino, imidazolylcarboxy, nitrophenyl carbonate, isocyanate, maleimide, thiol, epoxide, CCH (terminal alkyne), and guanidino groups.

In a particular embodiment of the invention, Z is the antibody m38c2 or a humanized version thereof (US patent application 2006/0205670, incorporated herein by reference).

In certain embodiments in the compounds of the formula (3) or (4) Z is selected from the group consisting of an antibody; an albumin; a linear, branched, or dendrimeric polyethylene glycol (PEG); a linear, branched, or dendrimeric monomethoxypolyethylene glycol (mPEG); a linear, branched, or dendrimeric polyethylene imine (PEI); a linear, branched, or dendrimeric PEG-PEI copolymer; a linear, branched, or dendrimeric dextran; and a nanoparticle. In particular embodiments of the invention, the drug-macromolecule conjugates have the formula (3a) wherein Z is an antibody. In other particular embodiments of the invention, the drug-macromolecule conjugates have the formula (3a) wherein Z is a linear, branched, or dendrimeric polyethylene glycol (PEG). In other particular embodiments of the invention, the drug-macromolecule conjugates have the formula (3a) wherein Z is a linear, branched, or dendrimeric monomethoxypolyethylene glycol (mPEG).

In compounds of formulas (3) and (4) of the invention, L' can be $(CH_2)_n NHCO$, $(CH_2)_n NHCH_2$, $(CH_2)_n NHCONH$, $(CH_2)_n$triazolyl, $(CH_2)_n$thiosuccinimidoyl, $(CH_2)_n$(hydroxyethylthio), $(CH_2)_n$succinimidoylthio, $(CH_2)_n CONH$,

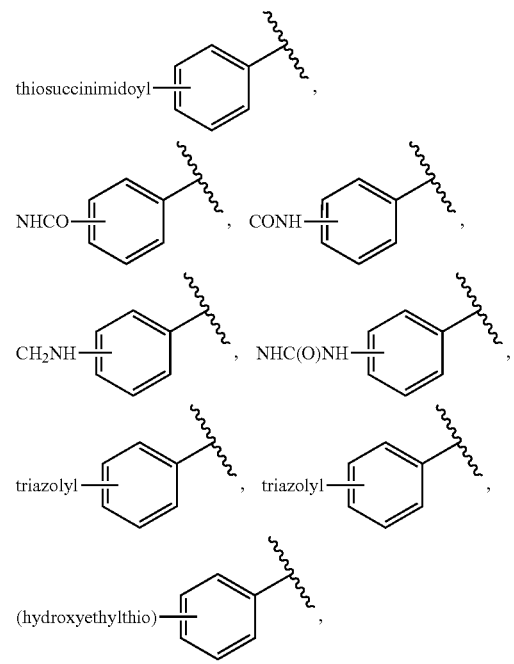

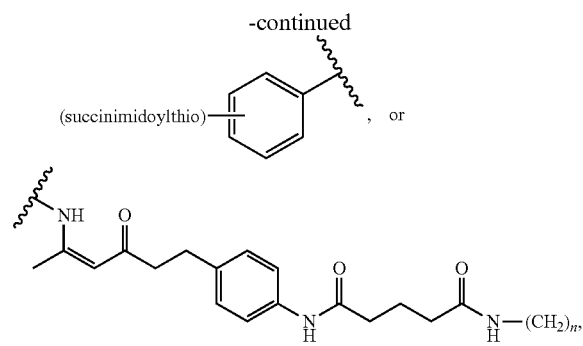

wherein n=1-6.

Coupling to Macromolecules

The compounds of formula (4) are prepared as described below wherein the reactant to be coupled to the macromolecule Z is the compound of formula (1); if the compound of formula (2) is employed, the compounds of formula (3) result. Similarly, the compounds of formula (4) may be converted as described above into compounds of formula (3) by reaction with appropriate drugs as described above.

In each case, the linking group L' is formed by the reaction of a functional group $R^{13}$ on the macromolecule Z with a functional group $R^{12}$ on the linker group L of the molecules of formula (1) or (2) during the conjugation process. As described above, in compounds of formulas (1) and (2), L is $(CH_2)_n R^{12}$,

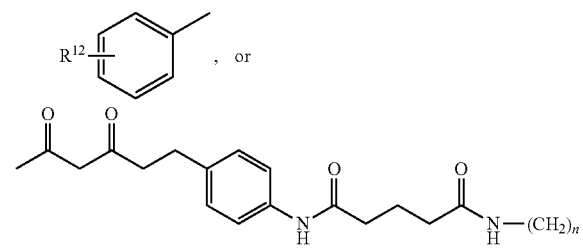

wherein n=1-6 and $R^{12}$ is $NH_2$, $N_3$, Cl, Br, I, SH, COOH, CHO, CH=$CH_2$, CCH, or maleimido.

Compounds of formula (3) or (4) may be prepared by any of several routes, the most appropriate of which will be dependent primarily upon the nature of the group $R^{12}$ on group L. The appropriate method and nature of the resulting linking group L' is determined by the choice of functional groups as follows, using reaction with the compound of formula (2) when m=1 as illustrated.

When $R^{12}$ is $NH_2$, the derivatized macromolecule Z—$R^{13}$ is conjugated to the compounds of formula (1) or (2) through $R^{13}$=COOH, using a condensing agent such as a carbodiimide, or directly using $R^{13}$=CO—O-succinimidoyl (N-hydroxysuccinimidoyl ester), CO-imidazolyl, or CO—O-(nitrophenyl), to give the amide linkage L'=$(CH_2)_n$NHCO or

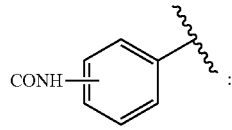

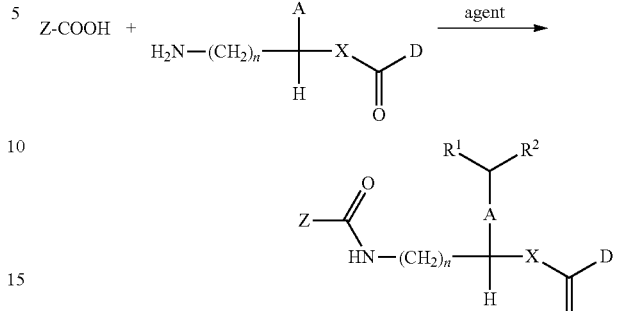

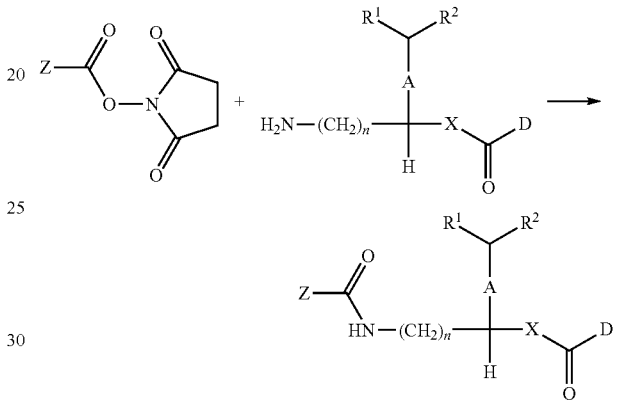

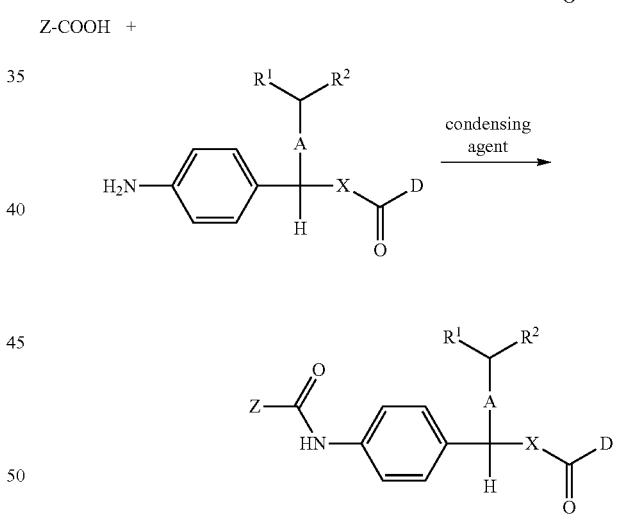

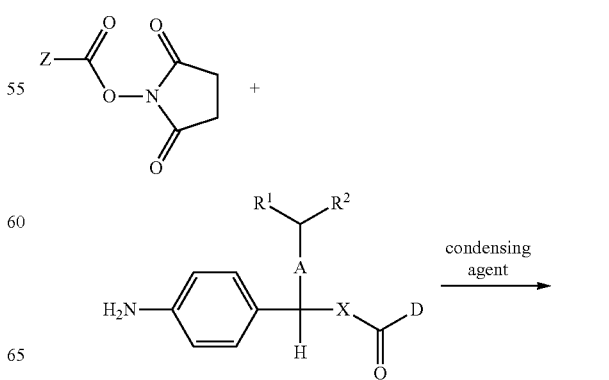

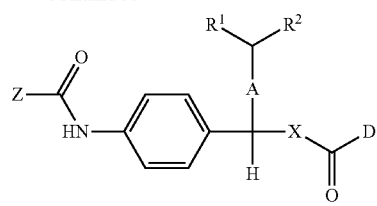

wherein Z, X, A, D, R', and R² are as defined above.

Alternately, when $R^{12}$ is $NH_2$, the derivatized macromolecule $Z—R^{13}$ is conjugated to the compounds of formula (1) or (4) through $R^{13}$=CHO, using reductive amination, for example with NaBH₃CN, to give the amine linkage L'=$(CH_2)_n$NH—$CH_2$ or

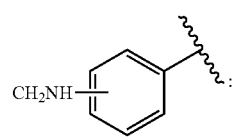

Z—CHO +

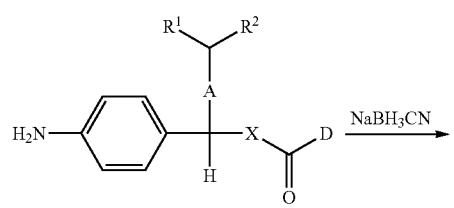

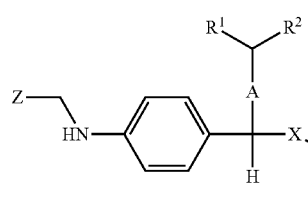

Z—CHO +

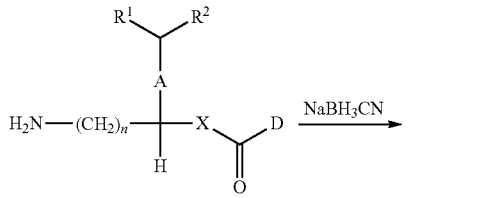

wherein Z, X, A, D, R¹, and R² are as defined above.

Alternately, when $R^{12}$ is $NH_2$, the derivatized macromolecule $Z—R^{13}$ is conjugated to the compounds of formula (1) or (2) through $R^{13}$=isocyanate, to give the urea linkage L'=$(CH_2)_n$NH—CO—NH— or

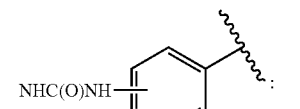

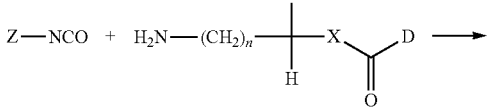

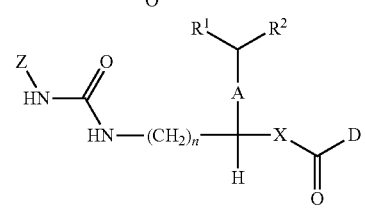

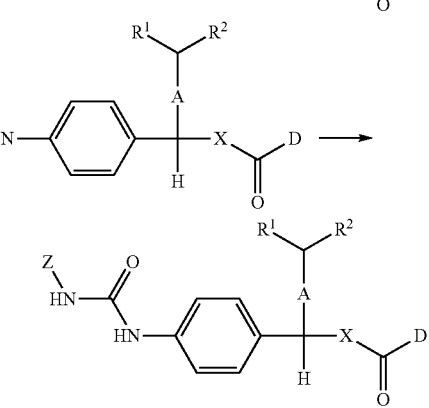

wherein Z, X, A, D, R¹, and R² are as defined above.

When $R^{12}$ is $N_3$, the derivatized macromolecule $Z—R^{13}$ may be conjugated to the compounds of formula (2) through $R^{13}$=CCH, using conditions for "click chemistry", a 1,3-dipolarcyclo addition reaction, to form a 1,2,3-triazole linkage in W=$(CH_2)_n$-triazolyl or

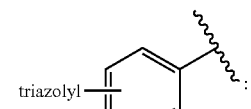

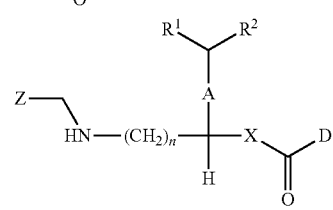

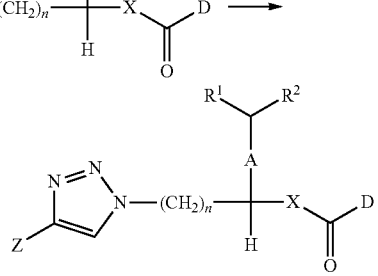

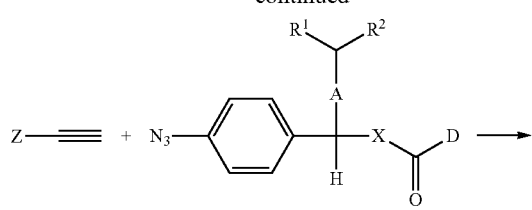

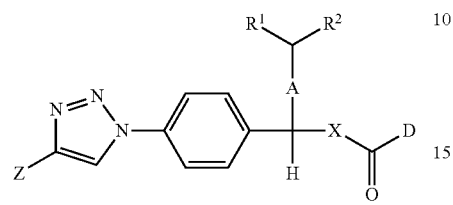

wherein Z, X, A, D, $R^1$, and $R^2$ are as defined above.

When $R^{12}$ is SH, the derivatized macromolecule Z—$R^{13}$ is conjugated to the compounds of formula (1) or (2) through $R^{13}$=maleimide or epoxide to form L'=$(CH_2)_n$-(hydroxyethylthio),

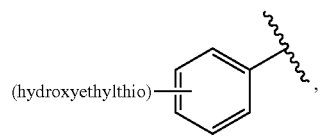

$(CH_2)_n$-(succinimidoylthio), or

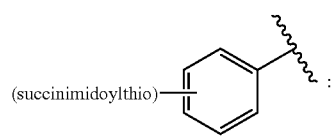

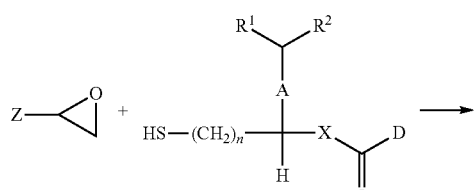

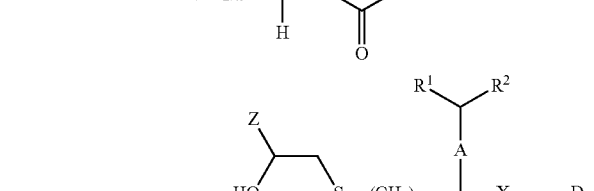

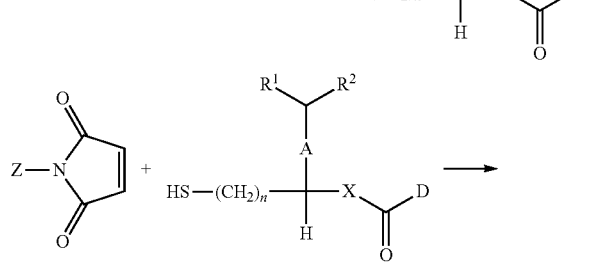

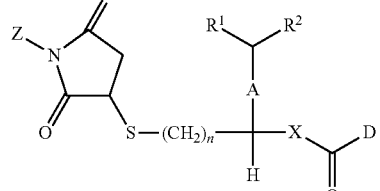

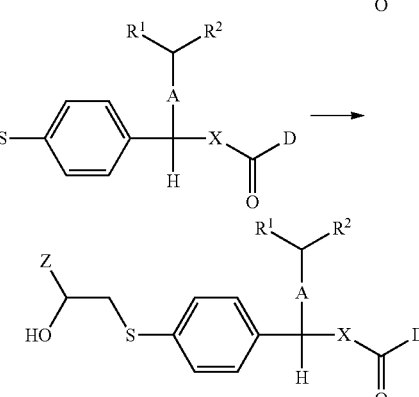

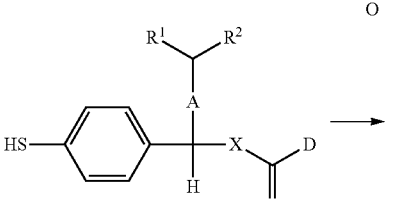

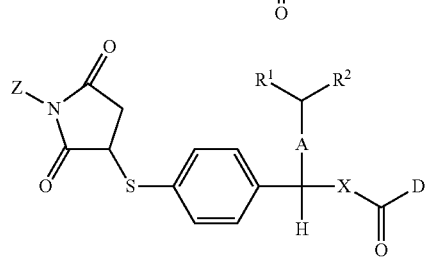

wherein Z, X, A, D, $R^1$, and $R^2$ are as defined above.

When $R^{12}$ is COOH, the derivatized macromolecule Z—$R^{13}$ is conjugated to the compounds of formula (1) or (2) through $R^{13}$=amine using a condensing agent such as a carbodiimide to give L'=$(CH_2)_n$—CONH or

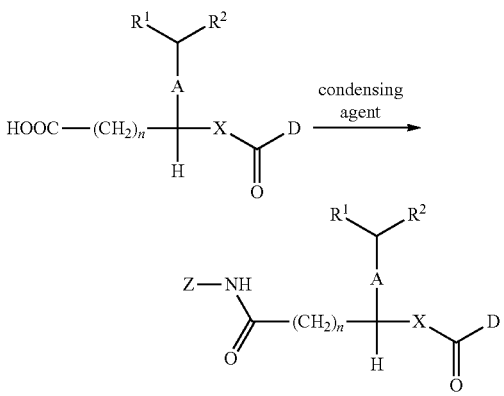

Z—NH₂ +

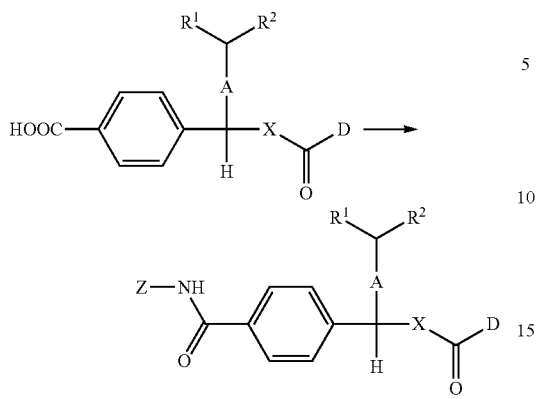

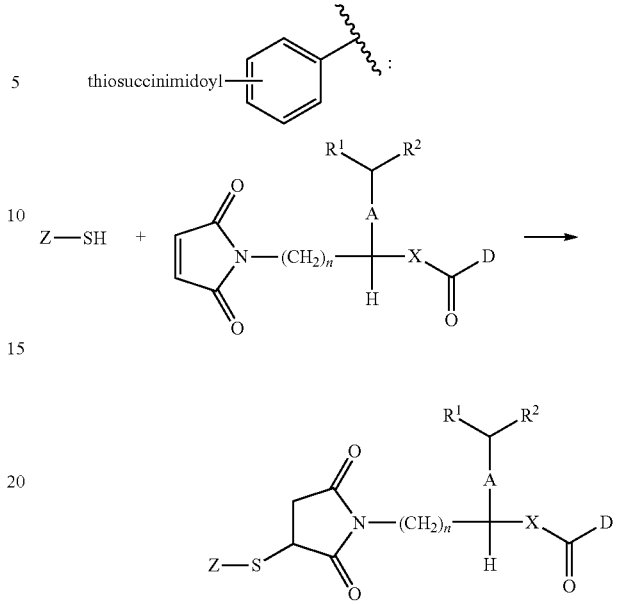

wherein Z, X, A, D, R¹, and R² are as defined above.

When $R^{12}$ is CCH, the derivatized macromolecule $Z-R^{13}$ is conjugated to the compounds of formula (1) or (2) through $R^{13}=N_3$ using "click-chemistry" to form a 1,2,3-triazole linkage in $L'=(CH_2)_n$-triazolyl or

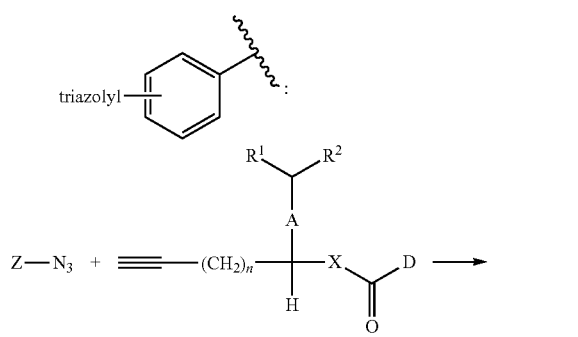

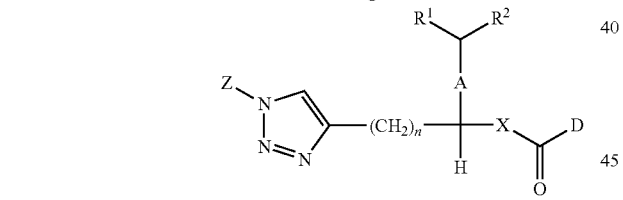

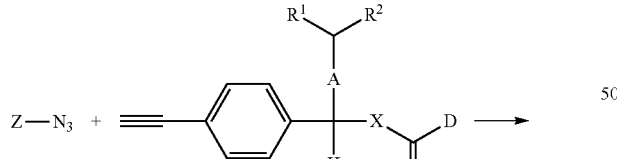

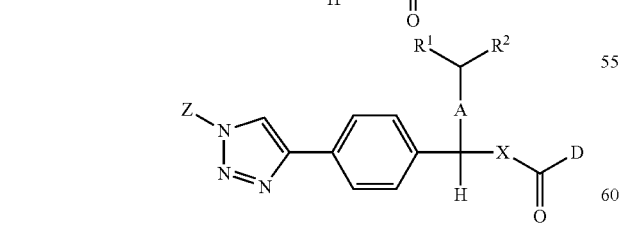

wherein Z, X, A, D, R¹, and R² are as defined above.

When $R^{12}$ is maleimido, the derivatized macromolecule $Z-R^{13}$ is conjugated to the compounds of formula (2) through $R^{13}=SH$ to give $L'=(CH_2)_n$-succinimidoylthio or

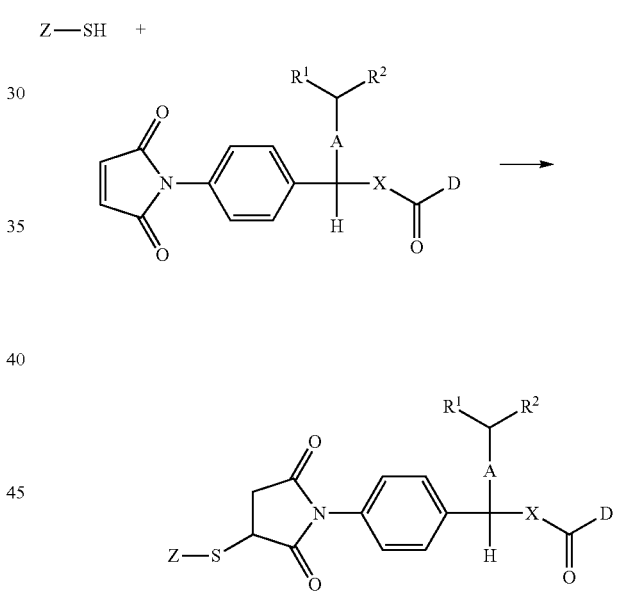

wherein Z, X, A, D, R¹, and R² are as defined above.

In one embodiment of the invention, L is a group having the formula

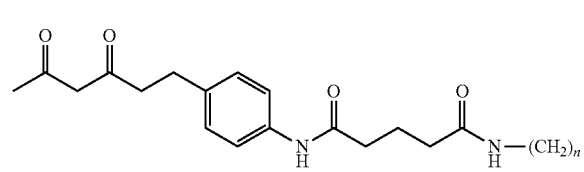

wherein n=1-6 and Z is an antibody comprising a reactive lysine residue such that $R^{13}=NH_2$. In this embodiment, conjugation of the prodrug and macromolecule provides an enamino-ketone linkage:

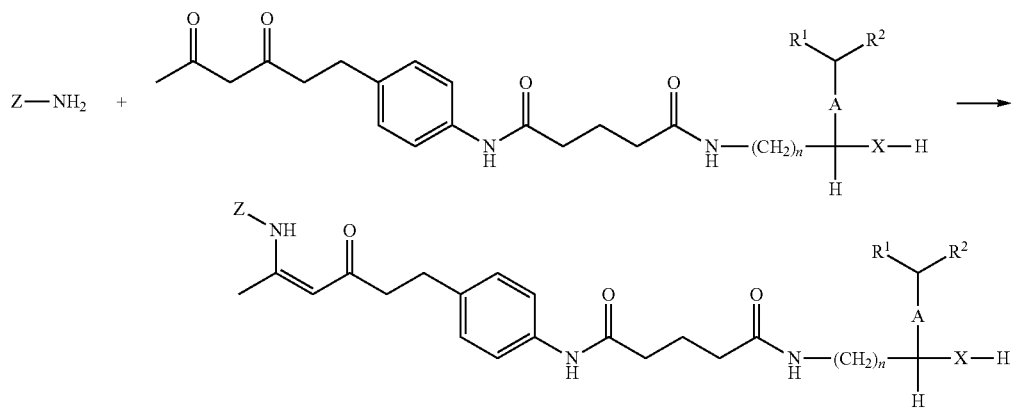

In some embodiments, the drug-macromolecule conjugates of formula (3) have the formula:

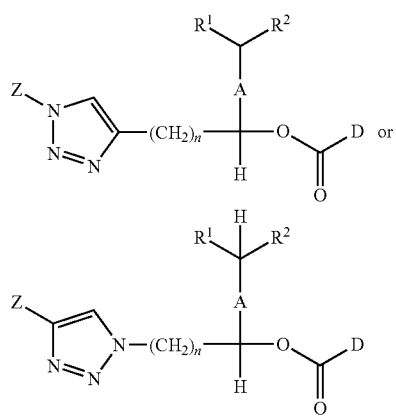

where $R^1$, $R^2$, Z, A and D are as above-defined, and n is 1-6.

In one embodiment, the conjugates of formula (3) have the more specific formula (3a)

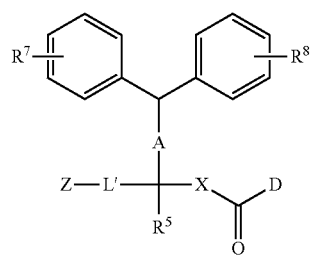

(3a)

wherein
Z is the residue of a macromolecule;
D is the residue of a drug molecule;
X is O or S;
L' is the residue of a linking group;
A is alkenyl ($C_2$), aryl, or absent; and
$R^7$ and $R^8$ are each independently H, an electron-donating group, or an electron-withdrawing group, wherein $R^7$ and $R^8$ in the form of non-hydrogen substituents may be present at 1-5 positions, preferably 3 or less positions on the rings to which they are bound, and $R^5$ is H or alkyl ($C_{1-6}$).

In some embodiments of formula (3a), Z and L' are as described above, and/or X is O, and/or A is absent or is alkenyl ($C_2$).

The compounds of formula (3a) are illustrated by:

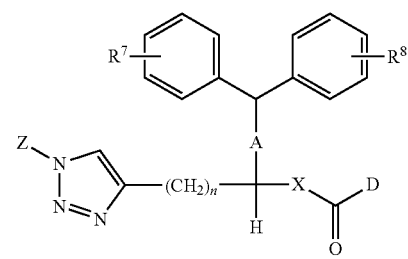

including examples that include:

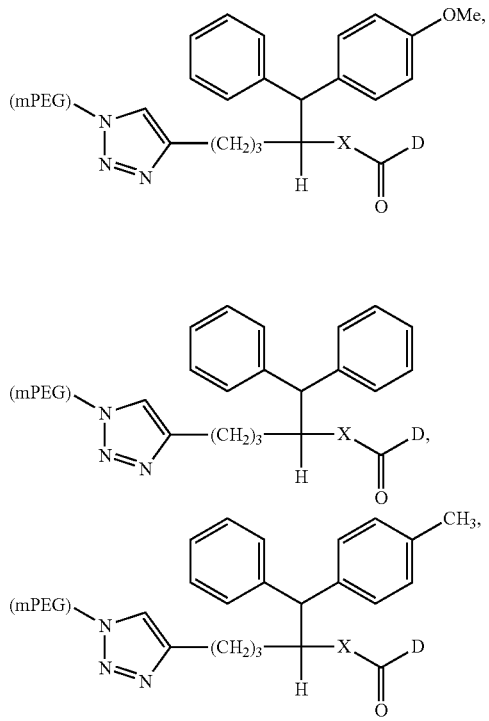

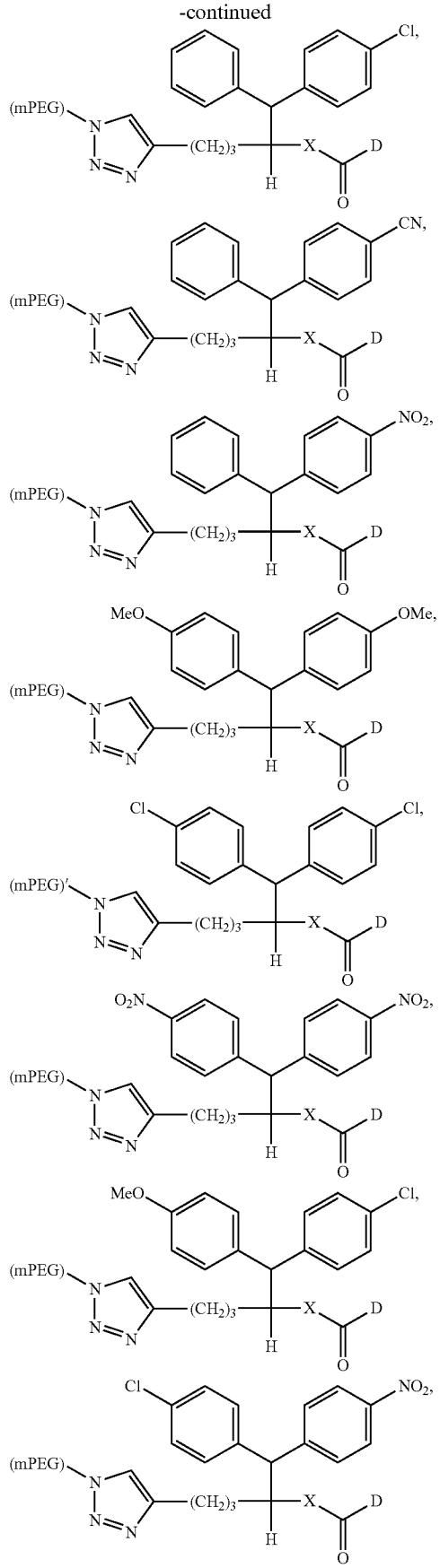

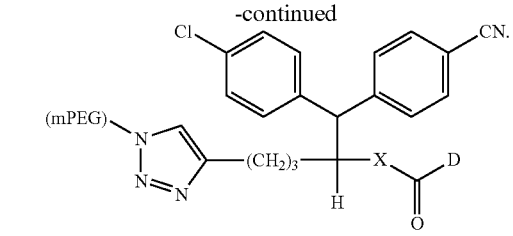

In another embodiment, the drug-macromolecule conjugates of formula (3) have the more specific formula (3b)

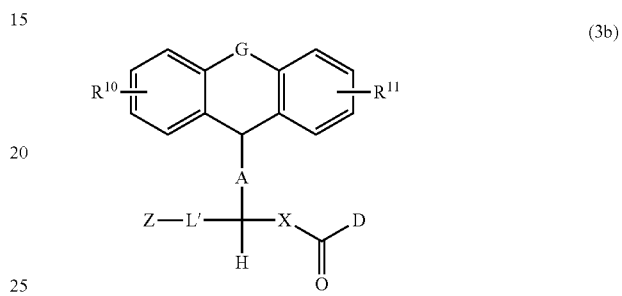

(3b)

wherein
Z is the residue of a macromolecule;
D is the residue of a drug molecule;
X is of O or S;
L' is the residue of a linking group;
A is alkenyl ($C_2$), aryl, or absent;
G is a bond C=O, O, S, SO, $SO_2$, $CX_2$ or $CX_2CX_2$, wherein each X is independently H or Cl and
$R^{10}$ and $R^{11}$ are each independently H, an electron-donating group, or an electron-withdrawing group, wherein each of $R^{10}$ and $R^{11}$ may be present at 1-4 positions, preferably 2 or fewer positions on the rings to which they are bound.

In certain embodiments of the invention, the drug-macromolecule conjugates have the formula (3b) wherein Z and L' are as exemplified above.

In the formula (3b) X may be O, and/or wherein A is absent, or is alkenyl ($C_2$).

In particular embodiments of the invention, the drug-macromolecule conjugates of formula (3b) have the more specific formula:

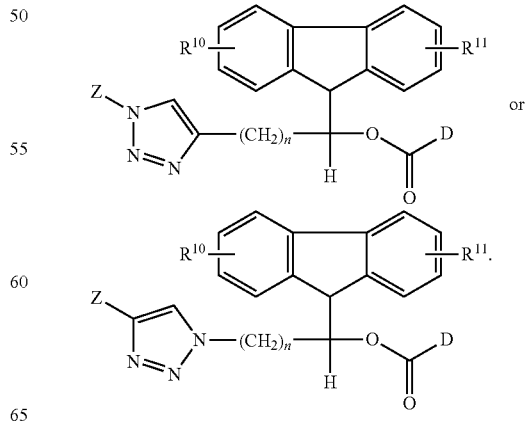

Illustrative embodiments of the invention, the drug-macromolecule conjugates of formula (3b) include
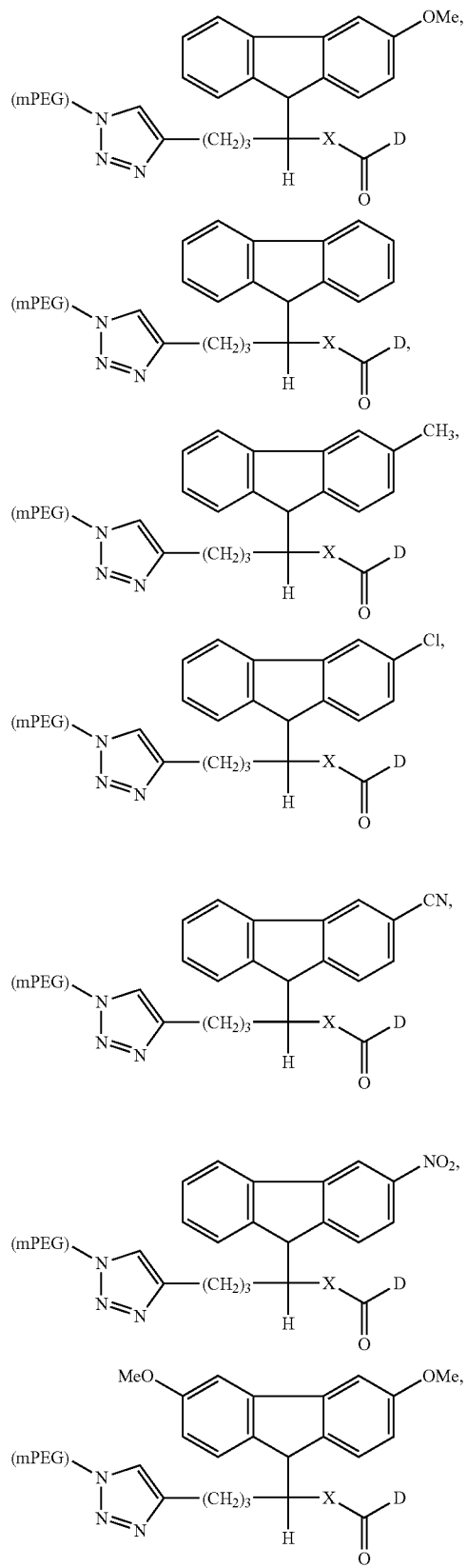
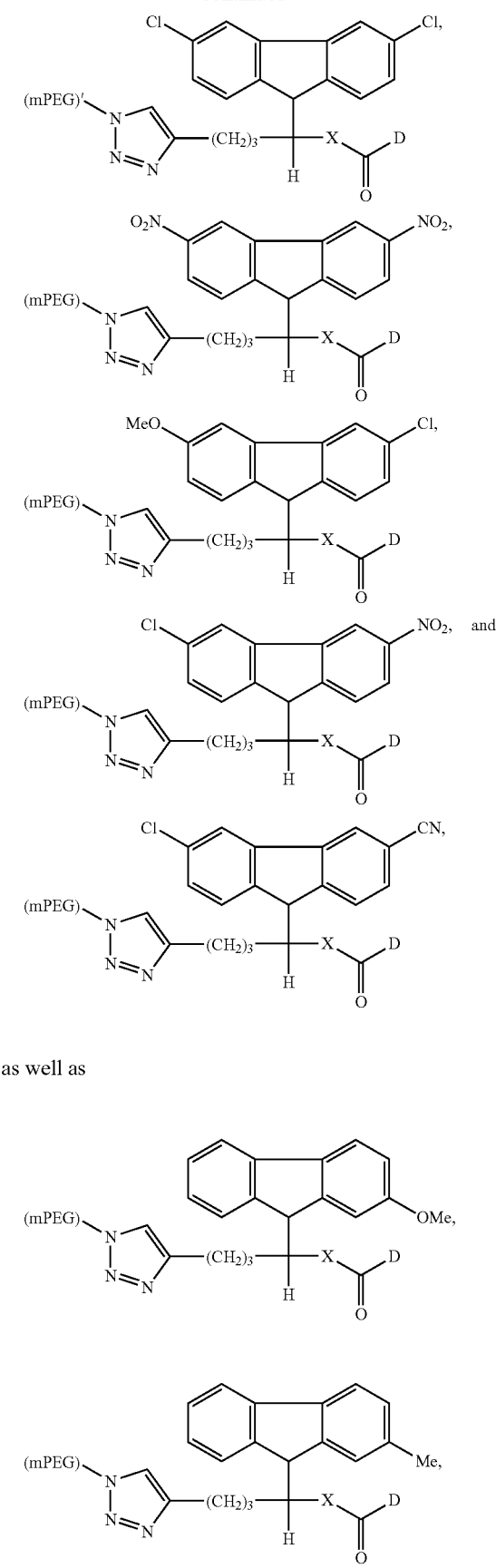
as well as

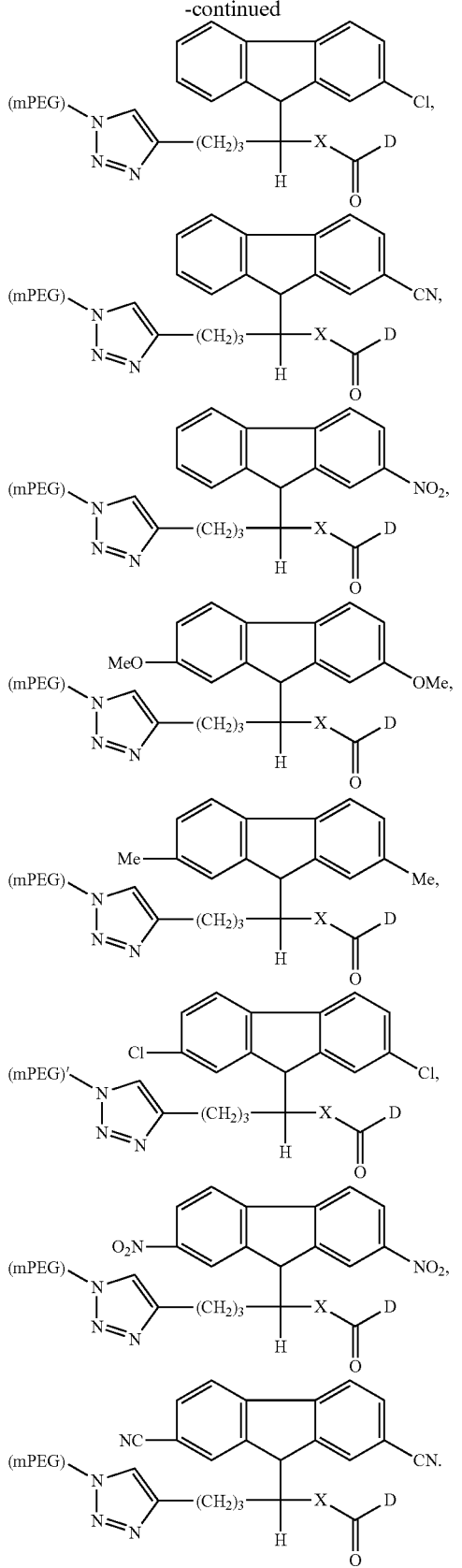

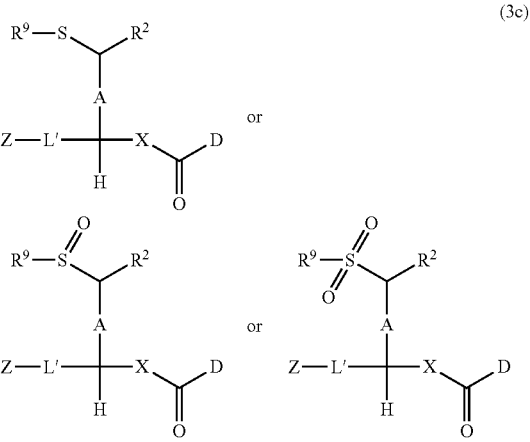

wherein, as above
Z is the residue of a macromolecule;
D is the residue of a drug molecule;
X is O or S;
L' is the residue of a linking group;
A is alkenyl ($C_2$), aryl, or absent;
$R^2$ is H, aryl, substituted aryl, heteroaryl, substituted heteroaryl, alkenyl, alkynyl, CN, $NO_2$, $COR^3$, $SOR^3$ or $SO_2R^3$: and
$R^9$ is alkyl, substituted alkyl, aryl, substituted aryl, heteroaryl, substituted heteroaryl, alkenyl, or alkynyl, and wherein $R^2$ and $R^9$ may be connected to form a cyclic structure.

The conjugates of formula (3c) may comprise embodiments of Z and L' illustrated above.

In some embodiments, of formula (3c) X is O, and/or A is absent, or is alkenyl ($C_2$).

The drug-macromolecule conjugates of formula (3c) may include

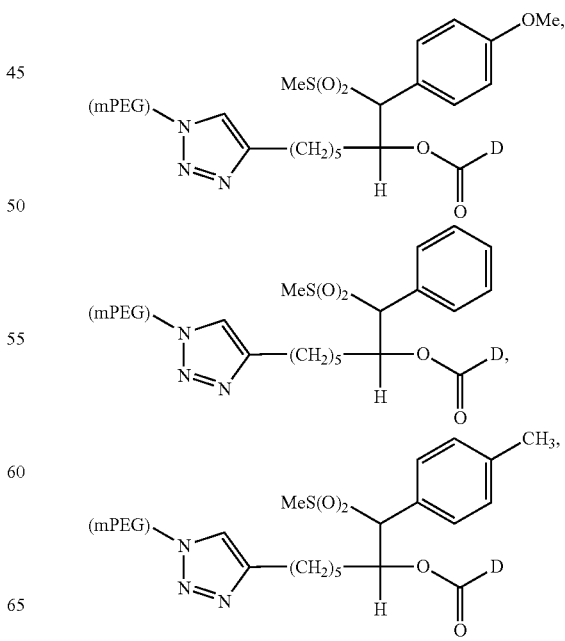

In another embodiment of the invention, conjugates of formula (3) have the formula (3c)

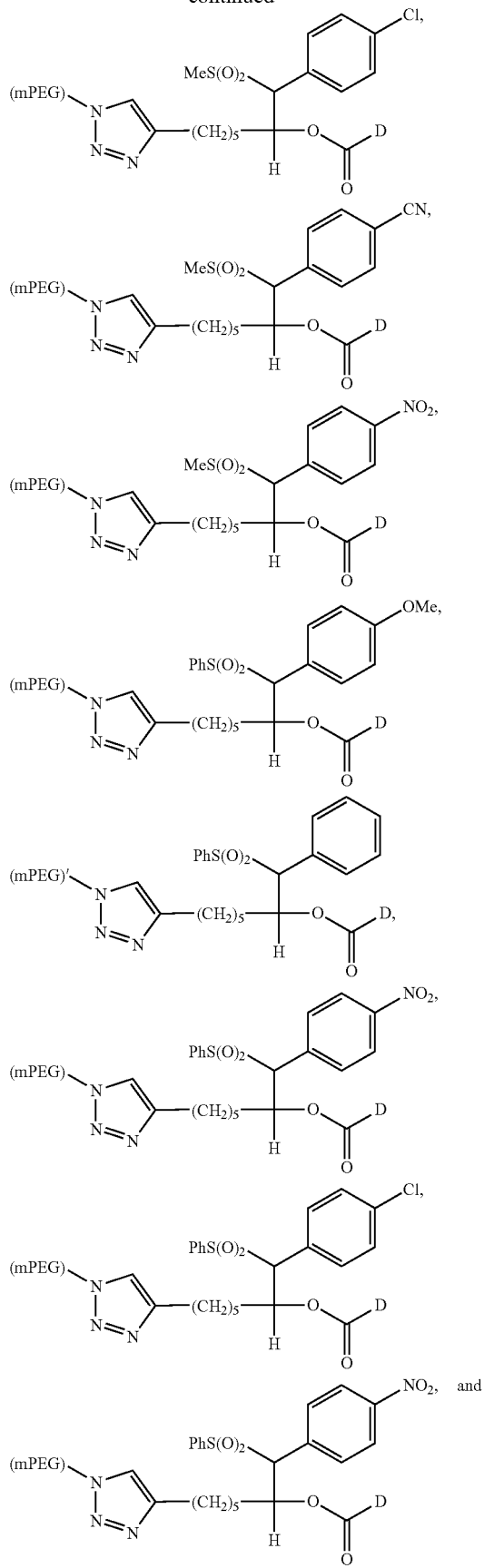

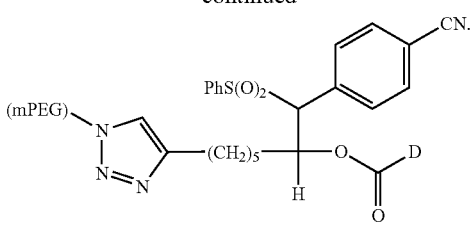

In each of the exemplified molecules, a non-hydrogen substituent may be present at 1-5 positions, preferably 3 or less positions on the phenyl ring shown.

In another embodiment, the conjugates of formula (3) have the more specific formula (3d)

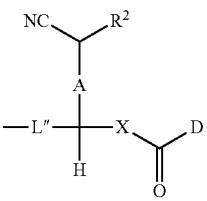

(3d)

wherein

Z is the residue of a macromolecule;

D is the residue of a drug molecule;

X is O or S;

L' is the residue of a linking group;

A is alkenyl ($C_2$), aryl, or absent; and $R^2$ is H, aryl, substituted aryl, heteroaryl, substituted heteroaryl, alkenyl, alkynyl, CN, $NO_2$, $COR^3$, $SOR^3$ or $SO_2R^3$.

The drug-macromolecule conjugates have the formula (3d) may include embodiments of Z and L' as listed above.

Formula (3d) includes embodiments wherein X is O, and/or wherein A is absent, or is alkenyl ($C_2$).

In certain particular embodiments of the invention, the drug-macromolecule conjugates of formula (3d) includes

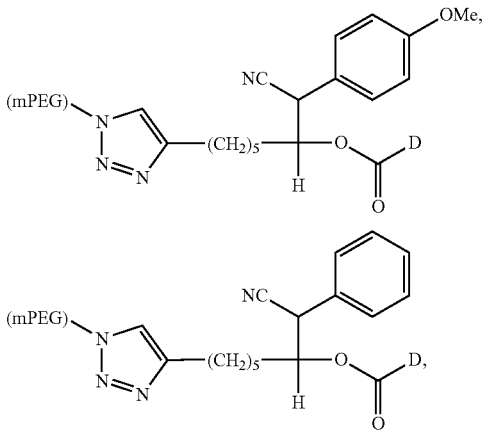

-continued

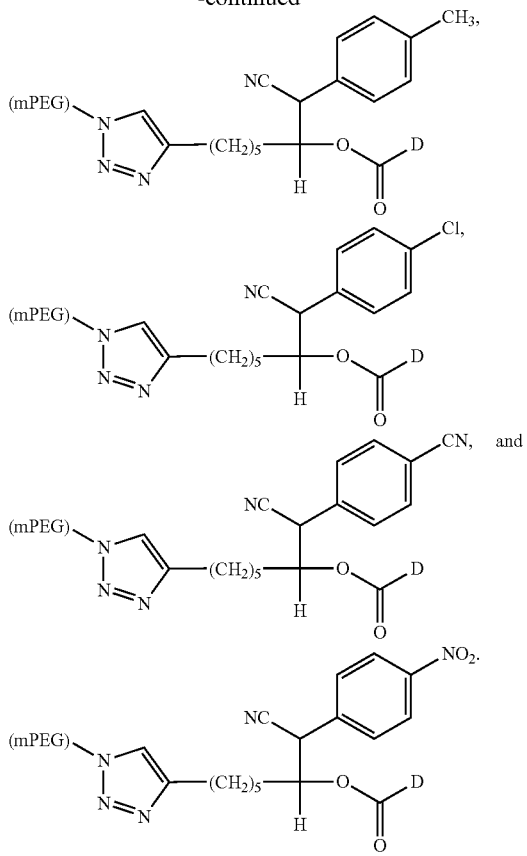

In another embodiment, the conjugates of formula (3) have the more specific formula (3e)

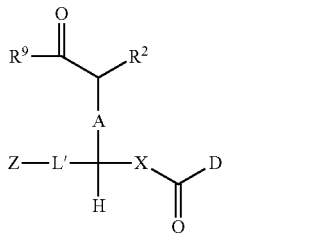

(3e)

wherein
Z is the residue of a macromolecule;
D is the residue of a drug molecule;
X is O or S;
L' is the residue of a linking group;
A is alkenyl ($C_2$), aryl, or absent;
$R^2$ is H, aryl, substituted aryl, heteroaryl, substituted heteroaryl, alkenyl, alkynyl, CN, $NO_2COR^3$, $SOR^3$ or $SO_2R^3$; and
$R^9$ is alkyl, substituted alkyl, aryl, substituted aryl, heteroaryl, substituted heteroaryl, alkenyl, or alkynyl, and wherein $R^2$ and $R^9$ may be connected to form a cyclic structure.

The conjugates of formula (3e) contain embodiments of Z and L' as listed above.

In formula (3e) X may be O, and/or A is absent, or is alkenyl ($C_2$).

In certain particular embodiments of the invention, the drug-macromolecule conjugates of formula (3e) include

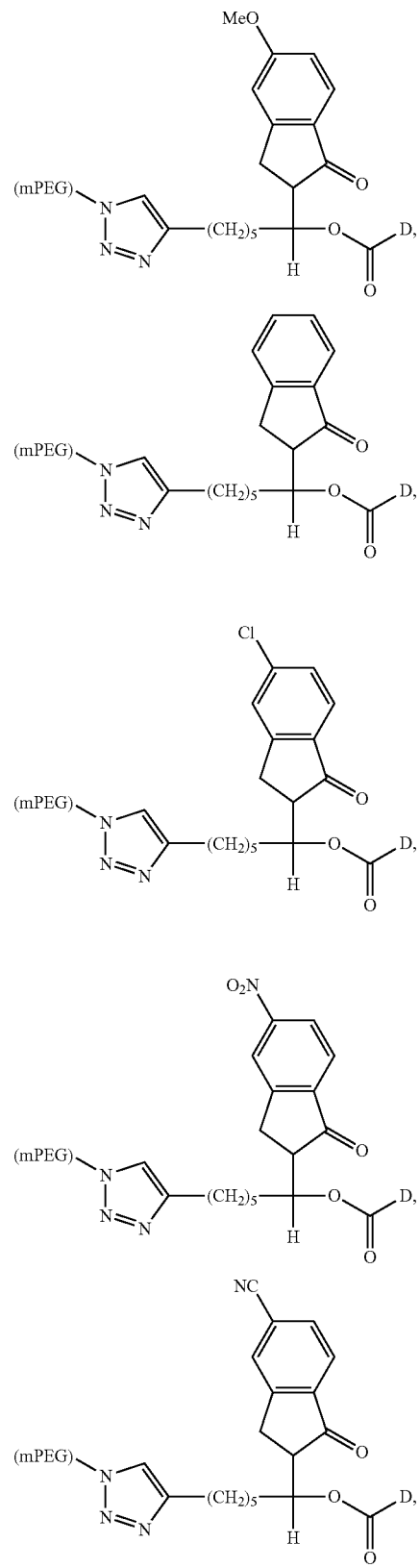

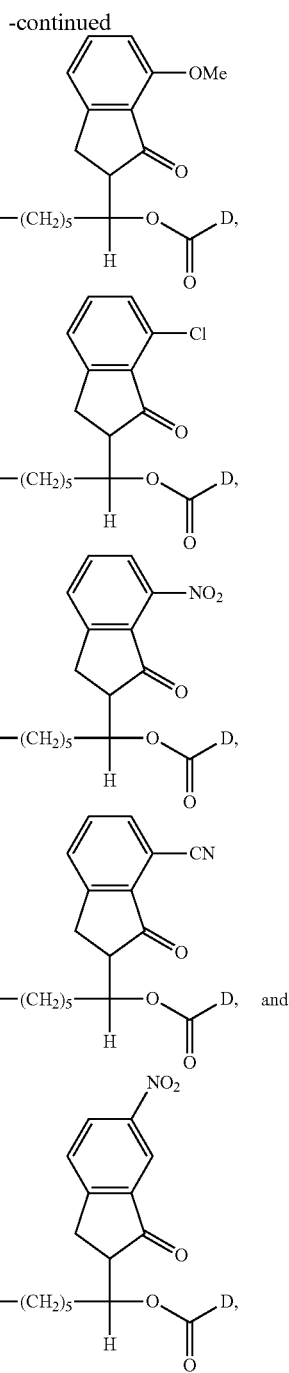

The foregoing illustrations of formulas (3a)-(3e) further include embodiments wherein m formula (3) is 2-10, including all intervening integers, and any rings showing non-hydrogen substituents may be substituted at multiple positions thereon. The substituents may be the same or different.

Pharmaceutical Compositions

The invention provides pharmaceutical and veterinary compositions comprising compounds of formulas (2) or (3) or pharmaceutically acceptable salts thereof or mixtures thereof and a pharmaceutically acceptable carrier. Any suitable route of administration of drugs to humans and animals is envisaged by the invention, for example via conventional injectable, implantable, oral, intraocular, intrathecal, rectal or topical administration. These preparations can be prepared by conventional methods known to those skilled in the art, for example as described in *Remington's Pharmaceutical Science*, A. R. Gennaro, ed., 17th edition, 1985, Mack Publishing Company, Easton, Pa., USA.

Subjects that may be treated with the compounds of formula (2) or (3) and compositions thereof include humans, veterinary animals, livestock and laboratory animals such as mice and rats.

The compositions may contain mixtures comprising two or more compounds of formula (3) or of formula (2). In one embodiment, the mixture comprises two or more compounds of formula (2) or (3), wherein each compound of formula (2) or (3) has the same drug D but a different rate of drug release under physiological conditions, thus providing a tailored drug release profile for drug D.

In another embodiment, the mixture comprises two or more compounds of formula (2) or (3), wherein each compound of formula (2) or (3) has a different drug D, and optionally a different rate of drug release for each drug D under physiological conditions, thus providing tailored combination therapy. In addition to controlling the release of a single drug, the invention can thus be used to control the release rates—and thus steady state concentrations and durations of action—of two or more drugs. Hence, for combinations of two drugs one can optimize the concentration and duration of both drugs. In one embodiment, an optimal conjugate for a first drug A is experimentally determined. Such an optimal conjugate is characterized as having an optimal drug concentration versus time profile (i.e., optimal drug concentrations and length of exposure). Using the optimized conjugate of the first drug A together with conjugates of the second drug B, each conjugate of drug B having a different drug release profile, the most effective combination is then determined experimentally. A converse experiment may then be undertaken, using the optimal conjugate of drug B together with multiple conjugates of the second drug A in order to verify that the optimal mixture has been determined.

In another embodiment, each of drugs A and B are made into conjugates that have a set of half-lives for release of the drugs from the conjugates (for example: 1, 2, 4, and 8 hr half-lives). Combinations of these conjugates that span all the possible permutations of conjugates of drug A and B are then tested.

In one particular embodiment of the invention, GLP-1 or an analogue thereof, for example an exendin, is conjugated to form a first drug-macromolecule conjugate of formula (3), and gastrin is conjugated to form a second drug-macromolecule conjugate of formula (3). In another particular embodiment of the invention, insulin is conjugated to form a first drug-macromolecule conjugate of formula (3), and insulin C-peptide is conjugated to form a second drug-macromolecule conjugate of formula (3).

The invention is illustrated but not limited by the examples outlined below.

Example 1

General Procedure, Formula (1), A=Absent, X=O

A solution of $R^1R^2CH_2$ (1.0 equivalent) in tetrahydrofuran (THF) is added to a solution of lithium diisopropylamide (LDA) or butyllithium at −78° C. (1.0 equivalent). The mixture is allowed to warm slowly to 0° C., then recooled to −78° C. prior to the addition of aldehyde L-CHO (1.0 equivalent). After 30 minutes, the mixture is allowed to warm slowly to ambient temperature, quenched by addition of saturated aqueous $NH_4Cl$, and extracted with ether. The extract is

Example 2

General Procedure, Formula (1), A=Absent, X=S

A solution of the compound of formula (1) wherein A is absent and X=O (1.0 equivalent) in THF is added to a solution of 1 M lithium bis(trimethylsilylamide) (LiHMDS) (1.0 equivalent) at −78° C. After 15 minutes, a solution of p-toluenesulfonyl chloride (1.0 equivalent) is added, and the mixture is allowed to warm slowly to ambient temperature, quenched by addition of saturated aqueous $NH_4Cl$, and extracted with ether. The extract is washed sequentially with 1 N HCl, saturated aqueous $NaHCO_3$, and brine, then dried over $MgSO_4$, filtered, and evaporated. The resulting crude tosylate is dissolved in isopropanol and reacted with aqueous sodium thiosulfate at 50° C. to form the Bunte salt, which is hydrolyzed by treatment with aqueous HCl. The mercaptan product is purified by chromatography on silica gel.

Example 3

General Procedure, Formula (1), A=Alkenyl ($C_2$), X=O, L=Substituted Aryl

A solution of $R^1R^2CH_2$ (1.0 equivalent) in tetrahydrofuran (THF) is added to a solution of lithium diisopropylamide (LDA) or butyllithium at −78° C. (1.0 equivalent). The mixture is allowed to warm slowly to 0° C., then recooled to −78° C. prior to the addition of methyl 3-(dimethylamino)propenoate (1.0 equivalent). The mixture is allowed to warm slowly to ambient temperature, quenched by addition of 1 N HCl, and extracted with ether. The extract is washed sequentially with 1 N HCl, saturated aqueous $NaHCO_3$, and brine, then dried over $MgSO_4$, filtered, and evaporated. The product ester is purified by chromatography on silica gel.

A solution of the ester (1.0 equivalent) in THF is treated with excess lithium aluminum hydride, then quenched by addition of oxalic acid and extracted with ether. The extract is washed sequentially with 1 N HCl, saturated aqueous $NaHCO_3$, and brine, then dried over $MgSO_4$, filtered, and evaporated. The product alcohol is purified by chromatography on silica gel.

The alcohol from above (1.0 equivalent) is oxidized to the aldehyde by reaction with Dess-Martin periodinane (1.5 equivalent) in dichloromethane solution. The solution is filtered and washed sequentially with 1 N HCl, saturated aqueous $NaHCO_3$, and brine, then dried over $MgSO_4$, filtered, and evaporated. The product aldehyde is purified by chromatography on silica gel.

The aldehyde from above is reacted with the substituted arylboronic acid as described in *Organic Letters* (2005) 7:4153-4155 (incorporated herein by reference). Thus, a mixture comprising the aldehyde (1.0 equivalent), arylboronic acid (2.0 equivalents), $Cs_2CO_3$ (2.0 equivalents), $Pd_2(dba)_3 \cdot CHCl_3$ (0.025 equivalent), and $Ph_3P$ (0.05 equivalent) in toluene is heated at 80° C. for 24 hours. After cooling to ambient temperature, the mixture is concentrated and the product is purified by chromatography on silica gel.

Example 4

General Procedure, Formula (1), A=Alkenyl ($C_2$), X=S, L=Substituted Aryl

The product of Example 3 is converted to the corresponding compound wherein X=S using the procedure of Example 2.

Example 5

General Procedures, Activation of Compounds of Formula (1), X=O as the 4-Nitrophenylcarbonates A solution of the compound of formula (1) (1.0 equivalent) in THF is added to a 1.0 M solution of LiHMDS (1.0 equivalent) in THF at −78° C. After 15 minutes, a solution of bis(4-nitrophenyl) carbonate (1.5 equivalent) is added. The mixture is allowed to warm slowly to ambient temperature, quenched by addition of 1 N HCl, and extracted with ether. The extract is washed sequentially with 1 N HCl, water, and brine, then dried over $MgSO_4$, filtered, and evaporated. The product 4-nitrophenyl carbonate is purified by chromatography on silica gel.

Example 6

General Procedures, Activation of Compounds of Formula (1), X=O as the N-Hydroxysuccinimidoyl Carbonates Via Intermediate Chloroformates A solution of the compound of formula (1) (1 equivalent) in chloroform is treated with triphosgene (5 equivalents) for 24 hours at ambient temperature. The solvent is removed by evaporation to provide the crude chloroformate.

The chloroformate is dissolved in THF and treated with N-hydroxysuccinimide (4 equivalents) and 2.6-lutidine (6 equivalents) at ambient temperature. When complete as judged by HPLC analysis, the mixture is diluted with ethyl acetate and washed sequentially with 1 N HCl, water, and brine, then dried over $MgSO_4$, filtered, and evaporated. The product N-hydroxysuccinimoyl carbonate is purified by HPLC chromatography.

Example 7

General Procedure, Formula (2), X=O, D=Peptide by Conjugation

A solution of the peptide in aqueous buffer, pH 7.5, is treated with a solution of the activated compound of Example 5 or Example 6 (1 equivalent) in DMSO. The pH is maintained as necessary by the addition of 1 N NaOH. The reaction progress is monitored by HPLC. When judged complete, the mixture is purified by preparative HPLC.

Example 8

General Procedure, Formula (2), X=O, D=Nucleic Acid by Conjugation

A solution of the nucleic acid in aqueous buffer, pH 7.5, is treated with a solution of the activated compound of Example 5 or Example 6 (1 equivalent) in DMSO. The pH is maintained as necessary by the addition of 1 N NaOH. The reaction progress is monitored by HPLC. When judged complete, the mixture is purified by preparative HPLC.

Example 9

General Procedure, Formula (2), X=O, D=Peptide by Synthesis

The peptide is synthesized using standard conditions known in the art, for example using FMOC chemistry. Upon coupling the final amino acid, the terminal FMOC protecting group is removed by treatment under standard conditions. The resin-bound peptide is then reacted with excess compound of Example 5 or Example 6 to cap the N-terminus. The peptide is then deprotected and cleaved from the resin using TFA/triethylsilane, and purified by reversed phase HPLC.

Example 10

General Procedure, Formula (3), X=OH, D=Peptide, Z=mPEG

A compound of formula (1) wherein X=O, A is absent, and L=HCC—$(CH_2)_n$ wherein n=0-6 is prepared according to the method of Example 1 using the appropriate terminal alkynyl aldehyde HCC—$(CH_2)_n$CHO. This compound is activated according to the method of Example 5 or Example 6, and coupled to peptide D according to the method of Example 7 or Example 9 to provide a compound of formula (2) wherein X=O, D=peptide, and L=HCC—$(CH_2)_n$.

Alternatively, a compound of formula (1) wherein X=O, A is absent, and L=ethynylphenyl is prepared according to the method of Example 1 using the appropriate alkynylbenzaldehyde. This compound is activated according to the method of Example 5 or Example 6, and coupled to peptide D according to the method of Example 7 or Example 9 to provide a compound of formula (2) wherein X=O, D=peptide, and L=alkynylphenyl.

A THF solution of mPEG-$N_3$ (1 equivalent) and the above-described alkynyl compound of formula (2) (1 equivalent) is treated with aqueous $CuSO_4 \cdot 5H_2O$ (0.1 equivalent) and sodium ascorbate (0.5 equivalent) is stirred 24 hours at ambient temperature. The mixture is lyophilized, then purified by preparative reversed-phase HPLC.

Example 11

(4-ethynylphenyl)(9H-fluoren-9-yl)methanol

Formula (1): A=Absent; X=O;
$R^1R^2CH$=9-Fluorenyl; L=4-Ethynylphenyl

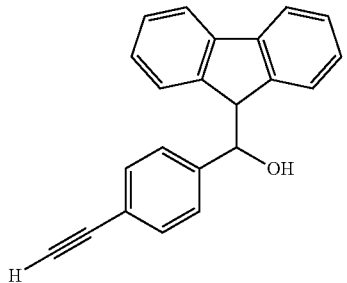 [SMILES: C#Cc1ccc(C(O)C2c3ccccc3-c3ccccc32)cc1]

A solution of fluorene (1.0 equivalent) in tetrahydrofuran (THF) is added to a solution of lithium diisopropylamide (LDA) at −78° C. (1.0 equivalent). The mixture is allowed to warm slowly to 0° C., then recooled to −78° C. prior to the addition of 4-ethynyl-benzaldehyde (1.0 equivalent). After 30 minutes, the mixture is allowed to warm slowly to ambient temperature, quenched by addition of saturated aqueous $NH_4Cl$, and extracted with ether. The extract is washed sequentially with 1 N HCl, saturated aqueous $NaHCO_3$, and brine, then dried over $MgSO_4$, filtered, and evaporated. The product is purified by chromatography on silica gel.

Example 12

1-(3-(tert-butoxycarbonylamino)phenyl-3-(9H-fluoren-9-yl)allyl alcohol

Formula (1): A=CH═CH; X=O;
$R^1R^2CH$=9-Fluorenyl;
L=3-(N—BOC-Amino)Phenyl

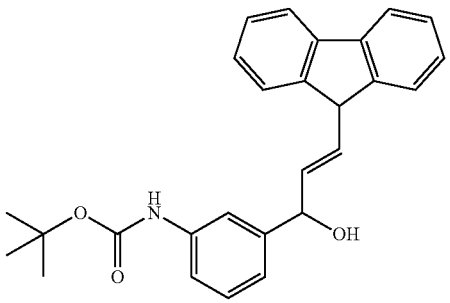 [SMILES: CC(C)(C)OC(=O)Nc1cccc(C(O)/C=C/C2c3ccccc3-c3ccccc32)c1]

A solution of fluorene (1.0 equivalent) in tetrahydrofuran (THF) is added to a solution of lithium diisopropylamide (LDA) at −78° C. (1.0 equivalent). The mixture is allowed to warm slowly to 0° C., then recooled to −78° C. prior to the addition of methyl 3-(dimethylamino)propenoate (1.0 equivalent). The mixture is allowed to warm slowly to ambient temperature, quenched by addition of 1 N HCl, and extracted with ether. The extract is washed sequentially with 1 N HCl, saturated aqueous $NaHCO_3$, and brine, then dried over $MgSO_4$, filtered, and evaporated. The product ester is purified by chromatography on silica gel.

A solution of the ester (1.0 equivalent) in THF is treated with excess lithium aluminum hydride, then quenched by addition of oxalic acid and extracted with ether. The extract is washed sequentially with 1 N HCl, saturated aqueous $NaHCO_3$, and brine, then dried over $MgSO_4$, filtered, and evaporated. The product alcohol is purified by chromatography on silica gel.

The alcohol from above (1.0 equivalent) is oxidized to the aldehyde by reaction with Dess-Martin periodinane (1.5 equivalent) in dichloromethane solution. The solution is filtered and washed sequentially with 1 N HCl, saturated aqueous NaHCO₃, and brine, then dried over MgSO₄, filtered, and evaporated. The product aldehyde is purified by chromatography on silica gel.

A mixture comprising the above-described aldehyde (1.0 equivalent), 3-(N—BOC-amino)phenylboronic acid (2.0 equivalents), Cs₂CO₃ (2.0 equivalents), Pd₂(dba)₃.CHCl₃ (0.025 equivalent), and Ph₃P (0.05 equivalent) in toluene is heated at 80° C. for 24 hours. After cooling to ambient temperature, the mixture is concentrated and the product is purified by chromatography on silica gel.

Example 13

(4-ethynylphenyl)(9H-fluoren-9-yl)methyl 4-nitrophenyl carbonate

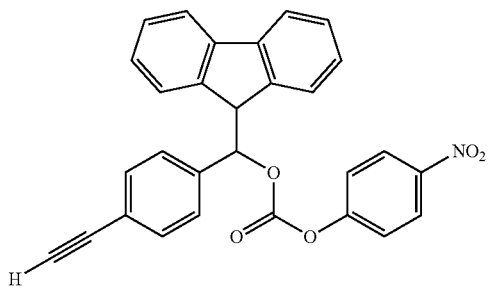 [SMILES: C#Cc1ccc(C(OC(=O)Oc2ccc([N+](=O)[O-])cc2)C2c3ccccc3-c3ccccc32)cc1]

A solution of (4-ethynylphenyl)(9H-fluoren-9-yl)methanol (1.0 equivalent) in THF is added to a 1.0 M solution of LiHMDS (1.0 equivalent) in THF at −78° C. After 15 minutes, a solution of bis(4-nitrophenyl) carbonate (1.5 equivalent) is added. The mixture is allowed to warm slowly to ambient temperature, quenched by addition of 1 N HCl, and extracted with ether. The extract is washed sequentially with 1 N HCl, water, and brine, then dried over MgSO₄, filtered, and evaporated. The product 4-nitrophenyl carbonate is purified by chromatography on silica gel.

Example 14

1-(3-(tert-butoxycarbonylamino)phenyl)-3-(9H-fluoren-9-yl)allyl N-hydroxysuccinimidoyl carbonate

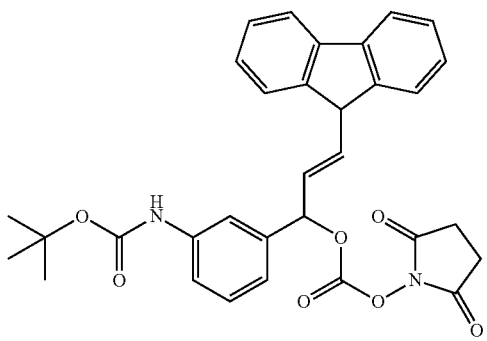 [SMILES: CC(C)(C)OC(=O)Nc1cccc(C(/C=C/C2c3ccccc3-c3ccccc32)OC(=O)ON2C(=O)CCC2=O)c1]

A solution of 1-(3-(tert-butoxycarbonylamino)phenyl)-3-(9H-fluoren-9-yl)allyl alcohol (1 equivalent) in chloroform is treated with triphosgene (5 equivalents) and pyridine (2 equivalents) for 24 hours at ambient temperature. The solvent is removed by evaporation to provide the crude chloroformate.

The chloroformate is dissolved in THF and treated with N-hydroxysuccinimide (4 equivalents) and 2,6-lutidine (6 equivalents) at ambient temperature. When complete as judged by HPLC analysis, the mixture is diluted with ethyl acetate and washed sequentially with 1 N HCl, water, and brine, then dried over MgSO₄, filtered, and evaporated. The product N-hydroxysuccinimidoyl carbonate is purified by HPLC chromatography.

Example 15

[(4-ethynylphenyl)(9H-fluoren-9-yl)methoxycarbonyl]-derivatized exendin-4

A solution of exendin-4 (HGEGTFTSDL SKQMEEEAVR LFIEWLKNGG PSSGAPPPS) in aqueous buffer, pH 7.5, is treated with a solution of the activated compound of Example 13 (1 equivalent) in DMSO. The pH is maintained as necessary by the addition of 1 N NaOH. The reaction progress is monitored by HPLC. When judged complete, the mixture is purified by preparative HPLC.

Example 16

N-[(4-ethynylphenyl)(9H-fluoren-9-yl)methoxycarbonyl]-exendin-4

The peptide sequence of exendin-4 (HGEGTFTSDL SKQMEEEAVR LFIEWLKNGG PSSGAPPPS) is synthesized using standard FMOC chemistry. Upon coupling the final histidine amino acid, the terminal FMOC protecting group is removed by treatment under standard conditions. The resin-bound peptide is then reacted with excess compound of Example 13 to cap the N-terminus. The peptide is then deprotected and cleaved from the resin using TFA/triethylsilane, and purified by reversed phase HPLC using standard methodology.

Example 17

N-[(4-(mPEG-triazolyl)phenyl)(9H-fluoren-9-yl)methoxycarbonyl]-exendin-4

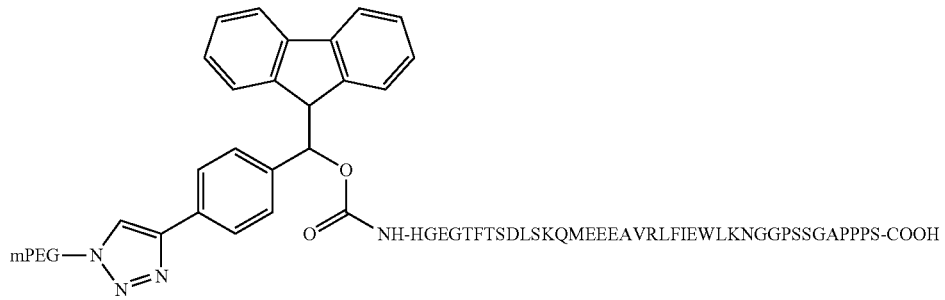

A THF solution of mPEG-$N_3$ (1 equivalent) and the alkynyl compound of Example 16 (1 equivalent) is treated with aqueous $CuSO_4 \cdot 5H_2O$ (0.1 equivalent) and sodium ascorbate (0.5 equivalent) is stirred 24 hours at ambient temperature. The mixture is dried, then purified by preparative reversed-phase HPLC.

Example 18

1-(3-(tert-butoxycarbonylamino)phenyl)-3-(9H-fluoren-9-yl)allyloxycarbonyl-derivatized exendin-4

A solution of exendin-4 (HGEGTFTSDLSKQMEEE-AVRLFIEWLKNGGPSS-GAPPPS) in aqueous buffer, pH 7.5, is treated with a solution of the activated compound of Example 14 (1 equivalent) in DMSO. The pH is maintained as necessary by the addition of 1 N NaOH. The reaction progress is monitored by HPLC. When judged complete, the mixture is purified by preparative HPLC.

Example 19

N-[1-(3-(tert-butoxycarbonylamino)phenyl)-3-(9H-fluoren-9-yl)allyloxycarbonyl]-exendin-4

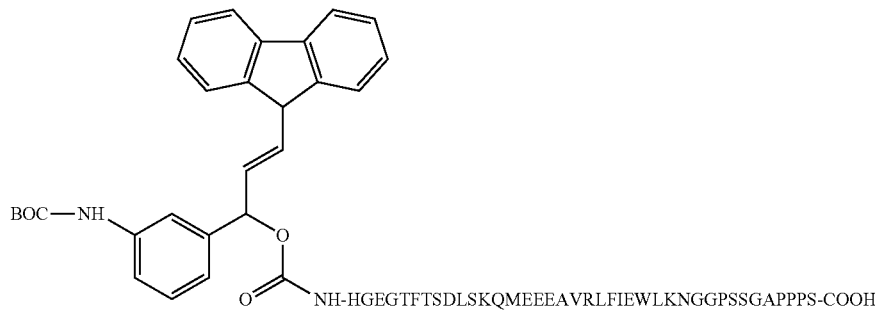

The peptide sequence of exendin-4 (HGEGTFTSDL-SKQMEEEAVRL-FIEWLKNGGPSSGAPPPS) is synthesized using standard FMOC chemistry. Upon coupling the final histidine amino acid, the terminal FMOC protecting group is removed by treatment under standard conditions. The resin-bound peptide is then reacted with excess compound of Example 14 to cap the N-terminus. The peptide is then deprotected and cleaved from the resin using TFA/triethylsilane, and purified by reversed phase HPLC using standard methodology.

Example 20

N-[1-(3-(mPEG-carboxamido)phenyl)-3-(9H-fluoren-9-yl)allyloxycarbonyl]-exendin-4

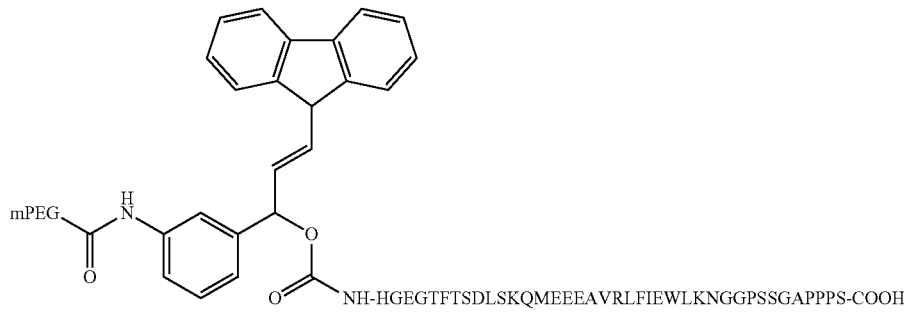

The compound of Example 19 is dissolved in TFA/triethylsilane to remove the tert-butoxycarbonyl group, then evaporated to dryness. The resulting compound is dissolved in acetonitrile and reacted with mPEG-carboxylate N-hydroxysuccinimide ester in the presence of pH 6 buffer. The mixture is stirred at ambient temperature overnight, then dried. The product is purified by reversed-phase HPLC.

Example 21

5-hexynal

Under a nitrogen atmosphere, 5-hexyn-1-ol (3 mL, 27.5 mmol, 1.0 Eq) was added to a 0° C. mixture of sodium acetate (4.5 g, 27.4 mmol, 2.0 equiv.) and $MgSO_4$ (1.48 g) in dry $CH_2Cl_2$ (50 mL), followed by pyridinium chlorochromate (PCC) (11.85 g, 27.5 mmol, 2.0 equiv.). The reaction mixture was stirred at room temperature for 3 hours, and ethyl ether ($Et_2O$) (20 mL) was added. The resulting mixture was filtered through a short pad of silica gel, and the residue was washed with 40 mL of $Et_2O$/petroleum ether (1:1). The clear filtrate was concentrated to half its original volume, then dried over molecular sieves and stored in refrigerator for the next step.

Example 22

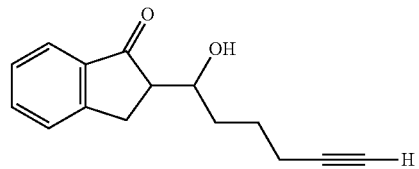 [SMILES: C#CCCCC(O)C1Cc2ccccc2C1=O]

Under the protection of $N_2$, n-Butyllithium (2.7 mL, 7.8 mmol) was added into the solution of N,N-diisopropylamine (1.1 mL, 7.8 mmol) in 20 ml of anhydrous tetrahydrofuran (THF) at 55° C., the reaction mixture was stirred for 15 min, and chilled to −78° C. Indanone (0.95 g, 7.2 mmol) in THF (10 mL) was added into the above mixture via cannula. After stirring at the same temperature 30 min, a solution of 5-hexynal was added into the flask and stirred for 3 hours. The reaction was quenched by addition of a solution of $NaHSO_4$ (1 g in 10 mL of water), and the reaction mixture was warmed to room temperature. The aqueous layer was extracted with ethyl acetate (EtOAc) (15 mL×2), and the combined organic solution was dried over $MgSO_4$ and concentrated under reduced pressure. The residue was purified by flash chromatography on silica gel to obtain the product as a red solid (0.52 g, yield 38.3%).

Example 23

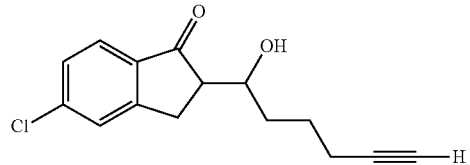 [SMILES: C#CCCCC(O)C1Cc2cc(Cl)ccc2C1=O]

Under a nitrogen atmosphere, n-butyllithium (2.5M in hexanes, 1.0 mL, 3.0 mmol) was added to a solution of N,N-diisopropylamine (0.42 mL, 3.0 mmol) in anhydrous tetrahydrofuran (THF) (6 mL) at 0° C. The resulting reaction mixture was stirred at the same temperature for 15 min, then cooled to −78° C. 5-Chloro-2,3-dihydroinden-1-one (0.5 g, 3.0 mmol) in THF (3 mL) was added. After stirring at −78° C. for 30 min, a solution of 5-hexynal was added. The reaction mixture was then stirred at −78° C. for 2 hours, quenched by addition of sat. aq. NH$_4$Cl, and warmed to room temperature. The aqueous phase was extracted with ethyl acetate (EtOAc), and the combined organic solution was washed with brine, dried over anhydrous MgSO$_4$, filtered, and concentrated under reduced pressure. The residue was purified by column chromatography on silica gel to obtain the desired product as pale yellow solid (0.29 g, yield 41.3%).

Example 24

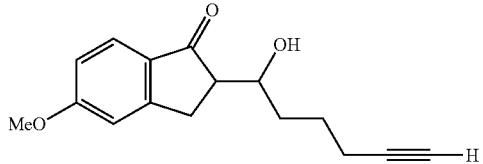

Under the protection of N$_2$, n-butyllithium (2.5 M in hexanes, 2.7 mL, 7.8 mmol) was added to a solution of N,N-diisopropylamine (1.1 mL, 7.8 mmol) in anhydrous THF (20 mL) at 0° C. The reaction mixture was stirred for 15 min and then was chilled to −78° C. 5-Methoxy-2,3-dihydroinden-1-one (1.17 g, 7.2 mmol) in THF (10 mL) was added into the above mixture via cannula. After stirring at the same temperature for 30 min, a solution of 5-hexynal (ca. 6 mmol) was added into the flask and the reaction mixture was stirred at −78° C. for 3 hours. The reaction was quenched by addition of a saturated solution of NH$_4$Cl (10 mL), and then warmed up to room temperature. The mixture was extracted with EtOAc (15 mL×2), and the combined organic solution was dried over MgSO$_4$, and concentrated under reduced pressure. The residue was purified by flash chromatography on silica gel to obtain the product as a white solid (0.58 g, yield 31.2%).

Example 25

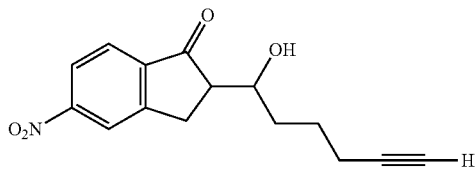 [SMILES: C#CCCCC(O)C1Cc2cc([N+](=O)[O-])ccc2C1=O]

Under the protection of N$_2$, n-butyllithium (2.5 M in hexanes, 0.39 mL, 1.13 mmol) was added to a solution of N,N-diisopropylamine (0.17 mL, 1.13 mmol) in anhydrous THF (4 mL) at 0° C. The reaction mixture was stirred at 0° C. for 20 min, chilled to −78° C., and 5-nitro-2,3-dihydroinden-1-one (0.2 g, 1.13 mmol) in THF (4 mL) was added by needle. After stirring at the same temperature for 30 min, a solution of 5-hexynal (ca. 1 mmol) was added, and then stirred for at −78° C. for 3 hours. The reaction was quenched by addition of NaHSO$_4$ (0.24 g in 5 mL of water) and warmed up to room temperature. The aqueous layer was extracted with EtOAc (15 mL×2), and the combined organic solution was dried over anhydrous MgSO$_4$, filtered, concentrated, and the residue was purified with column chromatography on silica gel to obtain the product as a light yellow solid (0.117 g Yield 38%).

Example 26

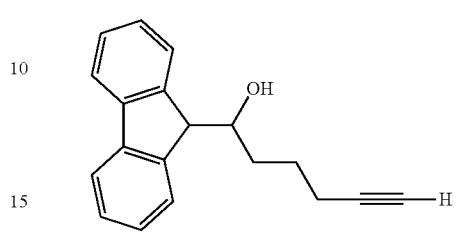

Under a nitrogen atmosphere, n-butyllithium (2.5 M in hexanes, 0.47 mL, 1.35 mmol) was added into the solution of fluorene (0.24 g, 1.48 mmol) in anhydrous THF (2 mL) at −78° C., and the reaction mixture was stirred at the same temperature for 2.5 h. A solution of 5-hexynal was added and the reaction was stirred at −78° C. for 3 hours, quenched by addition of sat. aq. NH$_4$Cl, and warmed to room temperature. The mixture was extracted with EtOAc, and then the combined organic phase was washed with brine, dried over anhydrous MgSO$_4$, filtered, and concentrated under reduced pressure. The crude product was purified by column chromatography on silica gel to obtain the desired product as a pale yellow solid (0.040 g, yield 11.9%).

Example 27

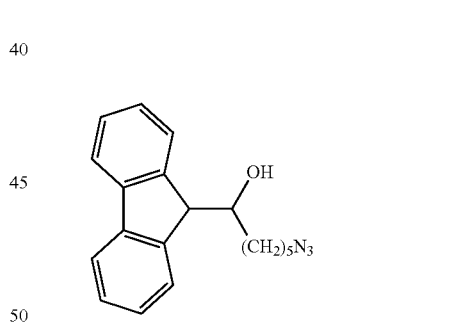

Under a nitrogen atmosphere, n-butyllithium (2.5 M in hexanes, 0.47 mL, 1.35 mmol) is added to a solution of fluorene (0.24 g, 1.48 mmol) in anhydrous THF (2 mL) at −78° C., and the reaction mixture is stirred at the same temperature for 2.5 h. A solution of 6-azidohexanal is added and the reaction is stirred at −78° C. for 3 hours, quenched by addition of sat. aq. NH$_4$Cl, and warmed to room temperature. The mixture is extracted with EtOAc, and then the combined organic phase is washed with brine, dried over anhydrous MgSO$_4$, filtered, and concentrated under reduced pressure. The crude product is purified by column chromatography on silica gel to obtain the desired product.

Example 28

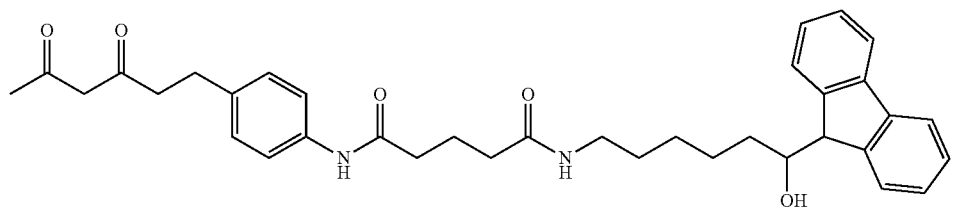 [SMILES: CC(=O)CC(=O)CCc1ccc(NC(=O)CCCC(=O)NCCCCCC(O)C2c3ccccc3-c3ccccc32)cc1]

A solution of 9-(6-azido-1-hydroxyhexyl)fluorene (1 Eq) in 9:1 dimethylformamide/water is treated with trimethylphosphine (10 Eq) for 1 hr at ambient temperature. To the resulting solution is added 4-[4-(3,5-Dioxo-hexyl)-phenylcarbamoyl]-butyric acid (1 Eq) and dimethylaminopropyl-ethyl-carbodiimide (EDCI) (5 Eq). After stirring overnight, the mixture is diluted with ethyl acetate and washed sequentially with water, 1N HCl, sat. aq. NaHCO₃, and brine, then dried over MgSO₄, filtered, and concentrated. The product is isolated by chromatography on silica gel.

Example 29

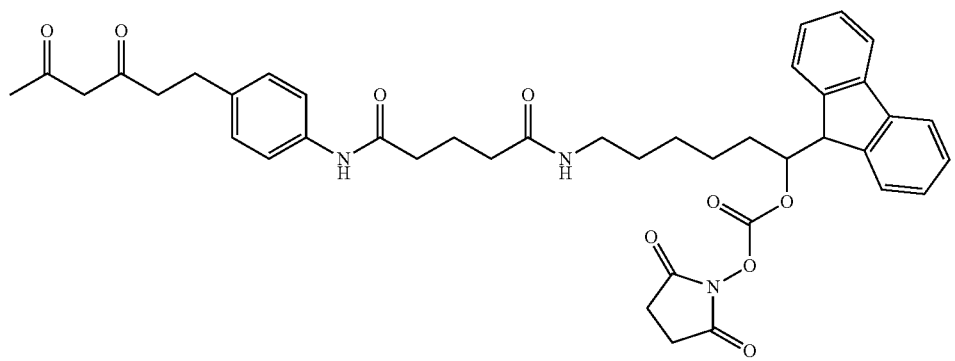 [SMILES: CC(=O)CC(=O)CCc1ccc(NC(=O)CCCC(=O)NCCCCCC(OC(=O)ON2C(=O)CCC2=O)C2c3ccccc3-c3ccccc32)cc1]

A solution of the compound of Example 28 (1 Eq) in chloroform is treated with triphosgene (5 equivalents) for 24 hours at ambient temperature. The solvent is removed by evaporation to provide the crude chloroformate.

The chloroformate is dissolved in THF and treated with N-hydroxysuccinimide (4 equivalents) and 2.6-lutidine (6 equivalents) at ambient temperature. When complete as judged by HPLC analysis, the mixture is diluted with ethyl acetate and washed sequentially with 1 N HCl, water, and brine, then dried over MgSO₄, filtered, and evaporated. The product N-hydroxysuccinimidoyl carbonate is purified by HPLC chromatography.

Example 30

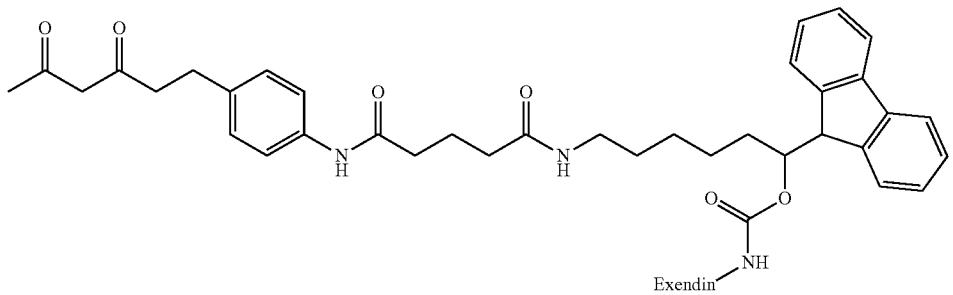

A solution of exendin-4 (HGEGTFTSDL SKQMEEEAVR LFIEWLKNGG PSSGAPPPS) in aqueous buffer, pH 7.5, is treated with a solution of the activated compound of Example 29 (1 equivalent) in DMSO. The pH is maintained as necessary by the addition of 1 N NaOH. The reaction progress is monitored by HPLC. When judged complete, the mixture is purified by preparative HPLC.

Example 31

Formation of an Antibody-Exendin Conjugate

Antibody (for example, h38C2 IgG1 or b12 IgG1; see US Patent Publication 2006/0205670 A1) is added to a solution of a compound of Example 30 to a final concentration of 25 nM antibody binding site and 125 nM (2). This mixture is incubated at room temperature for 10 minutes. The formation of the conjugate is determined by the formation of UV absorbance at 318 nm.

Example 32

Use of Conjugate Mixtures

In addition to controlling the release of a single drug, the technology of the invention can be used to control the release rates—and thus steady state concentrations and durations of action—of two or more drugs. Hence, for combinations of two drugs one can optimize the concentration and duration of both drugs. In one embodiment, an optimal drug-macromolecule conjugate for a first drug A is experimentally determined. Such an optimal drug-macromolecule conjugate is characterized as having an optimal drug concentration versus time profile (i.e., optimal drug concentrations and length of exposure). Using the optimized drug-macromolecule conjugate of the first drug A together with multiple drug-macromolecule conjugates of the second drug B, each conjugate of drug B having a different drug release profile, the most effective combination is then determined experimentally. A converse experiment may then be undertaken, using the optimal conjugate of drug b together with multiple drug-macromolecule conjugates of the second drug a in order to verify that the optimal mixture has been determined.

In another embodiment of the invention, each of drugs A and B are made into conjugates that have a set of half-lives for release of the drugs from the drug-macromolecule conjugates (for example: 1, 2, 4, and 8 hr half-lives). Combinations of these conjugates that span all the possible permutations of conjugates of drug A and B are then tested. (Table 1).

TABLE 1

Exemplary permutations of drug combination conjugates to be tested to determine optimal combination.

| T½ of B conjugate | T½ of A-conjugate | | | |
|---|---|---|---|---|
| | w | x | y | z |
| a | w, a | x, a | y, a | z.a |
| b | w, b | x, b | y, b | z, b |
| c | w, c | x, c | y, c | z, c |
| d | w, d | x, d | y, d | z, d |

Half-lives of release of first drug A from conjugate = w, x, y, and z hrs. Half-lives of release of second drug B from conjugate = a, b, c, and d hrs.

Example 33

General Procedure for Preparation of Sulfone Linkers

Sulfone linkers may be generally prepared by first reacting an appropriate thiol with a bromoketone to generate an beta-ketosulfide, which is subsequently oxidized to the beta-ketosulfone; reduction of the carbonyl then yields a beta-hydroxysulfone.

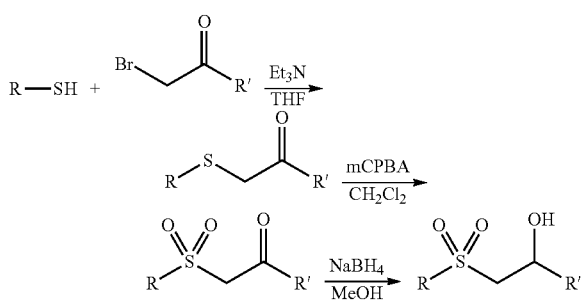

In one example, this is illustrated by the reaction of a thiophenol and a bromo-acetophenone as follows.

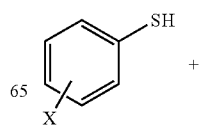

Compounds prepared using this method:

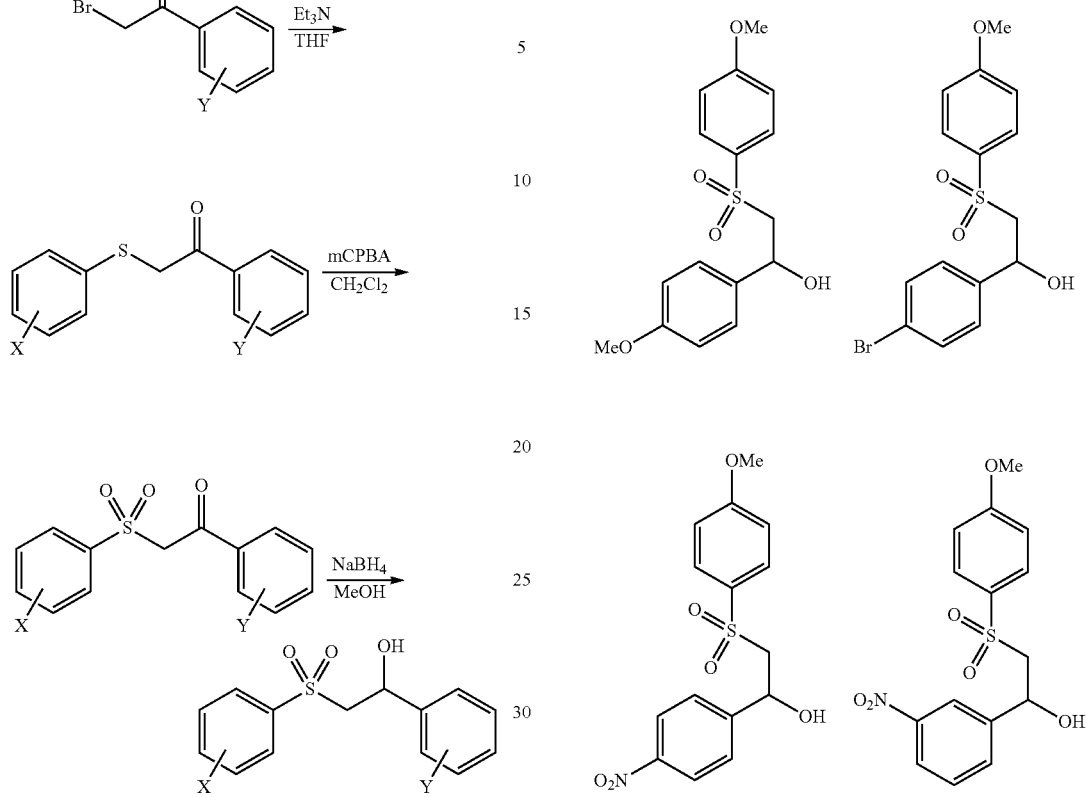

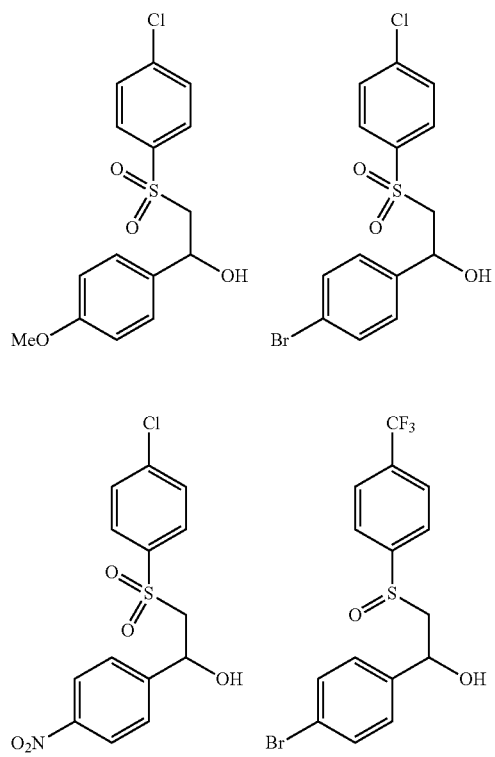

To a solution of the appropriate thiophenol (1 eq) and appropriate 2-bromoacetophenone (1 eq) in tetrahydrofuran (THF) is added triethylamine (Et$_3$N) (1.2 eq). The reaction is stirred at ambient temperature for 1 hour. After diluting with ethyl acetate (EtOAc), the reaction is quenched with sat. NH$_4$Cl (aq). The layers are separated, and the aqueous phase is extracted with EtOAc (2×). The combined organic layers are dried over MgSO$_4$, filtered, and concentrated by rotary evaporation to provide crude mercaptoketone.

To a solution of the mercaptoketone (1 eq) is added 3-chloroperoxybenzoic acid (mCPBA) (3 eq) portionwise. For sequences aimed at generating the sulfoxides, use of 1 eq of mCPBA suffices. The reaction is stirred at ambient temperature until TLC analysis indicated that reaction progress was complete. After diluting with EtOAc, the reaction is washed with NaHCO$_3$ (aq). The layers are separated, and the aqueous phase is extracted with EtOAc (2×). The combined organic layers are dried over MgSO$_4$, filtered, and concentrated to provide crude ketosulfone. Purification by silica gel chromatography (eluting with EtOAc in hexanes) provides the desired ketosulfone.

To a suspension of ketosulfone (1 eq) in MeOH is added solid NaBH$_4$ (1 eq) portionwise. The reaction is stirred at ambient temperature until TLC analysis indicates that reaction progress is complete, typically 30 minutes. Careful quench with NH$_4$Cl (aq) is followed by dilution with EtOAc. The layers are separated, and the aqueous phase is extracted with EtOAc (2×). The combined organic layers are dried over MgSO$_4$, filtered, and concentrated to provide crude hydroxysulfone, which can be purified either by silica gel chromatography (eluting with EtOAc in hexanes) or crystallization (EtOAc/hexane).

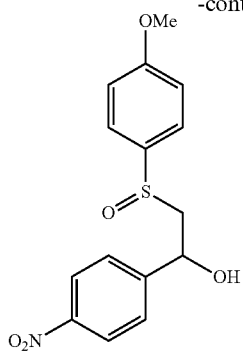

Replacement of the bromoacetophenone with an appropriate aliphatic bromoketone allows for preparation of linkers with the corresponding aliphatic segments Example 34

Preparation of a Bifunctional Sulfone Linker

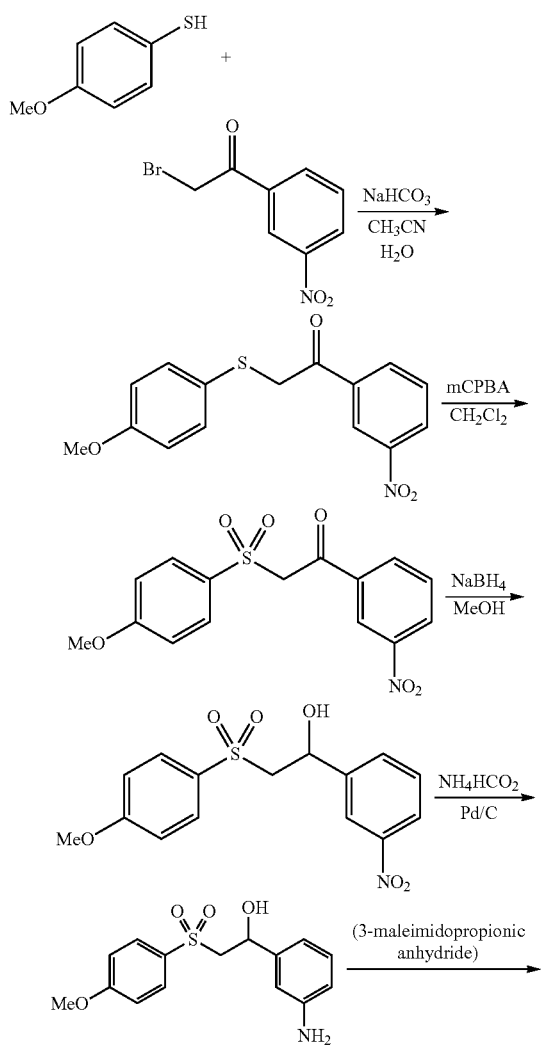

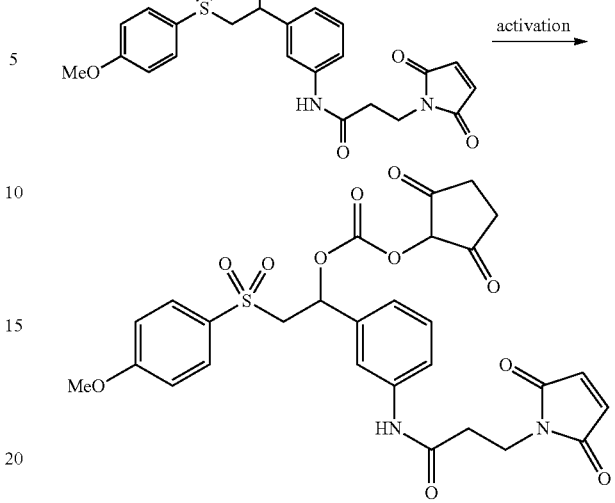

Step 1. 4-methoxythiophenol (615 µL) was added to a mixture of 2-bromo-3'-nitroacetophenone (1.22 g) in 10 mL of 1:1 acetonitrile/water with sodium bicarbonate (0.84 g). After 1 hour, the resulting mixture was diluted with water and extracted with ethyl acetate. The extract was dried with MgSO$_4$, filtered, and evaporated to an orange oil, which crystallized upon addition of 3:1 hexane/ethyl acetate. The orange crystals were collected and dried to provide the beta-ketosulfide, 1.1 g.

Step 2. Wet 3-chloroperoxybenzoic acid (2.0 g, ~50%) was added carefully in small portions to a solution of the ketosulfide (670 mg) in 10 mL of dichloromethane. The mixture warmed. After stirring 2 hrs, the suspension was diluted with ethyl acetate and washed carefully with sat. NaHCO$_3$, water, and brine, then dried with MgSO$_4$, filtered, and evaporated to give 630 mg of solid ketosulfone, which was crystallized from ethyl acetate.

Step 3. Sodium borohydride (100 mg) was added to a suspension of ketosulfone (400 mg) in 5 mL of methanol. After 30 min, sat. aq. NH$_4$Cl was added and the mixture was concentrated. The residue was partitioned between ethyl acetate and water, then the organic phase was washed with brine, dried with MgSO$_4$, filtered, and evaporated to give the crude product, which was crystallized from ethyl acetate/hexane to give 360 mg of the nitro alcohol.

Step 4. Solid ammonium formate (200 mg) was added to a mixture of the nitro alcohol (217 mg) and 10% palladium on carbon (50 mg) in 5 mL of methanol. The mixture was stirred vigorously for 1 hr, then an additional 50 mg of catalyst was added. After an additional 30 minutes, the mixture was filtered and evaporated. The residue was dissolved in ethyl acetate and washed carefully with sat. NaHCO$_3$, water, and brine, then dried with MgSO$_4$, filtered through a plug of silica gel, and evaporated to give 180 mg of the amino alcohol as a clear glass.

Step 5. The amino alcohol may be acylated on the amine to provide a more facile means of attachment to the macromolecular carrier, using methods known in the art. For example, a solution of the amino alcohol can be reacted with 3-maleimidopropionic acid anhydride as described for 2-aminofluorenes (Tsubery, H., et al., *J. Biological Chem.* (2004) 279: 38118-38124). Alternatively, the amino alcohol may be acylated on the amine using an azido-acid derivative, for example 6-azidohexanoyl chloride or 6-azidohexanoic anhydride. Alternatively, the amino alcohol may be acylated on the amine using an alkynyl-acid derivative, for example 5-hexynoyl chloride or 5-hexynoic anhydride.

Step 6. The acylated amino alcohol is activated for attachment of the drug as the N-hydroxysuccinimdyl carbonate, using the methods described above or known in the art.

Example 35

General Procedure for Preparation of Nitrile Linkers

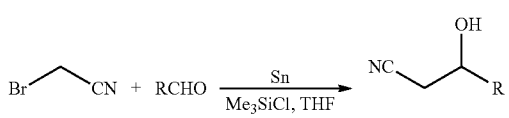

In one method, nitrile linkers may be prepared according to the tin-mediated reaction of bromoacetonitrile with aldehydes according to the method of Sun and Shi, *J. Chem. Research* (S) (1999), 318-319, which is incorporated herein by reference.

In another method, nitrile linkers may be prepared by reduction of beta-ketonitriles, which in turn may be prepared from suitable ketones by reaction of a beta-ketoaldehyde enolate with hydroxylamine hydrochloride:

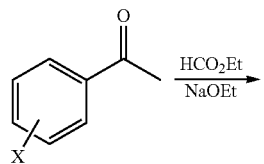

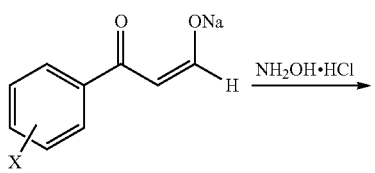

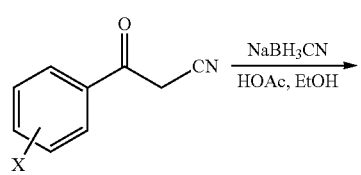

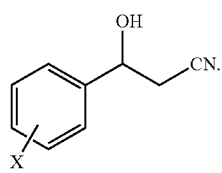

For example, the preparation of benzoylacetonitrile is provided in U.S. Pat. No. 6,861,162.

Example 36

Preparation of 3-(4-bromophenyl)-3-hydroxypropanenitrile

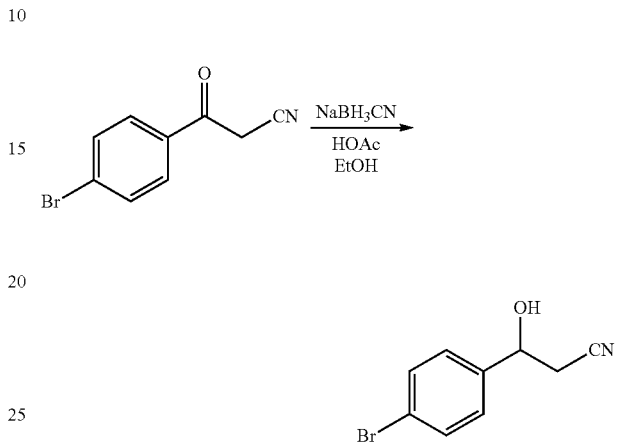

A suspension of 4-bromobenzoylacetonitrile (500 mg) in ethanol (5 mL) and acetic acid (300 μL) was heated with sodium cyanoborohydride (280 mg) using an 80° C. hot plate for 2 hours. After cooling to ambient temperature, the mixture was diluted with water and concentrated to a syrup, which was diluted with ethyl acetate and washed with water, sat. NaHCO$_3$, and brine. The extract was dried with MgSO$_4$, filtered, and evaporated to provide 510 mg of a cloudy oil, which was filtered through silica gel using 1:1 ethyl acetate/hexane to provide the product (496 mg) as a thick oil.

Example 37

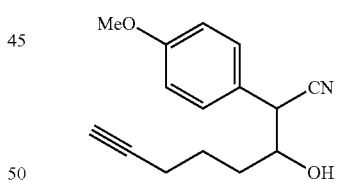

Under the protection of N$_2$, n-butyllithium (1.8 mL, 5.2 mmol) was added to a solution of N,N-diisopropylamine (0.75 mL, 5.2 mmol) in anhydrous THF (10 mL) at 0° C. The reaction mixture was stirred for 30 min and then was chilled to −78° C. 2-(4-methoxyphenyl)acetonitrile (0.6 mL, 4.34 mmol) was added into the above mixture via syringe. After stirring at the same temperature for 30 min, a solution of 5-hexynal (ca. 4 mmol) was added into the flask by syringe and the reaction mixture was stirred at −78° C. for 1.5 hours. The reaction was quenched by addition of a saturated solution of NH$_4$Cl, and then warmed to room temperature. The mixture was extracted with EtOAc (3×30 mL), and the combined organic solution was dried over MgSO$_4$, and concentrated under reduced pressure. The product was purified by silica gel chromatography. $^1$H-NMR (CDCl$_3$): δ 7.18 (d, 2H, J=5.4

Hz), 6.83 (d, 2H, J=5.4 Hz), 3.72-3.76 (s+m, 5H), 2.47 (1H, s), 2.13 (m, 2H), 1.88 (t, 1H), 1.51-1.68 (m, 4H).

Example 38

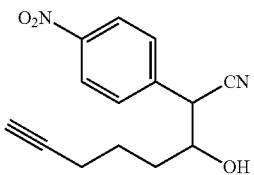 [SMILES: C#CCCCC(O)C(C#N)c1ccc([N+](=O)[O-])cc1]

This product was prepared according to the method of Example 33, substituting 2-(4-nitrophenyl)acetonitrile in place of 2-(4-methoxyphenyl)acetonitrile. $^1$H-NMR (CDCl$_3$): δ 8.20 (d, 2H, J=5.6 Hz), 7.51 (d, 2H, J=5.6 Hz), 3.99 (m, 2H), 2.17 (m, 2H), 1.89 (br s, 1H), 1.65 (m, 2H), 1.55 (m, 2H).

Example 39

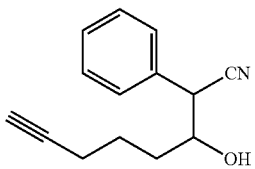 [SMILES: C#CCCCC(O)C(C#N)c1ccccc1]

This product was prepared according to the method of Example 37, substituting 2-phenylacetonitrile in place of 2-(4-methoxyphenyl)acetonitrile. $^1$H-NMR (CDCl$_3$): δ 7.3 (m, 5H), 3.9 (m, 2H), 2.23 (m, 2H), 1.96 (br s, 1H), 1.77 (m, 2H), 1.60 (m, 2H).

Example 40

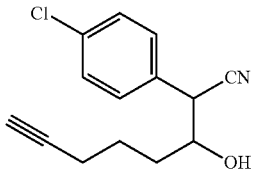 [SMILES: C#CCCCC(O)C(C#N)c1ccc(Cl)cc1]

This product was prepared according to the method of Example 37, substituting 2-(4-chlorophenyl)-acetonitrile in place of 2-(4-methoxyphenyl)acetonitrile. $^1$H-NMR (CDCl$_3$): δ 7.2-7.3 (m, 4H), 3.8 (m, 2H), 2.23 (m, 2H), 1.96 (br s, 1H), 1.8-1.5 (m, 4H).

Example 41

General Procedure for Activation Using N,N'-disuccinimidyl Carbonate

A mixture of the compound prepared as in Example 33 (1 mmol), N,N'-disuccinimidyl carbonate (2 mmol), and 4-(dimethylamino)pyridine (0.1 mmol) in 2 mL of dry acetonitrile is allowed to stir for 1 hour (for primary alcohols) or for 16 hours (for secondary alcohols), then is diluted with 5 mL of water containing 0.2 mL of 1 N HCl and extracted with ethyl acetate. The organic phase is washed with water and brine, then dried over MgSO$_4$, filtered, and concentrated to provide the crude mixed carbonate, suitable for further use. The mixed carbonate is optionally further purified by silica gel chromatography using ethyl acetate/hexane.

Compounds prepared according to this method include:

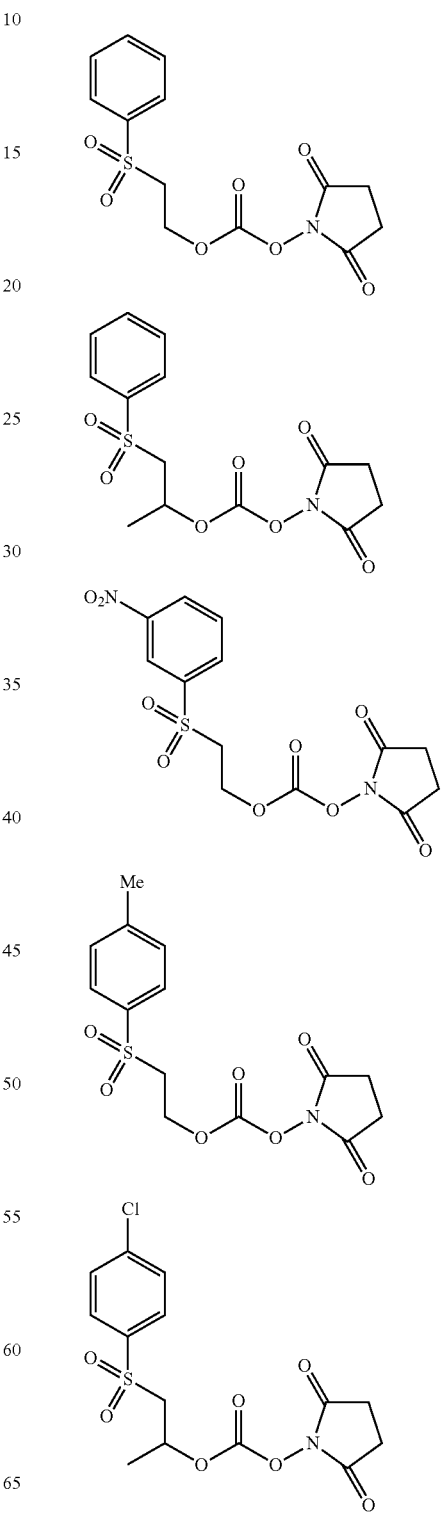

139
-continued
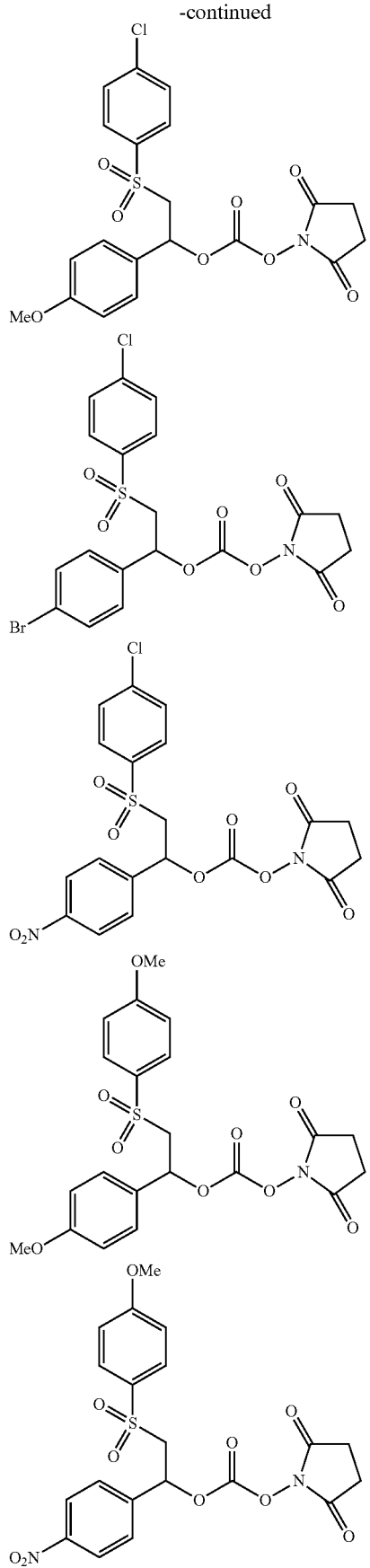
140
-continued
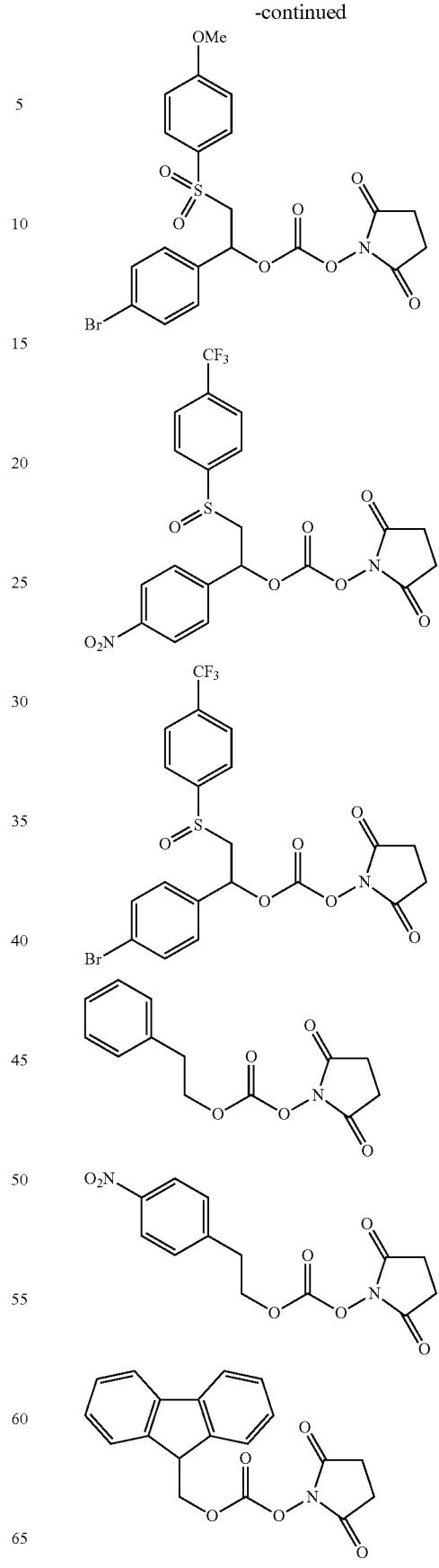

141
-continued

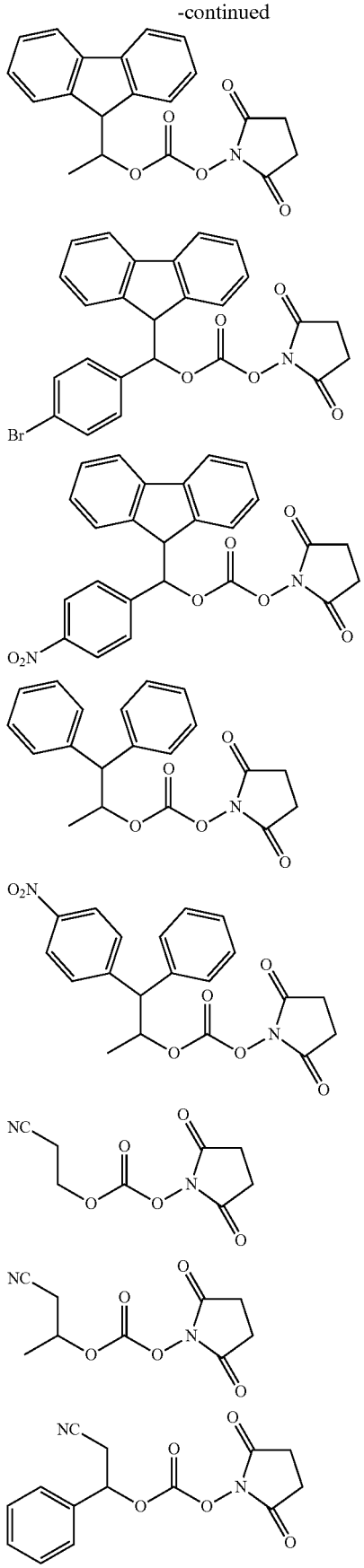

142
-continued

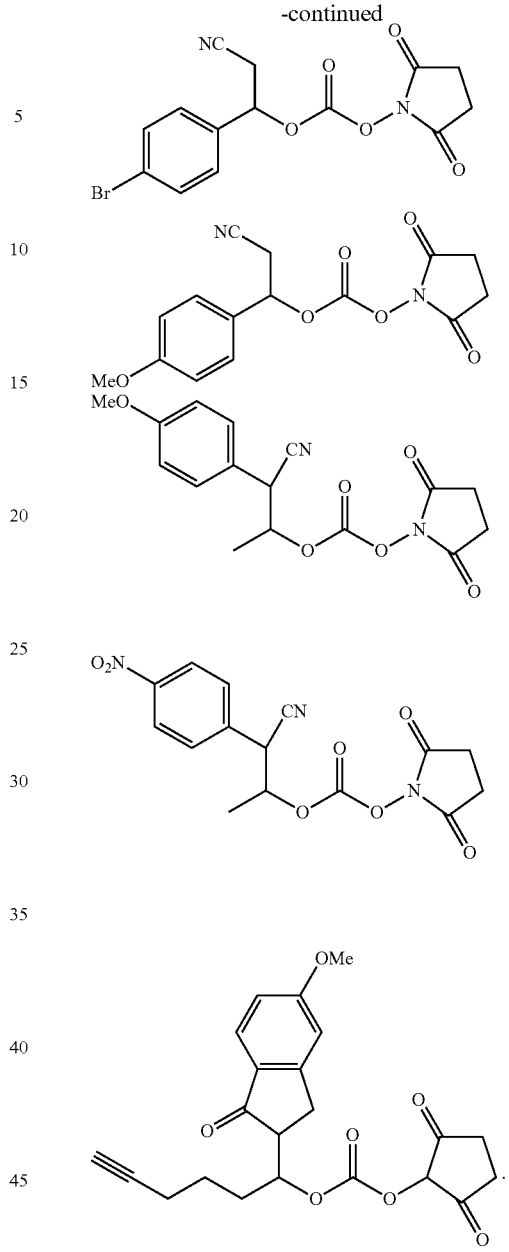

Example 42

General Procedure for Activation Using Triphosgene and N-Hydroxysuccinimide

A solution of an alcohol of formula (1) (0.5 mmol) and triphosgene (0.72 mmol) in 5 mL of anhydrous tetrahydrofuran (THF) is stirred under inert atmosphere, and pyridine (84 µL) is added dropwise to give a white precipitate. After 10 minutes, the mixture is filtered using nitrogen pressure and concentrated to remove excess phosgene. The residue is redissolved in 5 mL of THF and treated with N-hydroxysuccinimide (2.65 mmol) and pyridine (130 µL) for 20 minutes, then evaporated, to dryness. The residue is dissolved in ethyl acetate, washed successively with water, 0.1 N HCl, sat. NaHCO$_3$, and brine, then dried over MgSO$_4$, filtered, and evaporated to provide the crude carbonate. Purification by chromatography on silica gel (ethyl acetate/hexane) provides the product.

Example 43

Activation of (4-bromophenyl)-(9-fluorenyl)methanol using triphosgene and N-hydroxysuccinimide

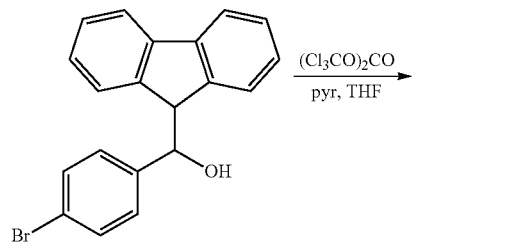

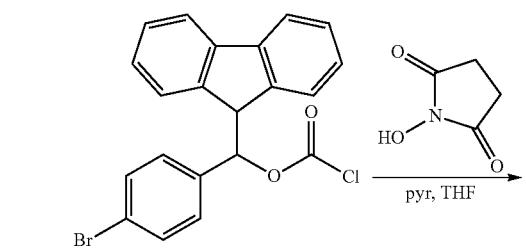

A solution of (4-bromophenyl)-(9-fluorenyl)methanol (175 mg, 0.5 mmol) and triphosgene (212 mg, 0.72 mmol) in 5 mL of anhydrous THF was treated with pyridine (84 µL) for 10 minutes under inert atmosphere, then filtered and evaporated. The residue was dissolved in 5 mL of THF and treated with N-hydroxysuccinimide (310 mg, 2.65 mmol) and pyridine (130 µL) for 209 minutes, then evaporated to dryness. The residue was dissolved in ethyl acetate, washed successively with water, 0.1 N HCl, sat. NaHCO$_3$, and brine, then dried over MgSO$_4$, filtered, and evaporated to provide the crude carbonate. The crude product was dissolved in 1 mL of dichloromethane and loaded onto a 5-mL column of silica gel equilibrated in hexane. Initial elution using hexane removed some colored material. The column was then eluted with 3:1 hexane/ethyl acetate, and finally 1:1 hexane/ethyl acetate which eluted the purified product (206 mg, 92%).

Example 44

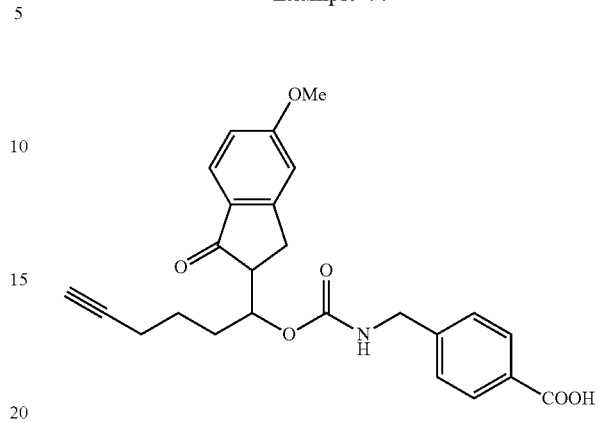

The crude mixed carbonate of Example was dissolved in DMSO (0.5 mL) and mixed with sodium 4-(aminomethyl) benzoate (0.1 mL of a 1.0 M solution in water). After 5 minutes, the mixture was diluted with 5 mL of water, and the milky solution was washed three times with dichloromethane. The aqueous phase was acidified using 1 N HCl, then extracted three times with ethyl acetate. The ethyl acetate extracts were combined, washed with water, dried over MgSO$_4$, filtered, and evaporated to dryness. The residue is washed once with 1:1 EtOAc/hexanes, then dissolved in EtOAc and reconcentrated to provide the purified product (7 mg).

Example 45

General Method for Preparation of N$_\epsilon$-(2,4-Dinitrophenyl)-L-Lysine Derivatives

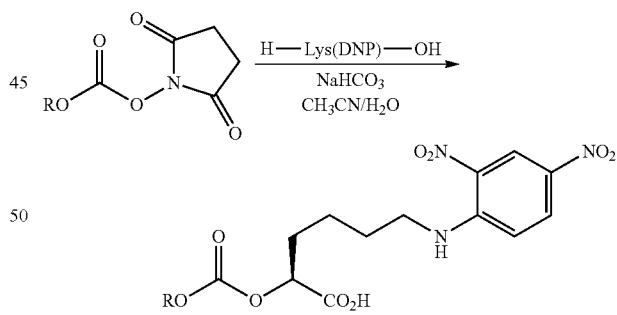

A solution of N$_\epsilon$-(2,4-dinitrophenyl)-L-lysine hydrochloride (35 mg) in 600 µL of water and 200 µL of 1.0 N NaOH is treated successively with 200 µL of 1.0 M NaHCO$_3$ and a solution of 0.1 mmol of the N-hydroxysuccinimide carbonate in 1.0 mL of acetonitrile. The resulting yellow solution is stirred at ambient temperature for 1 hour, then is diluted by addition of 10 mL of water and is loaded onto a C18 solid phase extraction column (Varian BondElut, 1 g). The column is washed with 3 mL of water, 1 mL of 1% CF$_3$CO$_2$H in water, 3 mL of water, then 3 mL of 50% aqueous methanol to elute any unreacted lysine analog. The product is eluted with 100% methanol, and the yellow solution is evaporated to dryness.

Example 46

General Method for Measurement of Drug Release Rates from Compounds of Formula (2)

This illustrates one example of a method to measure the rate of release of a drug from a compound of formula (2). Stock solutions of the compound of formula (2) are prepared by dissolving the compound in a suitable water-miscible solvent, for example DMSO or acetonitrile. A suitable volume of this stock solution is then diluted into aqueous buffer optionally containing an internal standard for HPLC analysis, for example a sodium benzoate, to provide a clear solution, which is maintained at a set temperature. Poorly soluble compounds may require addition of a cosolvent such as DMSO. Aliquots are periodically removed and either immediately analyzed by HPLC or quenched by addition of an equal volume of 1% trifluoroacetic acid (TFA) in acetonitrile and stored for later analysis. A portion of the aliquot is injected onto an HPLC column for analysis. The areas of the peaks for the remaining compound of formula (2) and, if possible, the drug itself, are then measured and compared to the area of the peak for the internal standard. In certain cases, for example using drugs that do not have sufficiently strong UV light absorbance to detect by HPLC, the concentration of free drug may be measured by mass spectral analysis.

As one example, the rates of release of $N_\epsilon$-(2,4-dinitrophenyl)-L-lysine, "H-Lys(DNP)—OH", from various compounds were determined as follows. Reaction mixtures were prepared containing 0.1 M buffer, 0.05% $NaN_3$, and approximately 0.1 mg/mL of the starting compound, and were kept at 37° C. Aliquots were removed periodically and analyzed by injection onto a Varian Polaris 3 μm C18-A reversed-phase HPLC column (150×4.6 mm), equilibrated in 50:50 water/methanol (each containing 0.5% acetic acid) at a flow rate of 0.8 mL/min. Compounds were eluted from the column using a gradient to 100% methanol+0.5% acetic acid, and detected by absorbance at 350 nm. Peak integration gave areas for remaining starting material ($A_S$) and for released H-Lys(DNP)—OH ($A_P$), and the percent reaction was calculated according to % reaction=$A_P/(A_P+A_S)*100$ Release rates were then calculated from the slope of a plot of ln(100−% reaction) versus time, and half-lives were calculated as $T_{1/2}$=ln(2)/rate.

Half-lives for release of Nε-(2,4-dinitrophenyl)-L-lysine (H-Lys(DNP)—OH) as a model for drug release were determined in PBS, pH 7.4, 37° C. for the following compounds with the results as shown. It is evident that the nature of $R^1$ and $R^2$ and the substituents thereon provide a wide range of release rates.

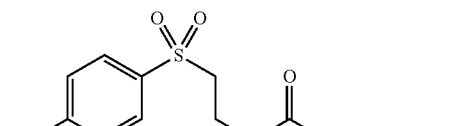

$T_{1/2}$ = 56 hrs

-continued

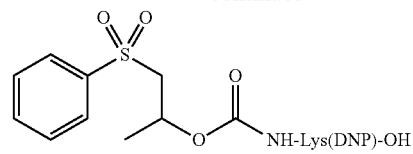

$T_{1/2}$ = 72 hrs

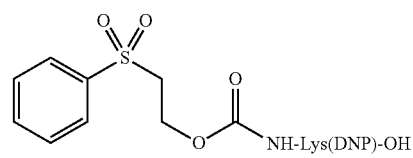

$T_{1/2}$ = 30 hrs

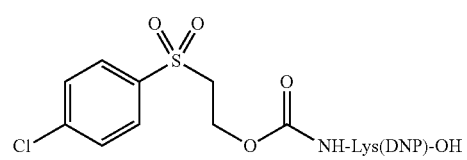

$T_{1/2}$ = 46 hrs

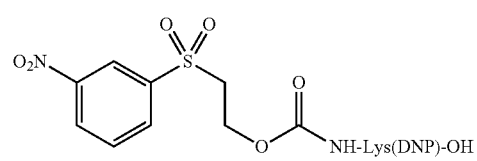

$T_{1/2}$ = 2 hrs

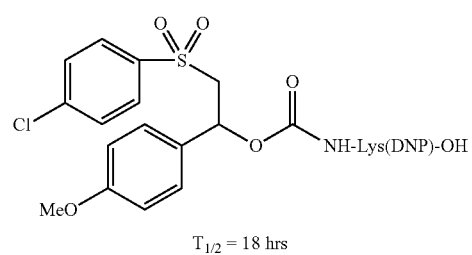

$T_{1/2}$ = 18 hrs

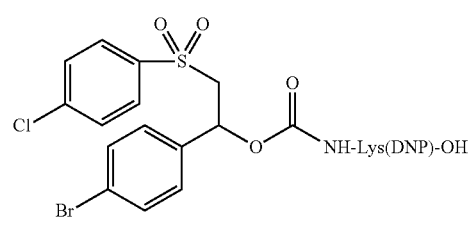

$T_{1/2}$ = 17 hrs

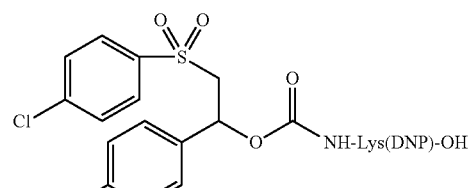

$T_{1/2}$ = 2 hrs

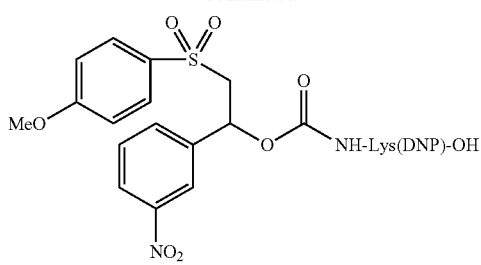

$T_{1/2}$ = 13 hrs

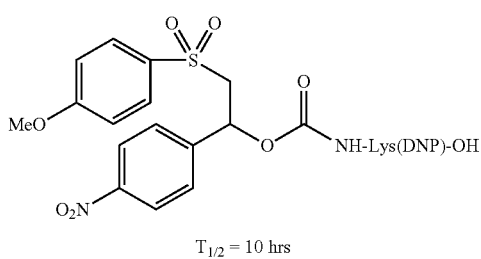

$T_{1/2}$ = 10 hrs

Half-lives for release of Nε-(2,4-dinitrophenyl)-L-lysine H-Lys(DNP)—OH) from sulfonyl linkers in PBS, pH 7.4, 37° C.

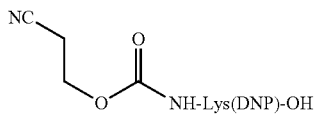

$T_{1/2}$ = 160 hrs (pH 8.3)

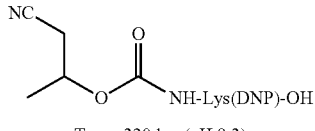

$T_{1/2}$ = 320 hrs (pH 8.3)

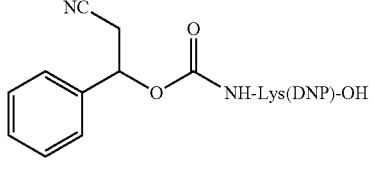

$T_{1/2}$ = 98 hrs (pH 8.3)

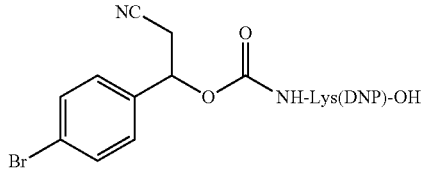

$T_{1/2}$ = 270 hrs (pH 7.4)

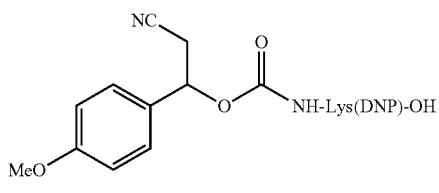

$T_{1/2}$ = 22 hrs (pH 7.4)

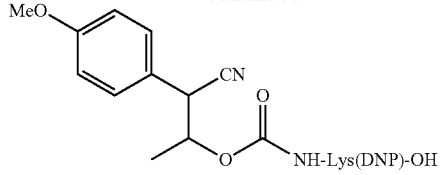

$T_{1/2}$ = 125 hrs (pH 7.4)

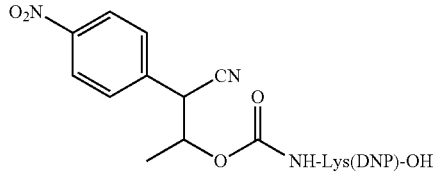

$T_{1/2}$ = 80 hrs (biphasic; pH 7.4)

Half-lives for release of Nε-(2,4-dinitrophenyl)-L-lysine (H-Lys(DNP)—OH) from nitrile linkers in PBS, pH 7.4, or in 0.1 M Tris.HCl, pH 8.3, 37° C.

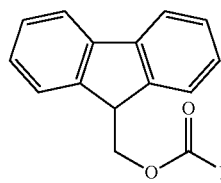

$T_{1/2}$ = 200 hrs (pH 8.3)
~ 1650 hrs (pH 7.4)

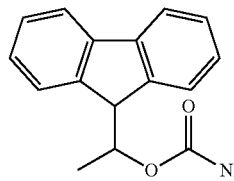

$T_{1/2}$ = 1800 hrs (pH 8.3)

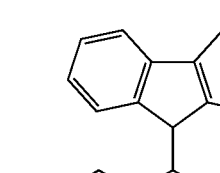

$T_{1/2}$ = 285 hrs (pH 8.3)

Half-lives for release of Nε-(2,4-dinitrophenyl)-L-lysine (H-Lys(DNP)—OH) from fluorenyl linkers in PBS, pH 7.4, or in 0.1 M Tris.HCl, pH 8.3, 37° C.

Example 47

Preparation of Linked 4-Hydroxybenzyl Prodrugs

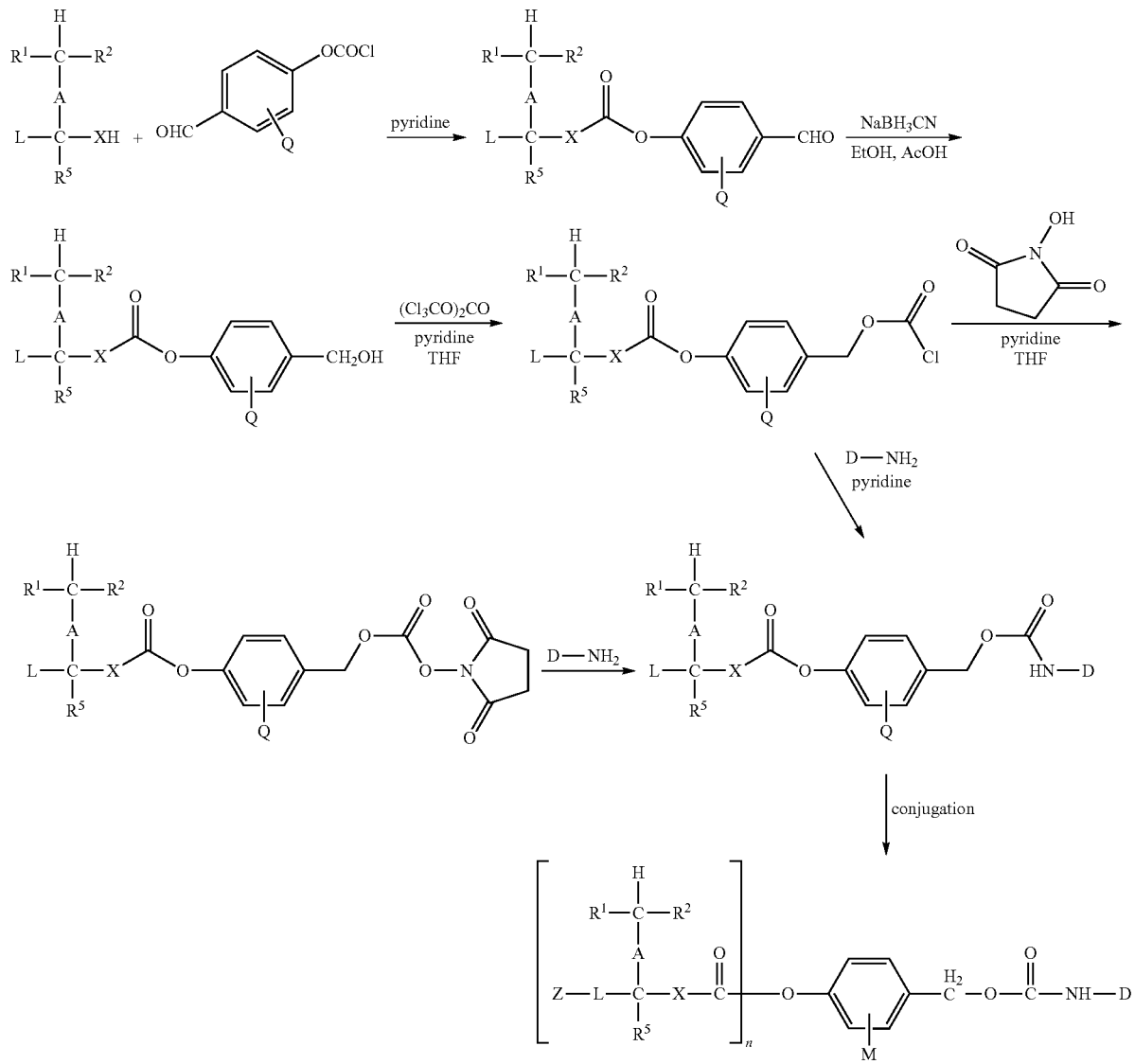

Step 1. Pyridine (1.5 mmol) is added to a mixture of the linker (1.0 mmol) and the 4-formylphenyl chloroformate (1.2 mmol) in dry tetrahydrofuran, and the reaction is monitored by thin-layer chromatography. Upon completion, the mixture is diluted with ethyl acetate, washed with water and brine, dried and concentrated. The crude aldehyde product is purified by chromatography on silica gel.

Step 2. Sodium cyanoborohydride (2 mmol) is added to a mixture of the aldehyde from Step 1 (1 mmol) in 5% acetic acid and ethanol (2 mL). The mixture is warmed to ~75° C. for 2 hours, then cooled and concentrated. The residue is dissolved in ethyl acetate, washed with water and brine, then dried and evaporated to provide the crude benzylic alcohol, which is purified by chromatography on silica gel.

Step 3. Pyridine (2 mmol) is added dropwise to a mixture of the benzylic alcohol of Step 2 (1 mmol) and triphosgene (3 mmol) in dry tetrahydrofuran. After stirring for 1 hour, the mixture is filtered and evaporated to dryness to provide the crude chloroformate, which is used without further purification.

Step 4. Pyridine (2 mmol) is added to a mixture of the crude chloroformate from Step 3 and N-hydroxysuccinimide (5 mmol). After stirring for 30 minutes, the mixture is filtered and concentrated. The residue is dissolved in ethyl acetate, washed with water and brine, then dried and evaporated to provide the crude succinimidyl carbonate, which is purified by chromatography on silica gel.

Step 5. A solution of the succinimidyl carbonate from Step 4 in acetonitrile (1 equivalent) is added to a solution of the amine-containing drug in 0.1 M $NaHCO_3$. After 1 hour, the mixture is diluted with water and loaded onto a C18 solid phase extraction cartridge, The cartridge is washed with water, then eluted with a step gradient of water and acetonitrile. The product-containing fractions are pooled and evaporated to dryness, and optionally further purified using preparative HPLC.

Example 48

Preparation of Linked 4-Aminobenzyl Prodrugs

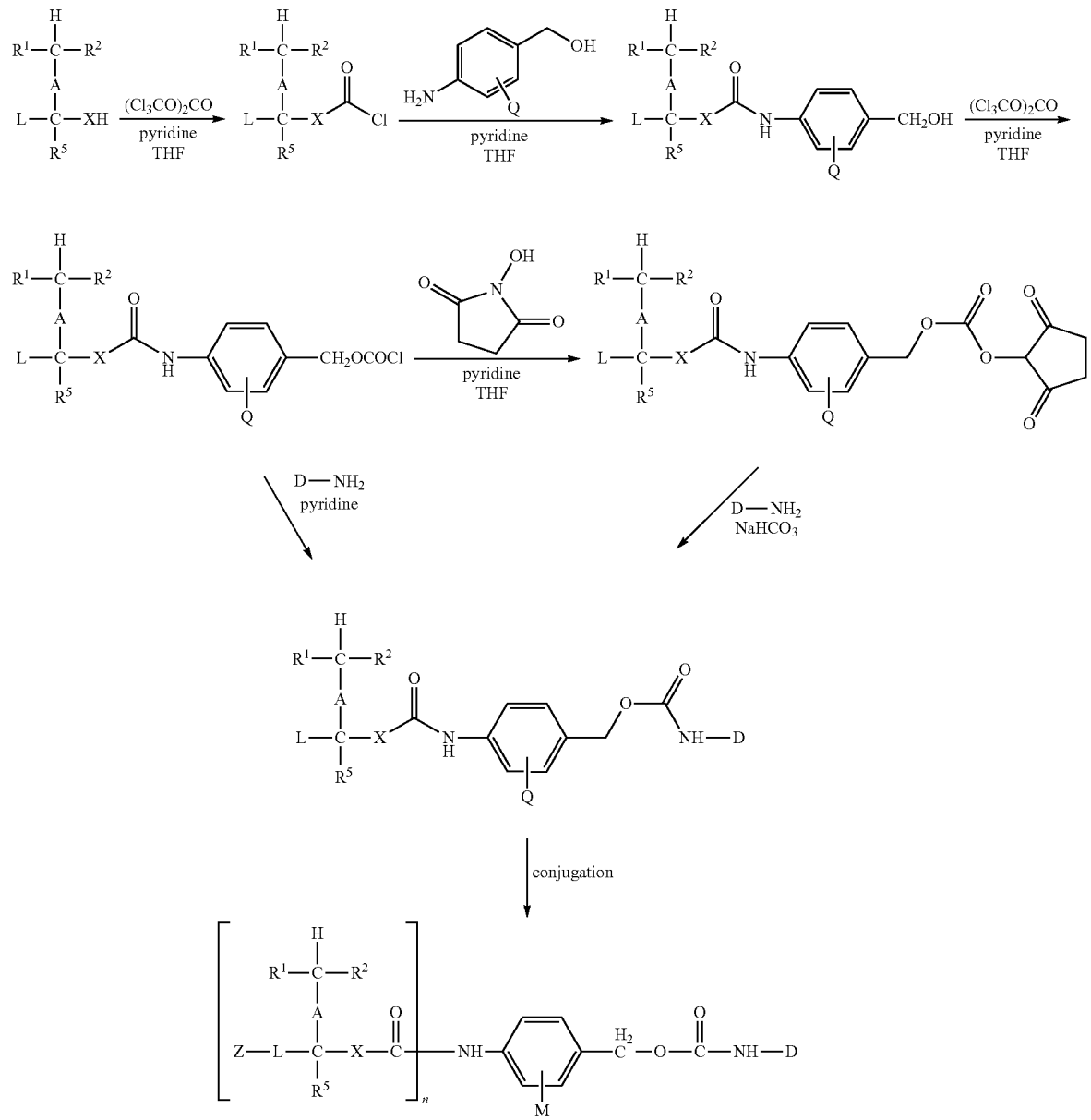

Step 1. Pyridine (1.5 mmol) is added to a mixture of the linker (1.0 mmol) and triphosgene (3 mmol) in dry tetrahydrofuran. After stirring for 1 hour, the mixture is filtered and evaporated to dryness to provide the crude chloroformate, which is used without further purification.

Step 2. A mixture of the crude chloroformate from Step 1, the 4-aminobenzyl alcohol (1 mmol), and pyridine (2 mmol) in dry tetrahydrofuran (5 mL) is stirred at ambient temperature. When complete, the mix is evaporated, and the residue is dissolved in ethyl acetate and washed with water and brine, then dried and evaporated to provide the crude carbamate, which is purified by chromatography on silica gel.

Step 3. Pyridine (2 mmol) is added dropwise to a mixture of the carbamate of Step 2 (1 mmol) and triphosgene (3 mmol) in dry tetrahydrofuran. After stirring for 1 hour, the mixture is filtered and evaporated to dryness to provide the crude chloroformate, which is used without further purification.

Step 4. Pyridine (2 mmol) is added to a mixture of the crude chloroformate from Step 3 and N-hydroxysuccinimide (5 mmol). After stirring for 30 minutes, the mixture is filtered and concentrated. The residue is dissolved in ethyl acetate, washed with water and brine, then dried and evaporated to provide the crude succinimidyl carbonate, which is purified by chromatography on silica gel.

Step 5. A solution of the succinimidyl carbonate from Step 4 in acetonitrile (1 equivalent) is added to a solution of the amine-containing drug in 0.1 M NaHCO$_3$. After 1 hour, the mixture is diluted with water and loaded onto a C18 solid phase extraction cartridge, The cartridge is washed with water, then eluted with a step gradient of water and acetoni-

The invention claimed is:

1. A compound of the formula

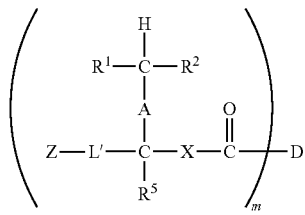

(3)

wherein m is an integer of 1-10;
Z is a macromolecule;
L' is a linker;
D is a drug or of a prodrug;
X is O or S;
A is alkenyl ($C_2$), aryl or absent;
each $R^1$ and $R^2$ is independently H; CN;
  $NO_2$;
  optionally substituted aryl;
  optionally substituted heteroaryl;
  optionally substituted alkenyl;
  optionally substituted alkynyl; or
each $R^1$ and $R^2$ is independently $COR^3$ or $SOR^3$ or $SO_2R^3$ wherein
  $R^3$ is H or optionally substituted alkyl;
    optionally substituted aryl;
    optionally substituted heteroaryl;
    optionally substituted alkenyl;
    optionally substituted alkynyl; or
    OR or $NR_2$ wherein each R is independently H or optionally substituted alkyl; or
each $R^1$ and $R^2$ is independently $SR^4$ wherein
  $R^4$ is optionally substituted alkyl;
  optionally substituted aryl;
  optionally substituted heteroaryl;
  optionally substituted alkenyl; or
  optionally substituted alkynyl;
wherein $R^1$ and $R^2$ may be joined to form a 3-8 member ring; and
wherein both $R^1$ and $R^2$ cannot be H;
wherein $R^5$ is H or alkyl ($C_{1-6}$).

2. The compound of claim 1 wherein m is 1.
3. The compound of claim 1 wherein $R^5$ is H.
4. The compound of claim 1 wherein the linker residue is a bivalent chain having a molecular weight between 14 Da and 20 kDa which may include unsaturation, heteroatoms, ring structures, aromatic portions, and/or heteroaromatic portions that covalently links Z to the remainder of the molecule.
5. The compound of claim 4 wherein the linker is a peptide or a pseudopeptide and/or comprises triazole and/or phenylene, and/or a maleimido.
6. The compound of claim 1 wherein the macromolecule is an antibody, a polysaccharide, an albumin, or a synthetic polymer.
7. The compound of claim 6 wherein the synthetic polymer is polyethylene glycol (PEG).
8. The compound of claim 1 wherein the drug is a peptide, a nucleic acid or a small molecule.
9. The compound of claim 1 wherein one of $R^1$ and $R^2$ is CN.
10. The compound of claim 1 wherein at least of one $R^1$ and $R^2$ comprises phenyl or phenylene.
11. The compound of claim 1 wherein one of $R^1$ and $R^2$ is $SO_2R^3$ and the other is H, alkyl or phenyl.
12. The compound of claim 1 wherein A is absent.
13. A compound of the formula

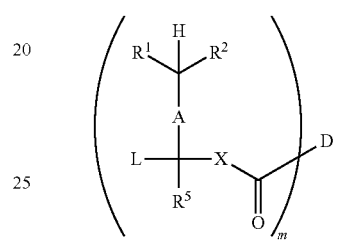

(2)

wherein m, $R^1$, $R^2$, $R^5$, A, X and D are defined as in claim 1, and wherein L is a linking group capable of binding to a macromolecule.

14. A compound of the formula

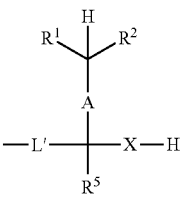

(4)

wherein $R^1$, $R^2$, $R^5$, A, X, Z and L' are defined as in claim 1.

15. A pharmaceutical composition which comprises the compound of claim 1.
16. A method to prepare a compound of formula (3) which method comprises reacting a compound of formula (2) with a macromolecule.
17. A method to prepare a compound of formula (3) which method comprises reacting a compound of formula (4) with a drug or prodrug under conditions whereby said drug or prodrug is coupled to the compound of formula (4).
18. A method to prepare a compound of formula (2) which method comprises reacting a compound of formula (1) with a drug or prodrug under conditions whereby said drug or prodrug is coupled to the compound of formula (1).

* * * * *

UNITED STATES PATENT AND TRADEMARK OFFICE
CERTIFICATE OF CORRECTION

PATENT NO.        : 8,680,315 B2                                              Page 1 of 1
APPLICATION NO.   : 12/999287
DATED             : March 25, 2014
INVENTOR(S)       : Santi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 545 days.

Signed and Sealed this

Twenty-ninth Day of September, 2015

Michelle K. Lee
*Director of the United States Patent and Trademark Office*